(12) United States Patent
He et al.

(10) Patent No.: US 7,714,014 B2
(45) Date of Patent: May 11, 2010

(54) TARGETING GLI PROTEINS IN HUMAN CANCER BY SMALL MOLECULES

(75) Inventors: Biao He, Foster City, CA (US); Naoaki Fujii, Germantown, TN (US); Liang You, San Francisco, CA (US); Zhidong Xu, San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 341 days.

(21) Appl. No.: 11/608,197

(22) Filed: Dec. 7, 2006

(65) Prior Publication Data

US 2007/0149592 A1 Jun. 28, 2007

Related U.S. Application Data

(60) Provisional application No. 60/763,829, filed on Jan. 30, 2006, provisional application No. 60/748,968, filed on Dec. 9, 2005.

(51) Int. Cl.
*A61K 31/415* (2006.01)
*C07D 231/06* (2006.01)

(52) U.S. Cl. .................................. 514/403; 548/379.4
(58) Field of Classification Search ................. 514/403; 548/379.4
See application file for complete search history.

(56) References Cited

U.S. PATENT DOCUMENTS

| | | | |
|---|---|---|---|
| 6,238,876 B1 | 5/2001 | Altaba | |
| 7,056,942 B2 * | 6/2006 | Hildesheim et al. | 514/411 |
| 2003/0049246 A1 | 3/2003 | Altaba | |
| 2005/0112707 A1 | 5/2005 | Altaba et al. | |
| 2005/0130922 A1 | 6/2005 | Altaba et al. | |
| 2005/0256076 A1 | 11/2005 | Bumcrot | |

FOREIGN PATENT DOCUMENTS

| | | |
|---|---|---|
| JP | 07-041459 A | 2/1995 |
| WO | WO 03/076409 A1 | 9/2003 |
| WO | WO 2005/051931 A2 | 6/2005 |

OTHER PUBLICATIONS

Sheng, et al. Activation of the hedgehog pathway in advanced prostate cancer. Mol Cancer. (2004) 3;3:29.
Abdallah, M.A. et al.; "Reaction of benzonitrilium N-phenylimide with (Z)- 4-arylmethyleneimidazol-5(4H)-ones"; 2001, *Indian Journal of Chemistry*, vol. 40B, pp. 187-190.
Hallikas, Outi et al.; "Genone-wide Prediction of Mammalian Enhancers Based on Analysis of Transcription-Factor Binding Affinity"; 2006, *Cell*, vol. 124, pp. 47-59.
Kasper, Maria et al.; "GLI transcription factors: Mediators of oncogenic Hedgehog signaling"; 2006, *European Journal of Cancer*, 9 pages.
Kinzler, Kenneth W. et al.; "The GLI Gene Encodes a Nuclear Protein Which Binds Specific Sequences in the Human Genome"; 1990, *Molecular and Cellular Biology*, vol. 10, No. 2, pp. 634-642.
Klemm, Richard D. et al.; "Molecular cloning and expression of the 32-kDa subunit of human TFIID reveals interactions with VP16 and TFIIB that mediate transcriptional activation"; 1995, *PNAS*, vol. 92, pp. 5788-5792.
Lu, Hua et al.; "Human $TAF_{II}31$ protein is a transcriptional coactivator of the p53 protein"; 1995, *PNAS*, vol. 92, pp. 5154-5158.
Sasaki, Hiroshi et al.; "Regulation of Gli2 and Gli3 activities by an amino-terminal repression domain: implication of Gli2 and Gli3 as primary mediators of Shh signaling"; 1999, *Development*, vol. 126, pp. 3915-3924.
Uesugi, Motonari et al.; "The α-helical FXXΦΦ motif in p53: TAF interaction and discrimination by MDM2"; 1999, *PNAS*, vol. 96, No. 26, pp. 14801-14806.
Uesugi, Motonari et al.; "Induced α Helix in the VP16 Activation Domain upon Binding to a Human TAF"; 1997, *Science*, vol. 277, pp. 1310-1313.
Yoon, Joon Won et al.; "GLI Activates Transcription through a Herpes Simplex Viral Protein 16-Like Activation Domain"; 1998, *The Journal of Biological Chemistry*, vol. 273, No. 6, pp. 3496-3501.

* cited by examiner

*Primary Examiner*—Joseph R Kosack
(74) *Attorney, Agent, or Firm*—Carol L. Francis; Bozicevic, Field & Francis, LLP

(57) ABSTRACT

This invention provides compositions, methods and kits for the diagnosis and treatment of cancers expressing a GLI polypeptide, and in particular a GLI1, GLI2 or GLI3 polypeptide. The invention provides small molecule compounds mimicking the transcriptional activation domain of a GLI polypeptide. The small molecule inhibitors of the invention specifically block the activator function of a GLI polypeptide, but not the repressor function of GLI3.

16 Claims, 25 Drawing Sheets

A.

B.

C.

A.

B.

C.

A.

B.

A.

B.

TARGETING GLI PROTEINS IN HUMAN CANCER BY SMALL MOLECULES

CROSS-REFERENCES TO RELATED APPLICATIONS

This application claims benefit of U.S. provisional application Ser. No. 60/748,968, filed Dec. 9, 2005, and U.S. provisional application Ser. No. 60/763,829, filed Jan. 30, 2006, the disclosures of which are incorporated herein in their entireties by reference.

FIELD OF THE INVENTION

The present invention relates generally to compositions and methods of inhibiting tumorigenesis, tumor growth and tumor survival. The compositions comprise small molecule compounds inhibiting Hedgehog and GLI signaling pathways.

BACKGROUND OF THE INVENTION

Hedgehog (Shh or Hh), WNT, FGF and BMP signaling pathways network together during embryogenesis, tissue regeneration, and carcinogenesis. Aberrant activation of Hh signaling pathways leads to pathological consequences in a variety of human tumors, such as gastric cancer and pancreatic cancer. Hedgehogs are secreted glycoproteins that initiate Hh signal transduction by binding to a transmembrane protein complex comprising PATCHED1 (ptch1) and SMOOTHENED (smo) and eliciting a cascade of cytoplasmic signal transduction events, including the inhibition of a protein kinase A that leads to the transcription of the GLI zinc-finger transcription factors. The GLI family of zinc-finger transcription factors then translate the extra-cellular Hh-stimulus into defined transcriptional programs in a context-dependent and cell-type specific manner (Ruiz I Altaba et al., 2002, *Nat. Rev. Cancer* 2:361-72).

Several proteins, including GLI proteins, are involved in mediating Hh signaling (Katoh and Katoh, 2005, *Cancer Biol. Ther.* 4:1050-4). Vertebrates have at least three distinct GLI proteins, GLI (also referred to as GLI1), GLI2, and GLI3. These proteins are members of the GLI family of zinc finger transcription factors and share a highly conserved $C_2$—$H_2$ zinc finger domain (having five zinc finger DNA-binding motifs) with *Drosophila* Cubitus interruptus (Ci) and the *Caenorhabditis elegans* sex-determining gene tra-1 (Hui et al., 1994, *Dev. Biol.* 162:402-13). In *Drosophila* Ci is required for activation of hedgehog targets and also functions as a repressor of hedgehog expression.

During embryonic development of vertebrates all genes whose expression is partially overlapping are transcriptionally activated in response to Hh-signaling and are able to mediate most of the effects caused by activation of the pathway. GLI1, GLI2 and GLI3 may each carry out a specific function during vertebrate development (Kinzler et al., 1984, *Nature* 332:371-374; Ruppert et al., 1988, *Mol. Cell. Biol.* 8:3104-3113; Walterhouse et al., 1993, *Dev. Dyn.* 196:91-102; Hui et al., 1994, *Dev. Biol.* 162:402-413). For example, Gli2 mutant mice exhibit severe skeletal abnormalities including cleft palate, tooth defects, absence of vertebral body and intervertebral discs, and shortened limbs and sternum (Mo et al., 1997, *Development* 124:113-23).

Gli3 represents an important control gene for development and differentiation of several body structures. For example, a reduction in gene dosage leads to severe perturbation, especially limb morphogenesis (Vortkamp et al., 1995 *DNA Cell Biol.* 14:629-34). Further, mutations in GLI3 have been identified in several human malformation syndromes, such as Greig cephalopolydactyly syndrome (GCPS) affecting limb and craniofacial development and the autosomal dominant form of Pallister-Hall syndrome. (Vortkamp et al., 1991, *Nature* 352:539-40; Bose et al., 2002, *Hum. Mol. Genet.* 11:1129-35). In the mouse, GLI3 mutations have been implicated in the mouse mutant extra toes.

GLI proteins function as transcriptional activators by binding via their zinc finger domains to a DNA binding site within a promoter and/or enhancer sequence of target genes. Recently, DNA binding sequences bound by GLI proteins were identified. For example, the DNA sequence bound by GLI3 zinc fingers consists of 16 nucleotides and shows a high degree of similarity to sequences bound by the GLI and tra-1 proteins (Vortkamp et al., 1995, *DNA Cell. Biol.* 14:629-34). This binding site included the 9-base-pair sequence 5'-GAC-CACCCA-3' previously identified for GLI protein binding (Kinzler and Vogelstein, 1990, *Mol. Cell. Biol.* 10:634-42). It is believed that GLI, GLI2, and GLI3 bind identical or similar DNA sequences (Yoon et al., 1998, *J. Biol. Chem.* 273:3496-3501). Recently, the 9 bp consensus sequence 5'-GACCAC-CCA-3' as a binding site for GLI1, GLI2, and GLI3 proteins was confirmed by Hallikas et al. (Hallikas et al, 2006, *Cell* 124:47-59).

Activation of Hh/GLI target genes by GLI2 and GLI3 proteins may require the transcriptional co-activator Creb Bing Protein (CBP), which binds to a CBP binding domain (see FIG. 1; Dai et al., 1999, *J. Biol. Chem.* 274:8143-52; Kasper, Regl, Frischauf and Aberger, 2006, *Eur. J. Cancer*)

GLI1 expression has been reported to be under control of GLI2 and GLI3 proteins Dai et al., 1999, *J. Biol. Chem.* 274:8143-52). While the whole GLI1 protein is a transcriptional activator, GLI2 and GLI3 contain both activator and repressor domains (see FIG. 1). GLI2 and GLI3 can be processed for different functions through the action of protein kinase A (PKA). Full-length GLI2 acts as a weak transcriptional activator. Truncation of the activation domain in the C-terminal half results in a protein with repressor activity, while removal of the repression domain at the N-terminus converts GLI2 into a strong activator. N-terminally truncated GLI2, unlike the full length protein, activates, for example a Sonic hedgehog (Shh) gene, HNF3beta, in transgenic mouse embryos. This suggested that unmasking the activation domain of GLI2 is one of the key mechanisms of the Shh signaling pathway. A similar regulatory mechanism involving the N-terminal region was also described for GLI3, but not for GLI. (Sasaki et al., 1999, *Development* 126:3915-24, incorporated by reference in its entirety).

A comparison of the murine and human GLI3 cDNA revealed an overall homology of 85% between the deduced amino acid sequences and an even higher conservation (<95%) in several domains, including the zinc fingers (Thien et al., 1996, *Biochim. Biophys. Acta* 1307:267-9).

Recently, a transcription activation domain for GLI was identified at the carboxy-terminus terminus which comprised amino acid residues 1020 to 1091. This domain includes an 18 amino acidic α-helix (amino acids 1037 to 1054) containing six aspartate or glutamate residues (Yoon et al., 1998, *J. Biol. Chem.* 273:3496-3501). This α-helical region is highly similar to the herpes simplex viral protein 16 (VP16) transcription activation domain, and includes the conserved motif FXXΦΦ (F=phenylalanine; X=any residue; Φ=any hydrophobic residue), described as a general recognition element of acidic activation domains for $TAF_{II}31$. In addition, conservation of the three amino acid residues ($Asp^{472}$, $Phe^{479}$, and $Leu^{483}$ in VP16, and $Asp^{1040}$, $Phe^{1048}$, and $Leu^{1052}$ in GLI)

that are believed to make direct contacts with the TBP-Associated Factor (TAF), $TAF_{II}31$, was found (Yoon et al., 1998, *J. Biol. Chem.* 273:3496-3501; Goodrich et al., 1993, *Cell* 75:519-530; Klemm et al., 1995, *Proc. Natl. Acad. Sci. USA* 92:5788-5792; Uesugi et al., 1997, *Science* 277:1310-1313).

A similar domain is present in the other GLI family proteins. For example, putative $TAF_{II}31$ binding domains were described and include $NH_2$-INKDNLRKDLFTVSIKA-COOH (*Drosophila* Ci, amino acid residues 1044-1060), $NH_2$-DMADFEFEQMFTDALGI-COOH (VP16, amino acid residues 469-485), $NH_2$-DSLDLDNTQLDFVAILDE-COOH (human GLI, amino acid residues 1037-1054), $NH_2$-DSLDLDNTQLDFVAILDE-COOH (mouse GLI, amino acid residues 1040-1057), $NH_2$-DSHDLEGVQIDFDAIIDD-COOH (human GLI3, amino acid residues 1495-1512), and $NH_2$-DSQLLEPPQIDFDAIMDD-COOH (mouse GLI2, amino acid residues 1509-1526). (Yoon et al., 1998, *J Biol. Chem.* 273:3496-3501). In addition, putative $TAF_{II}31$ interaction domains of human GLI2, $NH_2$-DSQLLEAPQIDFDAIMDD-COOH (amino acid residues 1501-1518) can be identified, e.g., from GenBank Accession No. AAY87165. Further, the putative $TAF_{II}31$ interaction domain of mouse GLI3, $NH_2$-ESHDLEGVQIDFDAIIDD-COOH (amino acid residues 1497-1514) can be identified from, e.g., GenBank Accession No. Q61602. The conserved amino acid residues for contacting $TAF_{II}31$ are indicated in bold and underlined.

Though much is known about Hh-signaling in *Drosophila* and murine development, understanding of the molecular mechanisms and tumorigenic programs that are activated in response to Hh-signaling and GLI-activity in human cancer is still very limited. A common property of Hh-associated cancers is the elevated expression level of one or more GLI proteins. For example, recently, overexpression of GLI1 was found in a number of cancer types, including prostate, pancreas and small-cell lung cancer (Karhadkar et al., 2004, *Nature* 431:707-12). In addition, Gli was found to be amplified in childhood sarcomas and more than 50-fold in a malignant glioma (Roberts et al., 1989, *Cancer Res.* 49:5407-13; Kinzler et al., 1987, *Science* 236:70-3). Although Hedgehog (Hh) and its receptor Patched (Ptch) have also been found to be overexpressed in non small-cell lung cancer (NSCLC), no GLI1 expression was found in this type of cancer.

Overexpression of GLI2, for example, has been found in basal cell carcinoma (BCC) lesions compared to normal skin (Ikram et al., 2004, *J. Invest Dermatol.* 122:1503-9; Regl et al., 2002, *Oncogene* 21:5529-39; Hutchin et al., 2005, *Genes Dev.* 19:214-23). In addition, based on the processing of GLI2 and GLI3, GLI2 and/or GLI3 might be more important in activation of Hh signaling during tumorigenesis for many types of cancer, including lung cancer and prostate cancer.

Lung Cancer is the leading cause of cancer death in the United States and worldwide, with >170,000 newly diagnosed cases each year in the United States and nearly a million cases worldwide (Minna et al., 2002, *Cancer Cell.* 1(1): 49-52). Despite aggressive approaches made in the therapy of lung cancer in the past decades, the 5-year survival rate for lung cancer remains under 15%. Lung cancers are divided into two groups: non-small-cell lung cancer (NSCLC) and small-cell lung cancer (SCLC). NSCLC (75-80% of all cancers) consists of three major types: adenocarcinoma, squamous cell carcinoma, and large cell carcinoma (Minna et al., 2002, *Cancer Cell.* 1(1):49-52). Lung carcinomas and squamous cell carcinomas represent 60-70% of all lung cancers. Surgery, chemotherapy, and radiation have been used with generally unsatisfactory results in advanced disease. Improvement in the efficacy of lung cancer treatment is a major public health goal.

Prostate cancer may be the most common solid tumor in men (Nelson et al., 2003, *N. Engl. J Med.* 349:366-381). For example, 50% of all men over 50, and essentially all men over 70 suffer from some form of prostate hyperplasia. In the United States, prostate cancer is the most frequently diagnosed cancer, with over 250,000 new cases being diagnosed each year. 40,000 men die every year due to prostate cancer.

Thus, given the broad spectrum of frequent and lethal malignancies involving Hh/GLI-signaling, specific targeting of the Hh/GLI-signaling pathway may offer a highly effective therapeutic strategy for the treatment of a variety of lethal tumors (Pasca di Magliano and Hebrok, 2003, *Nat. Rev. Cancer* 3:903-911; Sanchez et al., 2005, *Cancer Res.* 65:2990-2; Kasper, Regl, Frischauf and Aberger, 2006, *Eur. J Cancer*). Treatment of human diseases resulting from ectopic Hh or GLI signaling pathway activation may require the use of pathway antagonists. Up to now, inhibition of ectopic activity has been achieved by treatment with signaling antagonists that block the pathway at different levels. For example, anti-Shh antibodies act extracellularly and the plant alkaloid, cyclopamine, acts at the level of Smo in the cell membrane (e.g., see U.S. Pat. Appl. No. 2005/0130922 A1; Taipale et al., 2000, *Nature* 406:1005-9; Sanchez and Ruiz I Altaba, 2005, *Mech. Dev.* 122(2):223-30; Athar et al., 2004, *Cancer Res.* 64(20):7545-52). Small molecule modulators of hedgehog signaling and binding to Smo were described, including a synthetic non-peptidyl small molecule, Hh-Ag (Frank-Kamenetsky et al., 2002, *J. Biol.* 1(2):10), HhAntag (Romer et al., 2004, *Cancer Cell.* 6(3):229-40), and Cur61414 (Williams et al., 2003, *Proc. Natl. Acad. Sci. USA* 100(8):4616-21). In addition, forskolin has been used to intracellularly activate protein kinase A (PKA), which is a cytoplasmic inhibitor of the GLI signaling pathway. However, these approaches have disadvantages. For example, administration of therapeutically effective amounts of anti Shh antibodies is difficult to achieve and may affect other normal pathway dependent cells in the patient. Cyclopamine, which is very expensive, may only be useful to treat disease that arise through activation of the Hh signaling pathway at the level of Smo or above. Further, because of the wide-spread activity of PKA, administration of forskolin may lead to numerous side effects. In contrast thereto, the use of small molecule compounds that inhibit GLI signaling holds great promise.

The inventors address a great and unfulfilled need in treating cancers wherein GLI proteins, and in particular GLI3, are overexpressed. The present invention provides small molecule compounds, pharmaceutical compositions, kits and methods useful for the detection and treatment of a number of cancers wherein GLI3 protein is overexpressed. Such cancers include lung cancer, NSCLC, breast cancer, colon cancer, mesothelioma, melanoma, sarcoma, prostate cancer, ovarian cancer, renal cancer, esophageal cancer, gastric cancer, hepatocellular cancer, nasopharyngeal cancer, pancreatic cancer, glioma, and others.

BRIEF SUMMARY OF THE INVENTION

In the present invention, the inventors have found that the activator domain of GLI3 protein (approximately 70 kDa) is overexpressed in various human cancer cell lines, including lung cancer, NSCLC, breast cancer, colon cancer, mesothelioma, melanoma, sarcoma, prostate cancer, ovarian cancer, renal cancer, esophageal cancer, gastric cancer, hepatocellular cancer, nasopharyngeal cancer, pancreatic cancer, glioma, and others. Overexpression of GLI3 was also found in metastasized colon and sarcoma tissue samples (>95%).

Thus, the inventors propose that inhibition of the active form of the GLI3 protein in these cancers, but not in normal cells, induces significant apoptosis. Inhibition of GLI3 protein signaling can be achieved by different means, including but not limited to (i) direct inhibition of the transcriptional activity of GLI3 protein, (ii) inhibition of the processing of the GLI3 precursor protein, (iii) inhibition of phosphorylation of the GLI3 activator domain, or (iv) inhibition of any of the cellular proteins involved in the process of generating the active GLI3 protein. Inhibition of GLI3 protein signaling can be accomplished by various means, for example by using small molecule compounds, siRNA, peptides, or antisense oligonucleotides. This invention provides small molecule compounds for inhibiting GLI protein signaling and in particular GLI3 protein signaling.

In one embodiment, the present invention provides a small molecule compound of the formula:

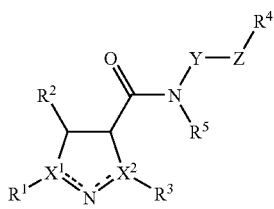

wherein each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C. Additionally, each of $R^1$, $R^2$ and $R^3$ is independently selected from the group consisting of $C_1$-$C_6$ alkyl, aryl, heteroaryl, cycloalkyl and heterocycloalkyl, optionally substituted with 0-3 $R^6$ groups each independently selected from the group consisting of H, halogen, $C_1$-$C_6$ alkyl, —$OR^7$, —$C(O)R^7$, —$OC(O)R^7$, —$N(R^7,R^7)$, —$NR^7S(O)_2R^7$, —$C(O)N(R^7,R^7)$, —$N(R^7)C(O)R^7$, —$N(R^7)C(O)N(R^7,R^7)$, —$C(NR^7)N(R^7,R^7)$, —$N(R^7)C(NR^7)N(R^7,R^7)$ and $S(O)_mR^7$ wherein subscript m is 0, 1 or 2. Y is a direct bond or $C_1$-$C_4$ alkyl, and Z is a member selected from the group consisting of $C_1$-$C_4$ alkyl, aryl and heteroaryl. $R^4$ is H, halogen, —$OR^7$, —$OC(O)R^7$, —$C(O)OR^7$, —$N(R^7,R^7)$, —$NR^7S(O)_2R^7$, —$C(O)N(R^7,R^7)$, —$N(R^7)C(O)N(R^7,R^7)$, —$C(NR^7)N(R^7,R^7)$ and $S(O)_mR^7$ wherein subscript m is 0, 1 or 2. $R^5$ is H, $C_1$-$C_6$ alkyl, or optionally combined with Y to form a 5 to 6 membered heterocycle. Each $R^7$ is independently H or $C_1$-$C_6$ alkyl.

In addition, the salts, hydrates, solvates, isomers and prodrugs of the small molecule compounds of the present invention are also contemplated.

In another embodiment, the present invention provides a small molecule compound of the formula where each of $R^1$, $R^2$ and $R^3$ is aryl. In a further embodiment, each of $R^1$, $R^2$ and $R^3$ is phenyl.

In another embodiment, the present invention provides a small molecule compound of the formula where $R^4$ is hydroxy. In another embodiment, Z is $C_1$-$C_4$ alkyl. In still another embodiment, Z is aryl. In yet another embodiment, Z is phenyl.

In a further embodiment, the present invention provides a small molecule compound of the formula where each of $R^1$, $R^2$ and $R^3$ is phenyl, where Y is $C_1$-$C_4$ alkyl, where Z is $C_1$-$C_4$ alkyl or phenyl, and where $R^4$ is hydroxy.

In another embodiment, the present invention provides a small molecule compound of the formula where $X^1$ is C and $X^2$ is N. In yet another embodiment, the small molecule compound of the formula has the following structure:

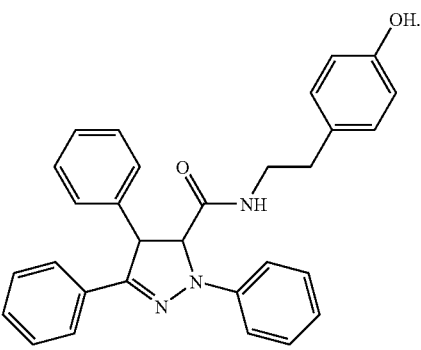

In still another embodiment, the small molecule compound of the formula has the following structure:

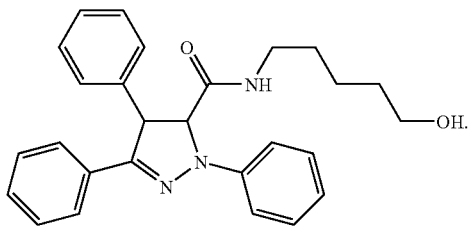

In other embodiments, the present invention provides a small molecule compound of the formula where $X^1$ is N and $X^2$ is C. In another embodiment, the small molecule compound of the formula has the following structure:

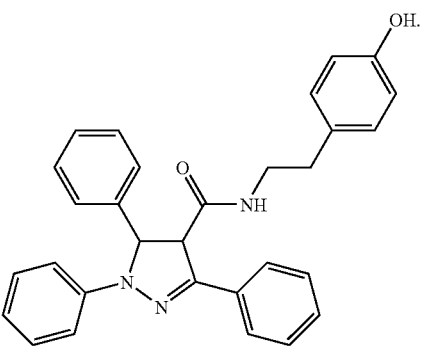

In still another embodiment, the small molecule compound of the formula has the following structure:

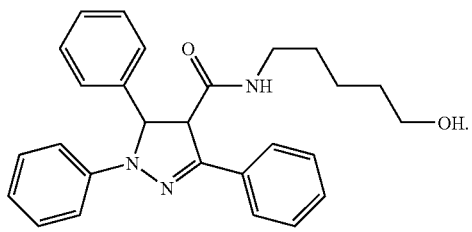

The present invention also provides pharmaceutical compositions and medicaments. Thus, in a further embodiment, the present invention provides a pharmaceutical composition comprising a small molecule compound of the present invention, and a pharmaceutically acceptable carrier.

The present invention also provides methods for using the small molecule compounds of the invention. In one aspect of the invention, a method for inducing a tumor cell expressing a GLI protein to undergo apoptosis is provided. This method comprises the step of contacting the tumor cell with a small molecule compound of the invention in a sufficient amount, wherein the step of contacting results in inducing apoptosis in the tumor cell. Preferably, the GLI protein is GLI2 or GLI3.

In one embodiment of this method, the small molecule compound is administered as part of a cancer treatment regimen.

In another aspect of the present invention, a method for inhibiting at least one of unwanted growth, hyperproliferation, or survival of a cell is provided. This method comprises the step of determining whether the cell expresses a Gli gene or alternatively a GLI protein. This method further comprises the step of contacting the cell with an effective amount of a small molecule of the present invention, wherein the step of contacting results in the inhibition of at least one of unwanted growth, hyperproliferation, or survival of the cell.

A cell or tumor cell useful in the methods of the present invention is selected from the group consisting of colon cancer, melanoma, mesothelioma, lung cancer, renal cell carcinoma, breast cancer, prostate cancer, sarcoma, ovarian cancer, esophageal cancer, gastric cancer, hepatocellular cancer, nasopharyngeal cancer, pancreatic cancer, and glioma cell.

Methods of the present invention can be practiced in vitro or in vivo. Thus, in another aspect of the present invention, a method for treating a subject suffering from a cancerous condition is provided. This method comprises the step of administering to the subject a therapeutically effective amount of a small molecule compound, wherein the cancerous condition is characterized by expressing a GLI polypeptide, preferably a GLI3 polypeptide and wherein the step of administering results in the treatment of the subject.

In another preferred embodiment of the present invention, a method for inhibiting the activity of a GLI protein in a cell is provided. This method comprises the step of contacting the cell with a small molecule compound of the present invention, wherein the step of contacting results in the inhibition of the activity of the GLI protein in the cell. A preferred GLI protein activity that is inhibited is a protein-protein interaction between a GLI protein and a cellular protein or a nuclear protein. A preferred nuclear protein is a TAF protein, a TATA-Box Binding Protein Associated Factor, preferably a $TAF_{II}31$ protein.

Further, the present invention provides a method for inhibiting the expression of a gene having a GLI DNA binding site operably linked to the promoter of the gene. This method comprises the step of contacting a cell expressing the gene having a GLI DNA binding site operably linked to its promoter with a small molecule compound of the present invention, wherein the step of contacting results in inhibition of expression of the gene. In a preferred embodiment of the present invention, the gene is a Wnt2 gene and preferably a human Wnt2 gene.

Further, the present invention provides for the use of a small molecule compound of the present invention in the manufacture of a medicament for inhibiting at least one of unwanted growth, hyperproliferation, or survival of a cell. In another aspect, a use of a small molecule compound in the manufacture of a medicament for treatment of a cancer is provided. In yet another embodiment, the present invention provides for the use of a small molecule compound in the manufacture of a medicament for inducing apoptosis in a cell. In another aspect, use of a small molecule compound of the present invention in the manufacture of a medicament for inhibiting GLI protein signaling in a cell is provided.

In yet another aspect, the present invention provides screening methods. A preferred method of this invention is a method for identifying a candidate compound capable of inhibiting the protein-protein interaction between a GLI protein and a $TAF_{II}31$ protein. In one embodiment, this method comprises the steps of contacting a candidate compound with a sample comprising a GLI protein and a $TAF_{II}31$ protein; and determining the binding of the GLI-protein to the $TAF_{II}31$ protein. A reduced binding of the GLI protein to the $TAF_{II}31$ in the presence of the candidate compound compared to the binding of the GLI protein to the $TAF_{II}31$ in the absence of the candidate compound indicates that the candidate compound is capable of inhibiting the interaction between the GLI protein and the $TAF_{II}31$ protein.

Another method provided herein is a method for identifying a compound that modulates a GLI protein activity. In one embodiment, the GLI protein activity is GLI protein dependent transcription activity and the method is for identifying a compound that modulates GLI protein dependent transcription activity. The method comprises the steps of contacting a sample with a candidate compound, wherein the sample comprises an expression reporter construct having one or more GLI DNA binding sites operably linked to a reporter gene; and determining the effect, if any, of the candidate compound on the level of GLI protein dependent transcription activity.

DETAILED DESCRIPTION OF THE INVENTION

I. Definitions

Figure 1:
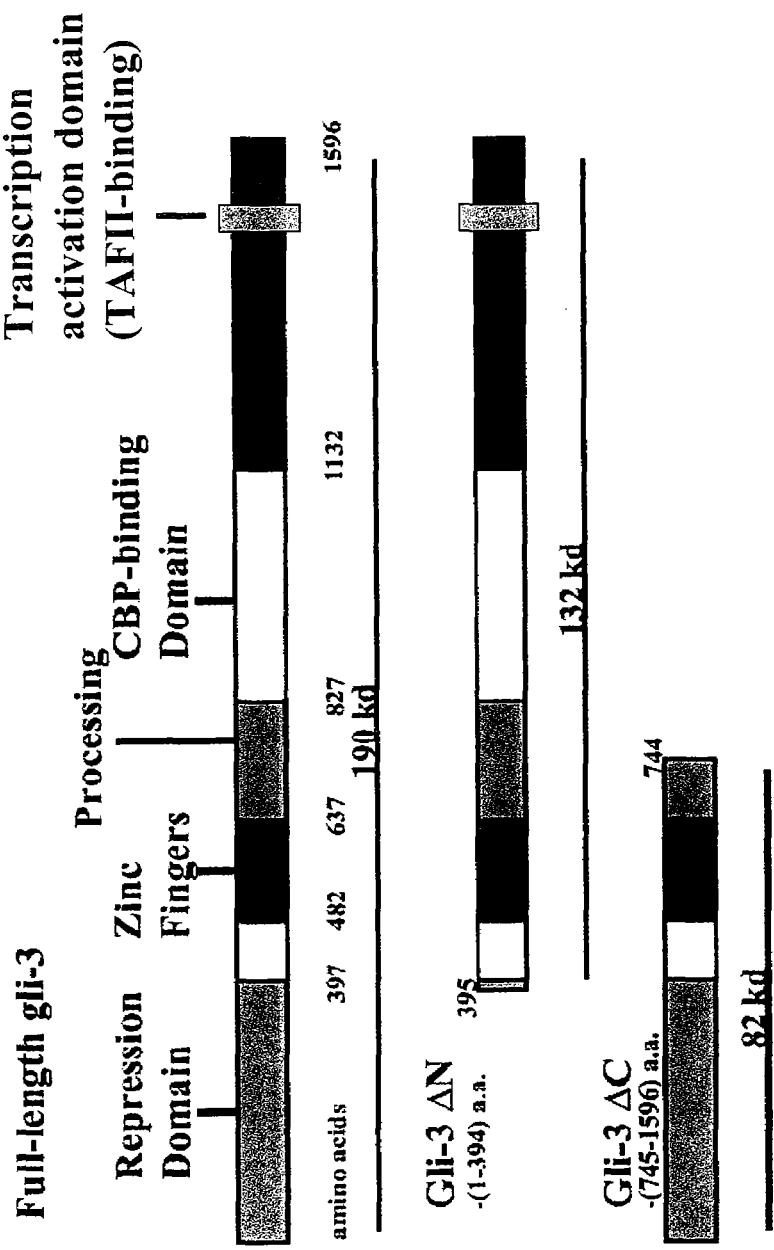
FIG. 1 shows the location of the transcription activation domain of GLI3. The GLI3 transcription activation domain is located near the C-terminus and contains a conserved VP16-like activating region ($TAF_{II}31$ binding domain), and is necessary for the activator function of GLI3, but not for the repressor function of GLI3. This FXXΦΦ motif is thought to contact $TAF_{II}31$ directly. In GLI3, this domain has the amino acid sequence FDAII.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "alkyl" refers to a straight or branched chain hydrocarbon radical, and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

As used herein, the term "alkenyl" refers to an unsaturated alkyl group one having one or more double bonds. Examples of alkenyl groups include vinyl, 2-propenyl, crotyl, 2-isopentenyl, 2-(butadienyl), 2,4-pentadienyl and 3-(1,4-pentadienyl), and the higher homologs and isomers.

As used herein, the term "alkynyl" refers to an unsaturated alkyl group one having one or more triple bonds. Examples of alkynyl groups include ethynyl (acetylenyl), 1-propynyl, 1- and 2-butynyl, and the higher homologs and isomers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to a compound that has the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. "Amino acid mimetic" refers to a chemical compound that has a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "aryl" refers to a polyunsaturated, aromatic, hydrocarbon substituent having 5-12 ring members, which can be a single ring or multiple rings (up to three rings) which are fused together or linked covalently. Non-limiting examples of aryl groups include phenyl, 1-naphthyl, 2-naphthyl, 4-biphenyl, and benzyl. Other aryl groups are also useful in the present invention.

"Biological sample" as used herein is a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the present invention, including, but not limited to, a tissue biopsy, a blood sample, a buccal scrape, a saliva sample, or a nipple discharge. As used herein, a "tissue biopsy" refers to an amount of tissue removed from an animal, preferably a human, for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, will be particularly useful.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of basic Technique* (3rd ed. 1994)).

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

"Correlating the amount" means comparing an amount of a substance, molecule or marker (such as Gli or GLI) that has been determined in one sample to an amount of the same substance, molecule or marker determined in another sample. The amount of the same substance, molecule or marker determined in another sample may be specific for a given cancer.

Synonyms of the term "determining the amount" are contemplated within the scope of the present invention and include, but are not limited to, detecting, measuring, testing or determining, the presence, absence, amount or concentration of a molecule, such as Gli or GLI.

As used herein, the term "cycloalkyl" refers to a saturated cyclic hydrocarbon having 3 to 15 carbons, and 1 to 3 rings that can be fused or linked covalently. Cycloalkyl groups useful in the present invention include, but are not limited to, cyclopentyl, cyclohexyl, cycloheptyl and cyclooctyl. Bicycloalkyl groups useful in the present invention include, but are not limited to, [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth.

As used herein, the term "cycloalkenyl" refers to an unsaturated cyclic hydrocarbon having 3 to 15 carbons, and 1 to 3 rings that can be fused or linked covalently. Cycloalkenyl groups useful in the present invention include, but are not limited to, cyclopentenyl, cyclohexenyl, cycloheptenyl and cyclooctenyl. Bicycloalkenyl groups are also useful in the present invention.

By "determining the functional effect" is meant assaying for a compound that increases or decreases a parameter that is indirectly or directly under the influence of a GLI protein, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the GLI protein; measuring binding activity, e.g., binding to a TAF protein (e.g., $TAF_{II}31$), measuring cellular proliferation, measuring apoptosis, or the like. Determination of the functional effect of a compound, e.g., a small molecule compound, on cancer can also be performed using assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of cancer cells. The functional effects can be evaluated by many means known to those skilled in the art, e.g., microscopy for quantitative or qualitative measures of alterations in morphological features, measurement of changes in Gli RNA or protein levels, measurement of RNA stability, identification of downstream or reporter gene expression (CAT, luciferase, β-gal, GFP and the like), e.g., via chemiluminescence, fluorescence, colorimetric reactions, antibody binding, inducible markers, and ligand binding assays. "Functional effects" include in vitro, in vivo, and ex vivo activities.

Synonyms of the term, "determining" are contemplated within the scope of the present invention and include, but are not limited to, detecting, measuring, assaying, testing or determining, the presence, absence, amount or concentration of a molecule, such as a GLI polypeptide, a label, a small molecule compound of the invention. The term refers to both qualitative and quantitative determinations.

The terms "down-regulate" or "inhibiting" in the context of Shh signaling, GLI signaling, or Wnt2 signaling refers to partially or totally block Shh signaling, GLI signaling, or Wnt2 signaling as measured by known assays for Shh signaling, GLI signaling, or Wnt2 signaling. Inhibitors, for example, are small molecule compounds of the present invention.

An "effective amount", "effective dose", "sufficient amount" or grammatical equivalents thereof of a small molecule compound of the present invention for treatment is an amount that is sufficient to ameliorate, or in some manner, reduce a symptom or stop or reverse progression of a condition. Amelioration of a symptom of a particular condition, e.g., cancer, by administration of a particular pharmaceutical composition refers to any lessening, whether permanent or temporary, lasting or transit that can be associated with the administration of the pharmaceutical composition. An "effective amount" can be administered in vivo and in vitro.

An "expression vector" or "expression construct" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "GLI" refers to a family of GLI proteins. GLI proteins include GLI (also referred to as GLI1), GLI2, and GLI3. A preferred GLI protein is GLI1, GLI2, or GLI3.

The term "Gli" refers to a gene encoding a GLI protein. Thus, Gli1, Gli2, and Gli3 are genes encoding a GLI1, GLI2 and GLI3 protein, respectively.

The term "GLI protein activity" refers to GLI signaling and includes, for example, transcriptional activation of a downstream gene by GLI, binding of GLI protein to a GLI DNA binding site, and binding of GLI protein to other proteins, e.g., a TAF or to co-activators, such as CBP (Creb Protein Binding Protein).

The term "GLI DNA binding site" refers to a nucleotide sequence to which a GLI protein binds and from which it can activate gene transcription. GLI DNA binding sites were described by, e.g., Vortkamp et al. (1995, *DNA Cell. Biol.* 14:629-34) Kinzler and Vogelstein (1990, *Mol. Cell. Biol.* 10:634-42) and Yoon et al. (998, *J Biol Chem* 273:3496-3501). A GLI DNA binding site bound by GLI3 zinc fingers, described by Vortkamp et al. (1995, *DNA Cell. Biol.* 14:629-34), for example, consists of 16 nucleotides and shows a high degree of similarity to sequences bound by the GLI and tra-1 proteins. This binding site included the 9-base-pair sequence 5'-GACCACCCA-3'. It is understood that a GLI3 DNA binding site need not be 100% identical to the GLI DNA binding site identified by Vortkamp et al. (1995, *DNA Cell. Biol.* 14:629-34). For example, recently, Hallikas et al. determined the DNA binding specificities of GLI1, GLI2, and GLI3 and also found GLI binding to, for example, 5'-TACCAACCCA-3', 5'-GCCCACCCA-3', 5'-GGCCACCCA-3', and 5'-GATCACCCA-3', wherein the underlined nucleotide indicates a difference to the 9 bp consensus sequence (Hallikas et al., 2006, *Cell* 124(1):47-59; incorporated by reference in its entirety). Assays to determine binding of a GLI protein to a GLI DNA binding site are known in the art and include, e.g., electrophoretic mobility shift assays (EMSA; Fried and Crothers, 1981, *Nucleic Acids Res.* 9:6505-6525; Hallikas et al., 2006, *Cell* 124:47-59) SELEX (Roulet et al., 2002 Nat. *Biotechnol.* 20:831-835), and chromatographic binding assays.

A "GLI" polypeptide includes both naturally occurring or recombinant forms. Therefore, in some embodiments, a GLI polypeptide and a GLI subdomain polypeptide as described herein can comprise a sequence that corresponds to a human GLI sequence. Thus, exemplary GLI are provided herein and are known in the art. For example, several vertebrate GLI1, GLI2, and GLI3 proteins have been characterized, for example, human GLI1 (GenBank Accession Nos. NM_005269, P08151), mouse GLI1 (GenBank Accession Nos. NM_010296, AB025922, AAC09169, P47806), zebrafish GLI1 (GenBank Accession No. NM_178296), human GLI2 (GenBank Accession Nos. NM_030381; NM_030380; NM-030379, DQ086814), mouse GLI2 (GenBank Accession No.XM_922107), human GLI3 (GenBank Accession Nos. NM_000168, AJ250408, M57609, P10071, AAY87165), chimpanzee GLI3 (GenBank Accession Nos. NM_001034190, AY665272, Q5IS56), mouse GLI3 (GenBank Accession Nos. X95255, NM_008130, NP_032156, Q61602), rat GLI3 (GenBank Accession No. XM_225411), zebrafish GLI3 (GenBank Accession Nos. NM_205728, AY377429).

A GLI protein may be a full-length GLI protein or it may be a partial GLI protein, such as a subdomain of a GLI protein. For example, a "GLI3" polypeptide refers to a polypeptide and polymorphic variants, alleles, mutants of human GLI3 that: (i) has an amino acid sequence that has greater than about 60% amino acid sequence identity, 65%, 70%, 75%, 80%, 85%, 90%, preferably 91%, 92%, 93%, 94%, 95%, 96%, 97%, 98% or 99% amino acid sequence identity, preferably over a region of at least about 100, 150, 200, 250, 300, 500 or more amino acids, to a human GLI3 selected from GenBank Accession Nos. NM_000168, AJ250408, M57609, P10071, and AAY87165), (ii) comprises the amino acid motif FXXΦΦ (F=phenylalanine; X=any residue; Φ=any hydrophobic residue; preferably the amino acid sequence FDAII, (iii) comprises a transcription activation domain, (iv) binds to a GLI DNA binding site and/or (v) binds to a TAF.

A "Gli nucleic acid" or "gli polynucleotide" refers to a vertebrate gene encoding a GLI, GLI2, or GLI3 protein. A "Gli nucleic acid" includes both naturally occurring or recombinant forms. A Gli polynucleotide or GLI polypeptide encoding sequence is typically from a human, but may be from other mammals, but not limited to, a non-human primate, a rodent, e.g., a rat, mouse, or hamster; a cow, a pig, a horse, a sheep, or other mammal. Gli nucleic acids useful for practicing the present invention, have been cloned and characterized, for example, human Gli1 (GenBank Accession Nos. NM_005269), mouse Gli1 (GenBank Accession Nos. NM_010296, AB025922), zebrafish Gli1 (GenBank Accession No. NM_178296), human Gli2 (GenBank Accession Nos. NM_030381; NM_030380; NM-030379, DQ086814), mouse Gli2 (GenBank Accession No.XM_922107), human Gli3 (GenBank Accession Nos. NM_000168, AJ250408, M57609), chimpanzee Gli3 (GenBank Accession Nos. NM_001034190, AY665272), mouse Gli3 (GenBank Accession Nos. X95255, NM_008130), rat Gli3 (GenBank Accession No. XM_225411), zebrafish Gli3 (GenBank Accession Nos. NM_205728, AY377429). A Gli polynucleotide may be a full-length Gli polynucleotide, i.e., encoding a complete GLI protein or it may be a partial Gli polynucleotide encoding a subdomain of a GLI protein.

The terms "GLI pathway", "GLI signaling" or "GLI signaling pathway" are used interchangeably and refer to the signaling pathway initiated by a hedgehog protein binding to its receptor(s) leading to the expression and/or activity of a GLI protein.

As used herein, the term "halogen" refers to the elements including fluorine (F), chlorine (Cl), bromine (Br) and iodine (I).

The term "hedgehog" is used interchangeably with the term "Hh" and is a cytokine that binds to a Hh receptor thereby initiating the Hh signaling pathway leading to the expression or activation of GLI proteins. There are three Hh family genes in mammals, Sonic hedgehog (Shh), Indian hedgehog (Ihh), and Desert hedgehog (Dhh). Several vertebrate hedgehog proteins are known in the art, for example, human SHH, murine SHH, rat SHH, human IHH, and murine DHH.

As used herein, the term "heteroaryl" refers to a polyunsaturated, aromatic, hydrocarbon substituent having 5-12 ring members, which can be a single ring or multiple rings (up to three rings) which are fused together or linked covalently, and which has at least one heteroatom in the ring, such as N, O, or S. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. Additional heteroaryl groups useful in the present invention include pyridyl N-oxide, tetrazolyl, benzofuranyl, benzothienyl, indazolyl, or any of the radicals substituted, especially mono- or di-substituted.

As used herein, the term "heterocycloalkyl" refers to a saturated cyclic hydrocarbon having 3 to 15 ring members, and 1 to 3 rings that can be fused or linked covalently, and which has at least one heteroatom in the ring, such as N, O, or S. Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

As used herein, the term "isomers" refers to compounds of the present invention that possess asymmetric carbon atoms (optical centers) or double bonds. The racemates, diastereomers, geometric isomers and individual isomers are all intended to be encompassed within the scope of the present invention.

A "label" or a "detectable moiety" is a composition detectable by spectroscopic, photochemical, biochemical, immunochemical, chemical, or other physical means. For example, useful labels include $^3$H, $^{125}$I, $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a small molecule compound. The labels may be incorporated into a small molecule compound at any position.

The terms "level of Gli MRNA" or "level of Wnt2 mRNA" in a biological sample refer to the amount of mRNA transcribed from a Gli or Wnt gene, respectively, that is present in a cell or a biological sample. The mRNA generally encodes a functional GLI or WNT protein, although mutations may be present that alter or eliminate the function of the encoded protein. A "level of Gli mRNA" or "level of Wnt2 mRNA" need not be quantified, but can simply be detected, e.g., a subjective, visual detection by a human, with or without comparison to a level from a control sample or a level expected of a control sample.

The "level of GLI polypeptide" or "level of Wnt2 polypeptide" in a biological sample refers to the amount of polypeptide translated from a Gli or Wnt2 mRNA, respectively, that is present in a cell or biological sample. The polypeptide may or may not have GLI or WNT2 protein activity. A "level of GLI polypeptide" or "WNT2 polypeptide" need not be quantified, but can simply be detected, e.g., a subjective, visual detection by a human, with or without comparison to a level from a control sample or a level expected of a control sample.

As used herein a "modulator" of the level or activity of a polypeptide, such as a GLI includes an activator and/or inhibitor of that polypeptide and is used to refer to compounds that activate or inhibit the level of expression of the polypeptide or the activity of the polypeptide. Preferred polypeptides are GLI1, GLI2, or GLI3. Activators are compounds that, e.g., induce or activate the expression of a polypeptide of the invention or bind to, stimulate, increase, open, activate, facilitate, or enhance activation, sensitize or up regulate the activity of a polypeptide of the invention. Activators include naturally occurring and synthetic compounds, small chemical molecules and the like. Assays for activators include, e.g., applying candidate compounds to cells expressing a GLI polypeptide and then determining the functional effects. Samples or assays comprising a GLI polypeptide that are treated with a potential activator are compared to control samples without the activator to examine the extent of effect. Control samples (untreated with candidate compounds) are assigned a relative activity value of 100%. Activation of the polypeptide is achieved when the polypeptide activity value relative to the control is 110%, optionally 130%, 150%, optionally 200%, 300%, 400%, 500%, or 1000-3000% or more higher. Inhibitors are compounds that, e.g., repress or inactivate the expression of a polypeptide of the invention or bind to, decrease, close, inactivate, impede, or reduce activation, desensitize or down regulate the activity of a polypeptide of the invention. Inhibitors include nucleic acids such as siRNA and antisense RNA that interfere with the expression of a GLI protein, as well as naturally occurring and synthetic compounds, small chemical molecules and the like. Assays for inhibitors are described herein. Samples or assays comprising a GLI polypeptide that are treated with a potential inhibitor are compared to control samples without the inhibitor to examine the extent of effect. Control samples (untreated with candidate compounds) are assigned a relative activity value of 100%. Inhibition of the polypeptide is achieved when the polypeptide activity value relative to the control is reduced by 10%, optionally 20%, optionally 30%, optionally 40%, optionally 50%, 60%, 70%, 80%, or 90-100%.

The term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

As used herein, the term "prodrug" refers to compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

By "resistant to chemotherapeutic agents" herein is meant a tumor that does not respond to treatment with a chemotherapeutic agent, i.e., is not killed by, or growth-inhibited by, such treatment.

As used herein, the term "salts" refers to salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "solvates" refers to compounds of the present invention that are complexed to a solvent. Solvents that can form solvates with the compounds of the present invention include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

The terms "subject" or "patient" refer to a mammal, preferably a human, in need of treatment for a condition, such as cancer, disorder, or disease.

The term "TAF" refers to a TBP-associated factor. Preferably the TAF is a $TAF_{II}$, i.e., a TAF protein involved in mediating transcriptional activation of a eukaryotic gene transcribed by RNA polymerase II. A TAF protein interacts with other transcriptional activators or repressors (Goodrich and Tjian, *Curr Opin Cell Biol* 6(3):403-9 (1994); Albright and Tjian, *Gene* 242 (1-2):1-13 (2000)). A TAF is preferably from human, mouse, *Drosophila* or yeast. A preferred TAF protein interacting with a GLI is a $TAF_{II}31$ protein. Klemm et al. cloned a human TFIID subunit, which they termed $hTAF_{II}32$ (Klemm et al. 1995, *Proc Natl Acad Sci USA*, 92(13):5788-92). The 32-kD protein was isolated from HeLa cell nuclear extracts and partially sequenced. The identified cDNA has a deduced amino acid sequence of 264 residues and is related to the Drosophila $TAF_{II}40$. Klemm et al. showed that $TAF_{II}32$ interacts with GTF2B and with the viral transcriptional trans-activator VP 16 (Klemm et al. 1995, *Proc Natl Acad Sci USA*, 92(13):5788-92). The authors showed that recombinantly expressed $TAF_{II}32$ was functional in a partial recombinant $TF_{II}D$ complex and that the recombinant complex mediated activation by a GAL4-VP16 fusion protein. $TAF_{II}32$ and $TAF_{II}31$ are two names for the same protein, which is nowadays also referred to as TAF9. Lu et al. cloned TAF9, which they called $TAF_{II}31$. TAF9 encodes a 264-amino acid protein. Immunoprecipitation and binding analyses showed interaction of TAF9 with the N-terminal domain of p53 at sites identical to those bound by MDM2, the major cellular negative regulator of p53 activity. (Lu et al., 1995, *Proc Natl Acad Sci USA*, 92(11):5154-8). Human $TAF_{II}31$ nucleotide and protein sequences can be found, e.g., at GenBank accession numbers U25112, U21858, and NM_016283.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Treatment means any manner in which the symptoms or pathology of a condition, disorder, or disease are ameliorated or otherwise beneficially altered. Preferably, the subject in need of such treatment is a mammal, more preferable a human.

"Tumor cell" refers to precancerous, cancerous, and normal cells in a tumor.

The terms "Wnt" refer to a family of mammalian genes and encoded proteins related to the *Drosophila* segment polarity gene, wingless. In humans, the Wnt family of genes typically encode 38 to 43 kDa cysteine rich glycoproteins having hydrophobic signal sequence, and a conserved asparagine-linked oligosaccharide consensus sequence (Shimizu et al., *Cell Growth Differ* 8(12):1349-58 (1997)). The Wnt family contains at least 19 mammalian members. Exemplary Wnt proteins include Wnt1, Wnt2, Wnt3, Wnt3A, Wnt4, Wnt5A, Wnt5B, Wnt6, Wnt7A, Wnt7B, Wnt8A, Wnt8B, WNT10A, Wnt10B, Wnt11, Wnt12, Wnt13, Wnt14, Wnt15, and Wnt16. A preferred Wnt protein of the invention is Wnt2, preferably a human Wnt2 protein.

II. Small Molecule Compounds

A. Selection of GLI3 Target Sequence

Transcriptional activation domains share little sequence homology and generally lack a folded structure in the absence of their target binding proteins. As described herein, GLI, GLI2, and GLI3 are believed to contact the TBP-associated factor, $TAF_{II}31$, through an α-helical domain found within their transcriptional activation domain (see FIG. 3). In one aspect of the present invention it is realized that while the GLI, GLI2 and GLI3 transcriptional activation domains are individually well conserved among different species, they are quite different among themselves. For example, the transactivation domains human GLI1, NH$_2$-DSLDLDNTQLD-FVAILDE-COOH (human GLI1, amino acid residues 1037-1054), and mouse GLI1, NH$_2$-DSLDLDNTQLDFVAILDE-COOH (mouse GLI1, amino acid residues 1040-1057), are identical. Further, the transactivation domains of human and GLI2, NH$_2$-DSQLLEAPQIDFDAIMDD-COOH (amino acid residues 1501-1518), and mouse GLI2, NH$_2$-DSQLLE PPQIDFDAIMDD-COOH (mouse GLI2, amino acid residues 1509-1526), differ only in one amino acid residue position (italics and underlined). The transactivation domains of human GLI3, NH$_2$-DSHDLEGVQIDFDAIIDD-COOH (human GLI3, amino acid residues 1495-1512), and mouse GLI3, NH$_2$-ESHDLEGVQIDFDAIIDD-COOH (amino acid residues 1497-1514), also differ only in one amino acid residue position (italics and underlined).

However, there is much greater divergence between human GLI1, human GLI2 and human GLI3 (asterisks indicate identical amino acid residues between human GLI1, GLI2 and GLI3):

```
NH2-DSLDLDNTQLDFVAILDE-COOH (human GLI1, amino acid residues 1037-1054)
     **  *   *  **  ** *

NH2-DSQLLEAPQIDFDAIMDD-COOH (human GLI2, amino acid residues 1501-1518),
     **  *   *  **  ** *

NH2-DSHDLEGVQIDFDAIIDD-COOH (human GLI3, amino acid residues 1495-1512),
```

The following is a comparison of the TAF$_{II}$31 interaction domains of human GLI1 and human GLI2 (asterisks indicate identity of amino acid residues):

```
NH2-DSLDLDNTQLDFVAILDE-COOH (human GLI1, amino acid residues 1037-1054)
     **  *   *  **  ** *

NH2-DSQLLEAPQIDFDAIMDD-COOH (human GLI2, amino acid residues 1501-1518)
```

The following is a comparison of the TAF$_{II}$31 interaction domains of human GLI2 and human GLI3 (asterisks indicate identity of amino acid residues):

```
NH2-DSQLLEAPQIDFDAIMDD-COOH (human GLI2, amino acid residues 1501-1518)
     **  **  *******  **

NH2-DSHDLEGVQIDFDAIIDD-COOH (human GLI3, amino acid residues 1495-1512)
```

As described, specific as well as redundant functions have been demonstrated for GLI2 and GLI3 during mammalian skeletal development, whereas, e.g., GLI1 but not GLI3 has been shown to activate the HNF-3β enhancer in tissue culture (Mo et al., 1997, *Development* 124:113-123; Sasaki et al., 1997, *Development* 124:1313-1322). Differences in TAF binding or binding affinity could potentially contribute to the different properties of GLI1, GLI2, and GLI3.

Yoon et al. described that the GLI1 transcription activation domain is similar to the VP16 transcription activation domain which comprises an α-helical domain including conservation of the FXXΦΦ motif. (Yoon et al., 1998, *J. Biol. Chem.*, 273(6):3496-3501). The VP16 activation domain undergoes an induced transition from a random coil to an α-helix upon binding to its target protein, TAF$_{II}$31 and three residues believed to make direct contacts with TAF$_{II}$31 have been identified: D472, F479, and L483 (Uesugi et al., 1997, *Science*, 277:1310-1313) These three amino acid residues are also found within the activation domain of human GLI1 (D1040, F1048, and L1052), which comprises the FXXΦΦ (FVAIL).

The FXXΦΦ motif in GLI3, it is FDAII. It is highly likely that this motif of GLI3 is directly involved in contacting a TAF, presumably TAF$_{II}$31.

FXXΦΦ motifs have also been described within the activation domains of the tumor suppressor gene p53 and in NF-$_k$B p65. MDM2, the cellular attenuator of p53, discriminates the FXXΦΦ motif of p53 of those of NF-$_k$B p65 and VP16 and specifically inhibits p53 activity (Uesugi and Verdine, 1999, *Proc. Natl. Acad. Sci. USA*, 96(26):14801-14806). Therefore, it seems plausible to assume that the activation domain of a polypeptide I comprising a FXXΦΦ motif can be differentiated from the activation domain of polypeptide II also comprising a FXXΦΦ motif, but having a different amino acid sequence. Thus, it should also be possible to significantly inhibit the activity of polypeptide I (such as GLI3), but not significantly the activity of polypeptide II by designing and using a small molecule compound mimicking the FXXΦΦ motif of polypeptide I, i.e., the amino acid sequence of the FXXΦΦ motif of polypeptide I.

Thus, it is an objective of the present invention to provide a small molecule compound that significantly inhibits GLI3 signaling, but not significantly GLI or GLI2 signaling. Thus, in one aspect of the invention, a small molecule compound is provided that differently affects the transcriptional activation potential of GLI1, GLI2, and GLI3.

In one embodiment of the present invention a small molecule compound inhibits or reduces the binding of GLI3 to a TAF, preferably TAF$_{II}$31.

In another embodiment of the present invention, a small molecule compound is provided that mimics an FXXΦΦ motif of a GLI protein, preferably a human or mouse GLI protein. In a preferred embodiment, the small molecule compound mimics the FXXΦΦ motif of GLI3, FDAII (see FIG. 3).

In other embodiments of the present invention, a small molecule compound mimics the FXXΦΦ motif of GLI2, FDAIM. In yet another embodiment of the present invention, the small compound molecule mimics the FXXΦΦ motif of GLI1, FVAIL.

B. Small Molecule Compounds of the Present Invention

Figure 3:
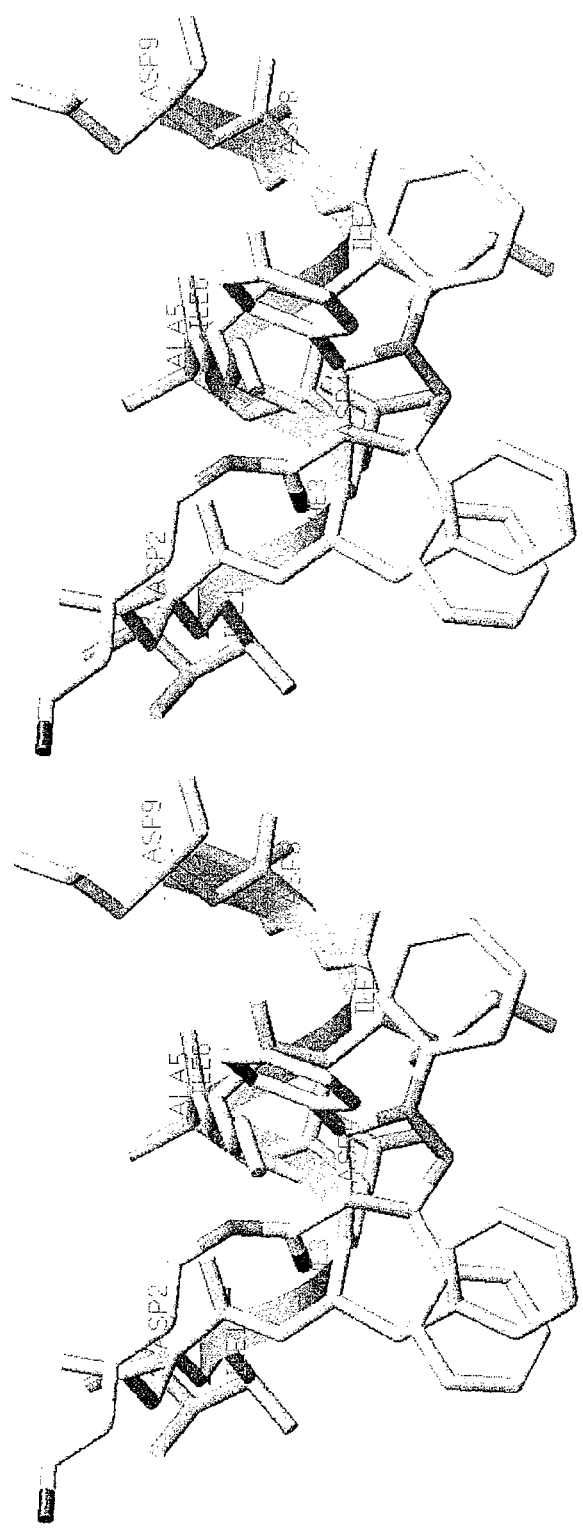
FIG. 3 shows a manually generated RMS overlay between the small molecule compound FN1-5 and the FXXΦΦ motif for GLI3 (amino acid sequence: FDAII). The FDAII is shown as an alpha-helix. Details are described, e.g., in Example 2.

As described above, it is an objective of the present invention to provide small molecule compound that mimic the transcription activation domain of a GLI polypeptide, preferably a GLI3 polypeptide. Many α-helical mimetics including tri-aryl/alkyl heterocycle compounds are described in the prior art. However, compounds mimicking α-helical domains that are based on pyrazoline are not well studied. Thus, it is an objective of the present invention to provide small molecule compounds that are based on pyrazoline and which mimic an α-helical domain of a GLI transcription activation domain, preferably an α-helical domain of a GLI3 transcription activation domain. A RMS overlay of a small molecule compound of the present invention (FN1-5; see below) with a proposed α-helical domain comprising the FDAII motif of GLI3 is shown in FIG. 3.

Thus, the compounds of the present invention include small molecule compounds of the formula

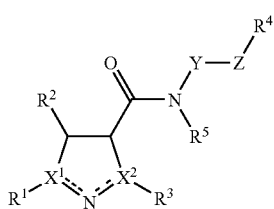

wherein each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C. Additionally, each of $R^1$, $R^2$ and $R^3$ is independently selected from the group consisting of $C_1$-$C_6$ alkyl, aryl, heteroaryl, cycloalkyl and heterocycloalkyl, optionally substituted with 0-3 $R^6$ groups each independently selected from the group consisting of H, halogen, $C_1$-$C_6$ alkyl, —$OR^7$, —$C(O)R^7$, —$OC(O)R^7$, —$N(R^7,R^7)$, —$NR^7S(O)_2R^7$, —$C(O)N(R^7,R^7)$, —$N(R^7)C(O)R^7$, —$N(R^7)C(O)N(R^7,R^7)$, —$C(NR^7)N(R^7,R^7)$, —$N(R^7)C(NR^7)N(R^7,R^7)$ and $S(O)_mR^7$ wherein subscript m is 0, 1 or 2. Y is a direct bond or $C_1$-$C_4$ alkyl, and Z is a member selected from the group consisting of $C_1$-$C_4$ alkyl, aryl and heteroaryl. $R^4$ is H, halogen, —$OR^7$, —$OC(O)R^7$, —$C(O)OR^7$, —$N(R^7,R^7)$, —$NR^7S(O)_2R^7$, —$C(O)N(R^7,R^7)$, —$N(R^7)C(O)N(R^7,R^7)$, —$C(NR^7)N(R^7, R^7)$ and $S(O)_mR^7$ wherein subscript m is 0, 1 or 2. $R^5$ is H, $C_1$-$C_6$ alkyl, or optionally combined with Y to form a 5 to 6 membered heterocycle. Each $R^7$ is independently H or $C_1$-$C_6$ alkyl.

In addition, the salts, hydrates, solvates, isomers and prodrugs of a small molecule compound of the present invention are also contemplated.

In another embodiment, the present invention provides a small molecule compound of the formula where each of $R^1$, $R^2$ and $R^3$ is aryl. In a further embodiment, each of $R^1$, $R^2$ and $R^3$ is phenyl.

In another embodiment, the present invention provides a small molecule compound of the formula where $R^4$ is hydroxy. In another embodiment, Z is $C_1$-$C_4$ alkyl. In still another embodiment, Z is aryl. In yet another embodiment, Z is phenyl.

In a further embodiment, the present invention provides a small molecule compound of the formula where each of $R^1$, $R^2$ and $R^3$ is phenyl, where Y is $C_1$-$C_4$ alkyl, where Z is $C_1$-$C_4$ alkyl or phenyl, and where $R^4$ is hydroxy.

Thus, preferred small molecule compounds of the present invention include, but are not limited to, the following:

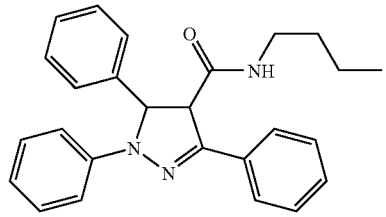

FN1-3

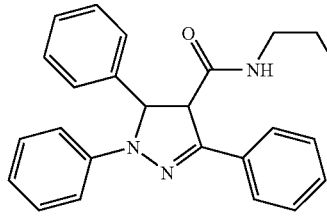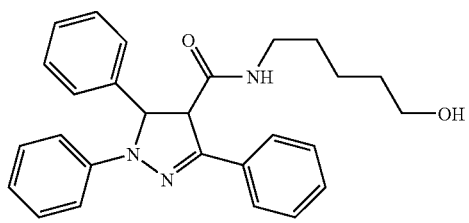

FN1-5

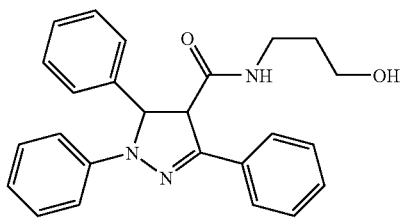

FN1-7

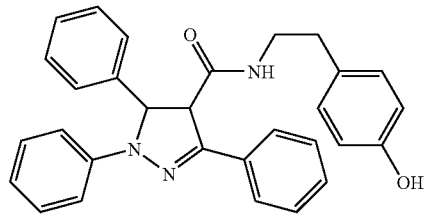

FN1-8

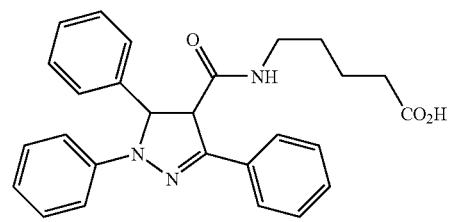

FN1-9U

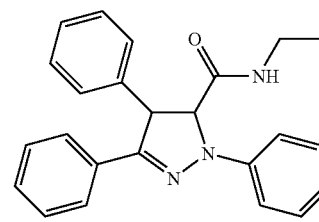

FN1-9S

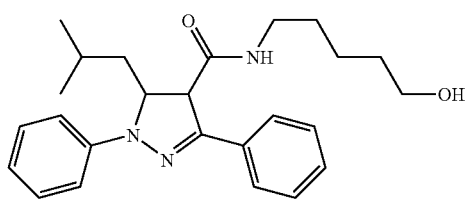

FN2-5

-continued

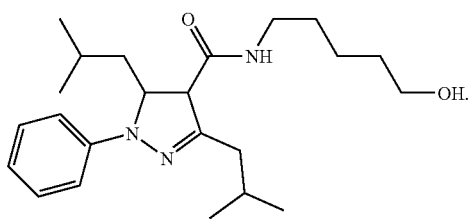

FN3-5

Other compounds of the present invention include the following small molecule compounds:

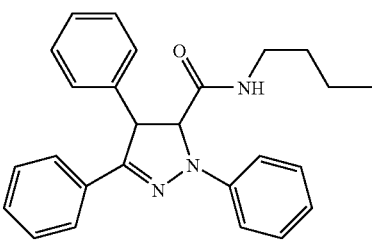

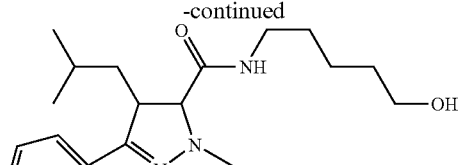

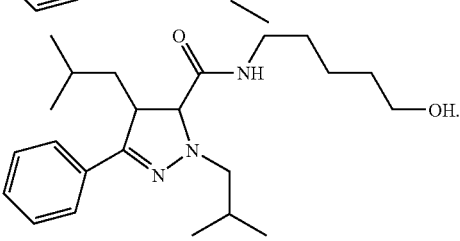

One of skill in the art will appreciate that other small molecule compounds are useful in the present invention.

C. Preparation of Small Molecule Compounds

The small molecule compounds of the present invention can be prepared via condensation of ethyl cinnamate and benzaldehyde phenylhydrazone, followed by saponification of the ethyl ester and reaction with an amine to afford the desired amide end-product (see Example 3). Alternatively, the small molecule compounds of the present invention can be prepared by first reacting cinnamic acid with the amine to prepare the amide, then condensation with the benzaldehyde phenylhydrazone. One of skill in the art will recognize that additional methods exist for the preparation of the small molecule compounds of the present invention.

In one embodiment of the present invention, a small molecule compound of the present invention comprises a label. This is particular useful for detecting and testing the distribution of the small molecule compound after administration in vivo. For example, 3H can be used as a label in conventional pharmacokinetic/dynamic studies. A small molecule compound comprising a label can be detected by, for example, spectroscopic, photochemical, biochemical, immunochemical, chemical, or other physical means.

A small molecule compound of the present invention may also contain unnatural proportions of atomic isotopes at one or more of the atoms that constitute such compounds. For example, the compounds may be radiolabeled with radioactive isotopes, such as for example tritium ($^3$H) or carbon-14 ($^{14}$C). All isotopic variations of the compounds of the present invention, whether radioactive or not, are intended to be encompassed within the scope of the present invention.

D. Testing of Small Molecule Compounds in Cell-Based Assays

A small molecule compound of the present invention can be screened for activity in vitro and in vivo. For in vitro assays, this invention provides cell-based cytotoxicity assays, and apoptosis assays as described herein (e.g., see Example 1). For in vivo assays, this invention provides mouse xenograft assays as described herein (e.g., see Examples 33-35).

III. Pharmaceutical Compositions

In one aspect the present invention provides a pharmaceutical composition or a medicament comprising at least one small molecule compound of the present invention and optionally a pharmaceutically acceptable carrier. A pharmaceutical composition or medicament can be administered to a patient for the treatment of, for example, a condition, such as cancer.

A. Formulation and Administration

The small molecule compounds of the present invention are useful in the manufacture of a pharmaceutical composition or a medicament comprising an effective amount thereof in conjunction or mixture with excipients or carriers suitable for either enteral or parenteral application.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. The small molecule compounds of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The small molecule compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In one embodiment of the present invention, a pharmaceutical composition or medicament comprises an effective amount of a compound of the present invention as defined above, and another therapeutic agent, such as a chemotherapeutic agent. Examples of chemotherapeutic agents include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J.

When used with a small molecule compound of the invention, such chemotherapeutic agent may be used individually (e.g., 5-FU and small molecule compound), sequentially (e.g., 5-FU and small molecule compound for a period of time followed by e.g., MTX and small molecule compound), or in combination with one or more other such chemotherapeutic agents (e.g., 5-FU, MTX and small molecule compound, or 5-FU, radiotherapy and small molecule compound). Administration may be by the same or different route of administration or together in the same pharmaceutical formulation.

In one aspect of the present invention, a therapeutically effective amount of a small molecule compound of the present invention is administered in combination with surgery, and optionally administration of another chemotherapeutic agent.

B. Therapeutically Effective Amount and Dosing

In one embodiment of the present invention, a pharmaceutical composition or medicament is administered to a patient at a therapeutically effective dose to prevent, treat, or control cancer. The pharmaceutical composition or medicament is administered to a patient in an amount sufficient to elicit an effective therapeutic response in the patient. An effective therapeutic response is a response that at least partially arrests or slows the symptoms or complications of the disease. An amount adequate to accomplish this is defined as "therapeutically effective dose."

The dosage of active small molecule compound administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of the active small molecule compound of the present invention, is a dosage that is sufficient to achieve the desired effect.

Optimal dosing schedules can be calculated from measurements of small molecule compound accumulation in the body of a subject. In general, dosage is from 1 ng to 1,000 mg per kg of body weight and may be given once or more daily, weekly, monthly, or yearly. Persons of ordinary skill in the art can easily determine optimum dosages, dosing methodologies and repetition rates.

In one embodiment of the present invention, a pharmaceutical composition or medicament comprising a small molecule compound of the present invention is administered in a daily dose in the range from about 1 mg of small molecule compound per kg of subject weight (1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In another embodiment, the daily dose is about 25 mg/kg to about 150 mg/kg. The daily dose can be administered once per day or divided into subdoses and administered in multiple doses, e.g., twice, three times, or four times per day.

Figure 15:
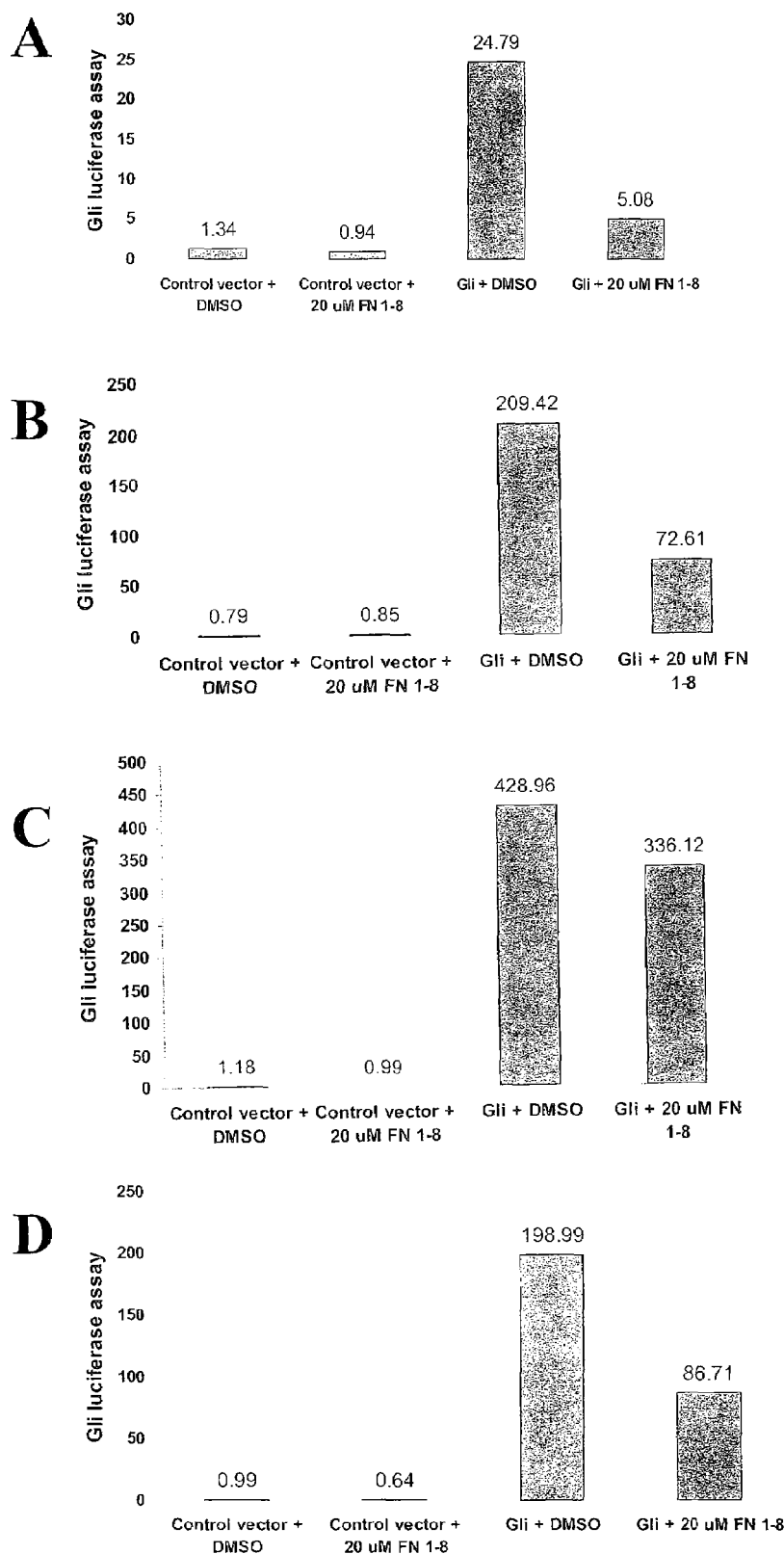
FIG. 15 shows that small molecule compound FN1-8 down-regulates GLI1-induced transcription activity in the melanoma cell lines Malme-3M (A), A375 (B), SK-Mel-2 (C), and SK-Mel-5 (D). Details are described in Example 29.

To achieve the desired therapeutic effect, a small molecule compound must be administered for multiple days at the therapeutically effective daily dose. Thus, therapeutically effective administration of a small molecule compound to treat cancer in a subject requires periodic (e.g., daily) administration that continues for a period ranging from three days to two weeks or longer. Typically, a small molecule compound will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the small molecule compound is not administered daily, so long as the administration is repeated frequently enough to maintain a therapeutically effective concentration of the small molecule compound in the subject. For example, one can administer the small molecule compound every other day, every third day, or, if higher dose ranges are employed and tolerated by the subject, once a week. A dosing schedule, for example, is described in Examples 33-35 and in FIGS. 15-17.

Optimum dosages, toxicity, and therapeutic efficacy of such small molecule compounds may vary depending on the relative potency of individual small molecule compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any small molecule compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a small molecule compound is from about 1 ng/kg to 100 mg/kg for a typical subject.

Following successful treatment, it may be desirable to have the subject undergo maintenance therapy to prevent the recurrence of the condition treated, e.g., a cancer.

IV. Identification of Cells Expressing GLI Proteins

A. Detection of GLI Proteins

In another embodiment, the method of detecting a cancer comprises determining the level of a GLI polypeptide, preferably a GLI1, GLI2, or GLI3 polypeptide in a biological sample from a subject, such as a patient. In a preferred embodiment, the level of an activator fragment of a GLI3 protein comprising a transcription activation domain, is determined. Detecting an increase in the level of the GLI polypeptide, preferably the GLI1, GLI2, or GLI3 polypeptide or an increase in the level of an activator fragment of the GLI3 protein relative to normal indicates the presence of cancer in the subject.

Upregulation of, for example, GLI1, GLI2, or GLI3 expression is indicative of and can be correlated with various cancers. Thus, a GLI1, GLI2, or GLI3 polypeptide or a Gli1, Gli2, or Gli3 polynucleotide can be used as a biomarker in the diagnosis of cancer. In one preferred embodiment of the present invention, the amount of a GLI protein, e.g., a GLI3, in a biological sample is determined. Typically, for example, the amount of GLI3 in a biological sample provided from a normal, healthy or non-cancer subject is correlated with the amount of GLI3 in a biological sample provided from a cancer subject or from a subject suspected of having cancer. The amount of GLI3 detected in the biological sample from the cancer subject or from the subject suspected of having cancer may be specific for a given cancer.

Detection of, for example, a GLI polypeptide, such as a GLI3 polypeptide can be accomplished by any specific detection method including, but not limited to, affinity capture, mass spectrometry, traditional immunoassay directed to GLI3, PAGE, Western Blotting, or HPLC as further described herein or as known by one skilled in the art.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

B. Detection of Gli mRNA

In one embodiment, the method of detecting cancer comprises determining the level of a transcript encoding a GLI polypeptide, preferably a GLI3 polypeptide (see e.g., Genbank accession NM 007191 and SEQ ID NO: 1) in a biological sample from a subject, such as a patient. Detecting an increase in the level of the Gli mRNA, preferably the GLI3 mRNA relative to normal indicates the presence of cancer in the subject. In one embodiment, the step of determining the level of the Gli mRNA comprises an amplification reaction. In another embodiment, the presence of cancer is evaluated by determining in a cell the level of expression of mRNA encoding a GLI polypeptide. A Gli mRNA level higher than in a corresponding non-cancerous tissue indicates the presence of cancer. Methods of evaluating RNA expression of a particular gene are well known to those of skill in the art, and include, inter alia, hybridization and amplification based assays.

1. Direct Hybridization-Based Assays

Methods of detecting and/or quantifying the level of Gli gene transcripts (mRNA or cDNA made therefrom) using nucleic acid hybridization techniques are known to those of skill in the art. For example, one method for evaluating the presence, absence, or quantity of Gli polynucleotides, e.g., Gli3 polynucleotides involves a Northern blot. Gene expression levels can also be analyzed by techniques known in the art, e.g., dot blotting, in situ hybridization, RNase protection, probing DNA microchip arrays, and the like.

2. Amplification-Based Assays

In another embodiment, amplification-based assays are used to measure the expression level of a Gli gene, preferably the Gli3 gene. In such an assay, the Gli nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of Gli m-RNA in the sample. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). The known nucleic acid sequences for Gli (see, e.g., ATCC Accession Nos. herein) is sufficient to enable one of skill to routinely select primers to amplify any portion of the gene. A semi-quantitative RT-PCR analysis is described, e.g., in Example 1 and in FIG. 2.

In one embodiment, a TaqMan based assay is used to quantify the cancer-associated polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

Other suitable amplification methods include, but are not limited to, ligase chain reaction (LCR) (see, Wu and Wallace, *Genomics* 4:560 (1989); Landegren et al., *Science* 241:1077 (1988); and Barringer et al., *Gene* 89:117 (1990)), transcription amplification (Kwoh et al., *Proc. Natl. Acad. Sci. USA* 86:1173 (1989)), self-sustained sequence replication (Guatelli et al., *Proc. Nat. Acad. Sci. USA* 87: 1874 (1990)), dot PCR, and linker adapter PCR, etc.

V. Methods

The small molecule compounds of the present invention find use in a variety of ways. The present invention provides methods for using the small molecule compounds of the present invention to, for example, (i) induce apoptosis in a cell expressing a GLI polypeptide, (ii) inhibit unwanted growth, proliferation or survival of a cell expressing a GLI polypeptide, (iii) treat a condition, such as a cancer, expressing a GLI polypeptide, (iv) inhibit expression of a gene having a GLI DNA binding site, and (v) inhibit the activity of a GLI polypeptide.

Any cell or tumor cell expressing a GLI polypeptide, preferably a GLI3 polypeptide can be used to practice a method of the present invention. A preferred cell or tumor cell expressing a GLI polypeptide is selected from the group consisting of colon cancer, melanoma, mesothelioma, lung cancer, renal cell carcinoma, breast cancer, prostate cancer, sarcoma, ovarian cancer, esophageal cancer, gastric cancer, hepatocellular cancer, nasopharyngeal cancer, pancreatic cancer, and glioma cell.

Methods of the present invention can be practiced in vitro or in vivo.

A. Inducing Apoptosis in a Cell Using a Small Molecule Compound

Apoptosis plays a central role in both the development and homeostasis of multicellular organisms. "Apoptosis" refers to programmed cell death and is characterized by certain cellular characteristics, such as membrane blobbing, chromatin condensation and fragmentation, formation of apoptotic bodies and a [positive "TUNEL" (terminal deoxynucleotidyl transferase-mediated UTP nick end-labeling) staining pattern. A later step in apoptotic process is the degradation of the plasma membrane, rendering apoptotic cells leaky to various dyes (e.g., propidium iodide).

Apoptosis can be induced by multiple independent signaling pathways that converge upon a final effector mechanism consisting of multiple interactions between several death receptors and their ligands, which belong to the tumor necrosis factor (TNF) receptor/ligand superfamily. The best-characterized death receptors are CD95 ("Fas"), TNFR1 (p55), death receptor 3 (DR3 or Apo3/TRAMO), DR4 and DR5 (apo2-TRAIL-R2). The final effector mechanism of apoptosis is the activation of a series of proteinases designated as caspases. The activation of these caspases results in the cleavage of a series of vital cellular proteins and cell death.

The present invention provides methods for inducing apoptosis in a cell expressing a GLI protein. In one aspect, the method for inducing apoptosis in a cell comprises the step of exposing the cell to a composition or contacting the cell with a composition comprising a small molecule compound of the present invention. In a preferred embodiment, the composition comprises small molecule compound FN1-5. In another preferred embodiment, the composition comprises small molecule compound FN1-8. Typically, the cells are exposed to or contacted with an effective amount of the composition wherein the contacting results in inducing apoptosis. In a preferred embodiment, the GLI protein is GLI2 or GLI3.

In another preferred embodiment of the present invention, exposing a cell to a composition comprising a small molecule of the invention comprises introducing the composition into the cell.

In another aspect of present invention, a method of inducing a tumor cell to undergo apoptosis is provided comprising the step of administering a small molecule compound of the present invention. In a preferred embodiment, the small molecule compound is FN1-5. In another preferred embodiment, the small molecule compound is FN1-8.

In a preferred embodiment, the cells are exposed ex vivo to or contacted ex vivo with the composition. In another preferred embodiment, the cell is exposed in vivo to or contacted in vivo with the composition.

B. Inhibiting Unwanted Growth, Proliferation or Survival of a Cell Using Small Molecule Compounds It is an object of the present invention to provide novel therapeutic strategies for treatment of cancers using then small molecule compounds of the invention that prevent signaling through the GLI signaling pathway. In one aspect of the present invention, a method for inhibiting at least one of unwanted growth, hyperproliferation, or survival of a cell is provided. This method comprises the step of determining whether the cell expresses a Gli gene or alternatively a GLI polypeptide. This method also comprises the step of contacting the cell with an effective amount of a small molecule of the present invention, wherein the step of contacting results in the inhibition of at least one of unwanted growth, hyperproliferation, or survival of the cell.

A preferred cell or tumor cell for which at least one of unwanted growth, hyperproliferation, or survival of a cell is inhibited, is selected from the group consisting of colon cancer cell, melanoma cell, mesothelioma cell, lung cancer cell, renal cell carcinoma cell, breast cancer cell, prostate cancer cell, sarcoma cell, ovarian cancer cell, esophageal cancer cell, gastric cancer cell, hepatocellular cancer cell, nasopharyngeal cancer cell, pancreatic cancer cell, and glioma cell.

In another preferred embodiment of this invention, a method of inhibiting proliferation of a cell that expresses a GLI polypeptide, preferably a GLI3, is provided. "Proliferation" refers to the growth of a cell, the reproduction or multiplication of a cell or morbid cysts. This method comprises the step of contacting the cell with an amount of a small molecule compound effective to inhibit proliferation of the cell. Preferably small molecule compounds FN1-5 or FN1-8, either alone or in combination are useful for inhibiting proliferation of a cell, preferably a cancer cell.

In a preferred embodiment of the present invention, this method is practiced in vitro. As further described herein, methods of the present invention can also be practiced in vivo.

Many tumors form metastasis. Thus, in another aspect of the present invention, the small molecule compounds of the present invention are used to prevent the formation of a metastasis. This method comprises the step of administering to a tumor cell a small molecule compound of the present invention wherein the administering results in prevention from metastasis. In a preferred embodiment, the small molecule compound is FN1-5. In another preferred embodiment, the small molecule compound is FN1-8.

In a preferred embodiment of the present invention, the cell expressing a GLI protein and being contacted with a small molecule compound of the present invention is a cancer cell selected from the group consisting of colon cancer, melanoma, mesothelioma, lung cancer, renal cell carcinoma, breast cancer, prostate cancer, sarcoma, ovarian cancer, esophageal cancer, gastric cancer, hepatocellular cancer, nasopharyngeal cancer, pancreatic cancer, and glioma cell. A preferred cancer cell is a lung cancer cell, a colon cancer cell, or a melanoma cell.

C. Treating Cancer Using Small Molecule Compounds

Methods of the present invention can be practiced in vitro and in vivo. Thus, in another aspect of the present invention, a method for treating a subject suffering from a cancerous condition is provided. This method comprises the step of administering to the subject a therapeutically effective amount of a small molecule compound, wherein the cancerous condition is characterized by expressing a GLI polypeptide, preferably a GLI1, GLI2, or GLI3 polypeptide, and wherein the step of administering results in the treatment of the subject.

Figure 2:
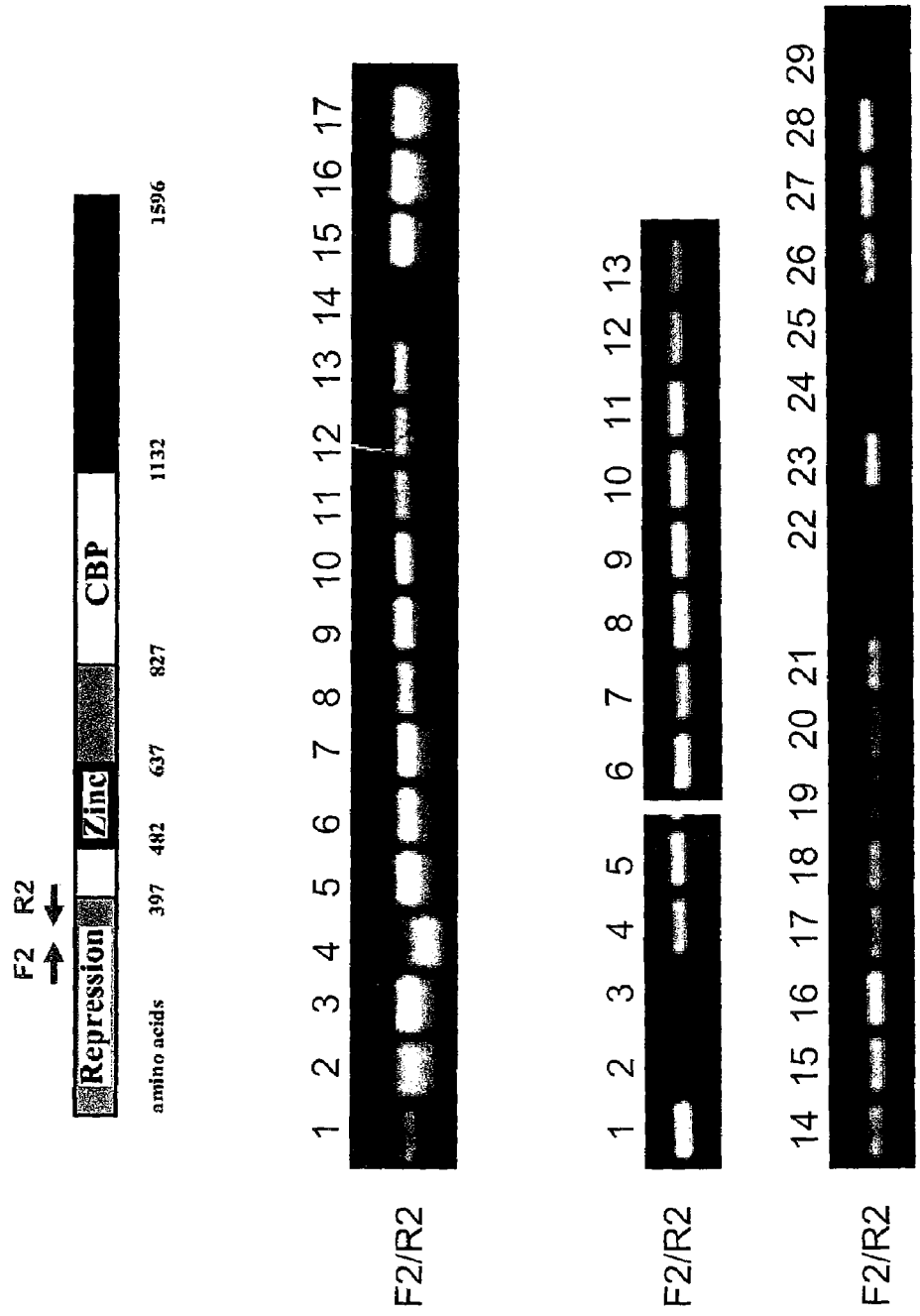
FIG. 2 shows a semi-quantitative RT-PCR analysis to demonstrate detection of Gli3 expression in human cell lines. The upper panel of this figure shows a schematic representation of GLI3 showing the repression domain (amino acid residues 1-397), the Zinc finger domain (amino acid residues 482-637) and the CBP-binding domain (amino acid residues 827-1132). The approximate location of PCR primers F2 and R2 is indicated (see Table 1 for details). The middle panel of this figure (lanes 1-17) shows the following cell lines analyzed by RT-PCR: normal liver (lane 1); NSCLC: H1703, H460 and A549 (lanes 2-4); breast cancer: HuL100, BT474 and MCF-7 (lanes 5-7); mesothelioma: Met5A, H290, REN, H513, H28, 211H, and LARK1A (lanes 8-14); colon cancer: SW480 (lane 15); a pair of primary NSCLC tissue samples (lanes 16 and 17 are normal and cancer tissues, respectively). The lower panel of this figure (lanes 1-29) shows the following cell lines analyzed by RT-PCR: Colon cancer: SW480, HCT 116, HT29, Lovo and CaCO2 (lanes 1-5); normal colon (lane 6); normal renal cell lines: HRE-152 and HK-2 (lanes 7 and 8); renal cell carcinoma: 786-Om Caki, 769-P, A704 and OMRC3 (lanes 9-13); normal lung (lane 14); mesothelioma: REN, H290, 211H, H513, H2052, H28 and MS-1 (lanes 15-21); NSCLC: A549, H460, H838, H1703, H1229, H1650, H1975, and A427 (lanes 22-29). Most cancer cell lines and the primary tissue samples express Gli3. Notably, no Gli3 expression is detected in colon cancer cell line HT29 (lower panel, lane 2). Details are described in Example 4.

As shown herein, most cancers express a GLI polypeptide, preferably a GLI3 polypeptide (FIG. 2; data not shown). Thus, most cancerous conditions or cancers in a subject can be treated using a small molecule compound of the present invention. A preferred cancerous condition or cancer is selected from the group consisting of colon cancer, melanoma, mesothelioma, lung cancer, renal cell carcinoma, breast cancer, prostate cancer, sarcoma, ovarian cancer, esophageal cancer, gastric cancer, hepatocellular cancer, nasopharyngeal cancer, pancreatic cancer, and glioma.

Thus, in a preferred embodiment of the present invention, a small molecule compound is used to treat a subject suffering from a colon cancer expressing a GLI polypeptide, preferably a GLI1, GLI2, or GLI3 polypeptide.

In another preferred embodiment of the present invention, a small molecule compound is used to treat a subject suffering from a breast cancer expressing a GLI polypeptide, preferably a GLI1, GLI2, or GLI3 polypeptide.

In yet another preferred embodiment of the present invention, a small molecule compound is used to treat a subject suffering from a nasopharyngeal cancer expressing a GLI polypeptide, preferably a GLI1, GLI2, or GLI3 polypeptide.

In one embodiment of the present invention, a small molecule compound is used to treat a subject suffering from a lung cancer expressing a GLI polypeptide, preferably a GLI1, GLI2, or GLI3 polypeptide. A lung cancer includes, but is not limited to, bronchogenic carcinoma [squamous cell, undifferentiated small cell, undifferentiated large cell, adenocarcinoma], alveolar [bronchiolar] carcinoma, bronchial adenoma, sarcoma, lymphoma, chondromatous hamartoma, mesothelioma, SCLC, and NSCLC.

In another embodiment of the present invention, a small molecule compound is used to treat a subject suffering from a sarcoma expressing a GLI polypeptide, preferably a GLI1, GLI2, or GLI3 polypeptide. A sarcoma includes, but is not limited to, cancers such as angiosarcoma, fibrosarcoma, rhabdomyosarcoma, liposarcoma, myxoma, rhabdomyoma, fibroma, lipoma and teratoma.

In yet another embodiment of the present invention, a small molecule compound is used to treat a subject suffering from a gastrointestinal cancer expressing a GLI polypeptide, preferably a GLI1, GLI2, or GLI3 polypeptide. A gastrointestinal cancer includes, but is not limited to cancers of esophagus [squamous cell carcinoma, adenocarcinoma, leiomyosarcoma, lymphoma], stomach [carcinoma, lymphoma, leiomyosarcoma], pancreas [ductal adenocarcinoma, insulinoma, glucagonoma, gastrinoma, carcinoid tumors, VIPoma], small bowel [adenocarcinoma, lymphoma, carcinoid tumors, Kaposi's sarcoma, leiomyoma, hemangioma, lipoma, neurofibroma, fibroma], and large bowel [adenocarcinoma, tubular adenoma, villous adenoma, hamartoma, leiomyoma].

In one embodiment of the present invention, a small molecule compound is used to treat a subject suffering from a cancer of the genitourinary tract expressing a GLI polypeptide, preferably a GLI1, GLI2, or GLI3 polypeptide. Cancers of the genitourinary tract include, but are not limited to cancers of kidney [adenocarcinoma, Wilms tumor (nephroblastoma), lymphoma, leukemia, renal cell carcinoma], bladder and urethra [squamous cell carcinoma, transitional cell carcinoma, adenocarcinoma], prostate [adenocarcinoma, sarcoma], and testis [seminoma, teratoma, embryonal carcinoma, teratocarcinoma, choriocarcinoma, sarcoma, Leydig cell tumor, fibroma, fibroadenoma, adenomatoid tumors, lipoma].

In another embodiment of the present invention, a small molecule compound is used to treat a subject suffering from a liver cancer expressing a GLI polypeptide, preferably a GLI1, GLI2, or GLI3 polypeptide. A liver cancer includes, but is not limited to, hepatocellular carcinoma, cholangiocarcinoma, hepatoblastoma, angiosarcoma, hepatocellular adenoma, and hemangioma.

In one embodiment of the present invention, a small molecule compound is used to treat a subject suffering from a skin cancer expressing a GLI polypeptide, preferably a GLI1, GLI2, or GLI3 polypeptide. Skin cancer includes, but is not limited to, malignant melanoma, basal cell carcinoma, squamous cell carcinoma, Kaposi's sarcoma, nevi, dysplastic nevi, lipoma, angioma, dermatofibroma, keloids, and psoriasis.

In one embodiment of the present invention, a small molecule compound is used to treat a subject suffering from a gynecological cancer expressing a GLI polypeptide, preferably a GLI1, GLI2, or GLI3 polypeptide. Gynecological cancers include, but are not limited to, cancer of uterus [endometrial carcinoma], cervix [cervical carcinoma, pre-invasive cervical dysplasia], ovaries [ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors], vulva [squamous cell carcinoma, intraepithelial carcinoma, adenocarcinoma, fibrosarcoma, melanoma], vagina [clear cell carcinoma, squamous cell carcinoma, sarcoma botryoides (embryonal rhabdomyosarcoma), and fallopian tubes [carcinoma].

In yet another embodiment of the present invention, a small molecule compound is used to treat a subject suffering from a bone cancer expressing a GLI polypeptide, preferably a GLI1, GLI2, or GLI3 polypeptide. Bone cancer includes, but is not limited to, osteogenic sarcoma [osteosarcoma], fibrosarcoma, malignant fibrous histiocytoma, chondrosarcoma, Ewing's sarcoma, malignant lymphoma [reticulum cell sarcoma], multiple myeloma, malignant giant cell tumor, chordoma, osteochondroma [osteocartilaginous exostoses], benign chondroma, chondroblastoma, chondromyxoid fibroma, osteoid osteoma, and giant cell tumors.

In one embodiment of the present invention, a small molecule compound is used to treat a subject suffering from a cancer of the nervous system expressing a GLI polypeptide, preferably a GLI1, GLI2, or GLI3 polypeptide. Cancers of the nervous system include, but are not limited to cancers of skull [osteoma, hemangioma, granuloma, xanthoma, Paget's disease of bone], meninges [meningioma, meningiosarcoma, gliomatosis], brain [astrocytoma, medulloblastoma, glioma, ependymoma, germinoma (pinealoma), glioblastoma multiforme, oligodendroglioma, schwannoma, retinoblastoma, congenital tumors], and spinal cord [neurofibroma, meningioma, glioma, sarcoma].

In one embodiment of the present invention, a small molecule compound is used to treat a subject suffering from a hematologic cancer expressing a GLI polypeptide, preferably a GLI1, GLI2, or GLI3 polypeptide. Hematologic cancers include, but are not limited to cancer of blood [myeloid leukemia (acute and chronic), acute lymphoblastic leukemia, chronic lymphocytic leukemia, myeloproliferative diseases, multiple myeloma, myelodysplastic syndrome], Hodgkin's disease, and non-Hodgkin's lymphoma (malignant lymphoma).

In one embodiment of the present invention, a small molecule compound is used to treat a subject suffering from a cancer of adrenal glands expressing a GLI polypeptide, preferably a GLI1, GLI2, or GLI3 polypeptide. A cancer of adrenal glands includes, but is not limited to, neuroblastoma.

The present invention provides a method for treatment or prevention of a cancer wherein a GLI polypeptide, preferably a GLI1, GLI2, or GLI3 polypeptide is expressed. In one embodiment of the present invention, this method comprises the step of administering to a patient a pharmaceutical composition. Such pharmaceutical composition comprises, for example, a small molecule compound of the present invention. In a preferred embodiment the small molecule compound is FN1-5. In another preferred embodiment, the small molecule compound is FN1-8. Pharmaceutical compositions of the present invention are administered alone or in combination with one or more additional therapeutic compound or treatments. Examples of such therapeutic compounds or treatments include, but are not limited to, taxol, cyclophosphamide, tamoxifen, fluoruracil and doxorubicin. In addition, other chemotherapeutic agents are described herein.

Methods for treating cancer may optionally comprise one or more of the following steps: obtaining a biological sample of tissue or fluid from an individual; screening the biological sample for the expression of a GLI polypeptide, preferably a GLI1, GLI2, or GLI3 polypeptide, for example by contacting the biological sample with an antibody directed to GLI1, GLI2, or GLI3; or screening the biological sample for expression of a Gli1, Gli2, or Gli3 polynucleotide, for example by detecting a Gli1, Gli2, or Gli3 mRNA.

Many cancers are initially treated using chemotherapeutic agents as described herein. However, very often, cancers develop resistance against such chemotherapeutic agents which then are not longer effective. Thus, in one embodiment, the cancer is a multi-drug resistant cancer or a cancer that is otherwise refractory to treatment. Therefore, in another aspect of the present invention, a small molecule compound of the present invention is used to overcome resistance to chemotherapeutic agents in tumor cells. This method comprises the step of administering to a tumor cell resistant to at least one chemotherapeutic agent a small molecule compound of the present invention, wherein the administering results in subsequent tumor cell death. In a preferred embodiment, the small molecule compound is FN1-5. In another preferred embodiment, the small molecule compound is FN1-8.

D. Inhibiting Expression of a Gene Having a GLI DNA Binding Site

Because a GLI polypeptide, such as a GLI1, GLI2, or GLI3 polypeptide, functions as a transcriptional activator, inhibition of GLI transcriptional activity by the methods of the present invention should also inhibit or down-regulate the expression of down-stream genes i.e., genes whose expression is regulated by GLI, preferably by GLI1, GLI2, or GLI3. GLI typically regulates expression of down-stream genes by binding to its cognate DNA binding site operably linked to the promoter and/or enhancer sequence of down-stream genes. For example, a DNA binding site for GLI3 has been described (Vortkamp et al. 1995, *DNA Cell. Biol.* 14:629-34; Hallikas et al., 2006, *Cell* 124 (1):47-59).

In one aspect of this invention, a GLI1, GLI2, or GLI3 down-stream gene is identified. According to the present invention, identification of a GLI1, GLI2, or GLI3 down-stream gene is performed by DNA sequencing of the promoter and/or enhancer region of a gene suspected to be regulated by GLI1, GLI2, or GLI3. It is expected that a GLI1, GLI2, or GLI3 down-stream gene is also expressed or over-expressed in cancers wherein GLI1, GLI2, or GLI3 is expressed or over-expressed. GLI down-stream genes having a GLI DNA binding site can also be identified by fragmenting a genome and use the resulting fragments as probes in gel shift assay as known in the art. Any fragment identified in such an assay can be amplified, identified and/or used as a nucleic acid probe to screen for and identify the gene from where it originated, by e.g., screening a genomic DNA library as known in the art. An alternative method for identifying GLI binding sites in mammalian enhancer elements and, thus, GLI target genes is the enhancer element locator (EEL; Hallikas et al., 2006, Cell 124:47-59). For example, Hallikas et al. identified several enhancer elements with two or more GLI binding sites that are conserved in mouse to human and rat to human alignments. These enhancer elements are associated with the GLI target genes, such as exocyst complex component Sec5 (SEC5L1), NULL (NM_018271; NM_144962), early growth response protein 3 (EGR-3) (zinc finger protein pilot) (EGR3), PR-domain zinc finger protein 10 (PRDM10), T-box transcription factor TBX2 (T-box protein 2; TBX2), SOX-13 protein (type 1 diabetes autoantigen ICA12) (islet cell antigen 12) (SOX13), patched protein homolog 1 (PTC1) (PTC) (PTCH), and protein related to DAN and Cerberus (NM_022469). A small molecule compound of the present invention thus, can be used to inhibit expression of any of these target genes.

Thus, in one embodiment of the present invention, a GLI down-stream gene having a GLI DNA binding site, preferably a GLI1, GLI2, or GLI3 DNA binding site, operably linked to its promoter and/or enhancer sequence is inhibited. Inhibition of the down-stream gene is achieved by using a method of the present invention for inhibiting GLI signaling. Specifically, this invention provides a method for inhibiting the expression of a GLI3 down-stream gene, comprising the step of administering to a cell expressing a GLI3 down-stream gene a small molecule compound of the present invention, wherein said administering results in inhibition of expression of the GLI3 down-stream gene. Optionally, this method includes the step of verifying inhibition of the GLI3 down-stream gene. This can be done using methods in the art, such as RT-PCR or Western blot analysis.

In addition to the GLI target genes identified by Hallikas et al., (Hallikas et al., 2006, Cell 124:47-59), this invention also identified the Wnt2 gene as a GLI target gene, i.e., having a GLI DNA binding site (see Examples herein). Thus, in one embodiment of the invention the down-stream gene is a Wnt gene, preferably a Wnt-2 gene and more preferably a human Wnt2 gene. In this embodiment, inhibition of GLI3 signaling leads to inhibition or down-regulation of Wnt-2 as well as the Wnt-2 signaling. Inhibition of Wnt-2 signaling affects, for example expression of Dvl and beta-catenin as described in U.S. patent application Ser. Nos. 10/678,639 and 11/131,425.

GLI3 functions upstream of GLI1 and GLI2 and also seems to regulate transcription of the Gli1 and Gli2 genes through binding to a GLI3 DNA binding site within the promoter/enhancer regions of the Gli1 and Gli2 genes. Thus, signaling by GLI3, GLI1 and GLI2 is not in parallel, but rather within the same signaling pathway. Thus, in one embodiment of the present invention, the down-stream gene is a Gli1 gene, preferably a human Gli1 gene. In this embodiment, inhibition of GLI3 signaling leads to inhibition or down-regulation of Gli1 expression as well as the GLI1 signaling.

In another embodiment of the present invention, the down-stream gene is a Gli2 gene, preferably a human Gli2 gene. In this embodiment, inhibition of GLI3 signaling leads to inhibition or down-regulation of Gli2 expression as well as the GLI2 signaling.

E. Inhibiting the Activity of a GLI Polypeptide

GLI polypeptides have several biological activities as described herein. In one aspect of the present invention, a method for inhibiting the activity of a GLI polypeptide, preferably a GLI1, GLI2, or GLI3 polypeptide, is provided. This method comprises the step of contacting a GLI polypeptide with a small molecule compound of the invention thereby inhibiting the activity of the GLI polypeptide. In another embodiment of the present invention, this method comprises the step of contacting a cell expressing a GLI polypeptide with a small molecule compound of the invention thereby inhibiting the activity of the GLI polypeptide.

For example, GLI polypeptides are transcriptional activator proteins and typically exert their transcriptional activation potential through binding to or interaction with a TBP-Associated Factor (TAF). Thus, in one aspect of the present invention, a method for inhibiting the activity of a GLI polypeptide, preferably a GLI1, GLI2, or GLI3 comprises the step of contacting a GLI polypeptide with a small molecule compound of the invention thereby inhibiting binding of the GLI polypeptide to a TAF or interaction of the GLI polypeptide with a TAF. In another embodiment of the present invention, this method comprises the step of contacting a cell expressing a GLI polypeptide with a small molecule compound of the invention thereby inhibiting binding of the GLI polypeptide to a TAF or interaction of the GLI polypeptide with a TAF.

GLI polypeptides are transcriptional activator proteins and typically exert some of their transcriptional activation potential through binding to or interaction with a co-activator, such as CBP. Thus, in one aspect of the present invention, a method for inhibiting the activity of a GLI polypeptide, preferably a GLI1, GLI2, or GLI3 comprises the step of contacting a GLI polypeptide with a small molecule compound of the invention whereby the binding of the GLI polypeptide to a co-activator or interaction of the GLI polypeptide with a co-activator is inhibited. In another embodiment of the present invention, this method comprises the step of contacting a cell expressing a GLI polypeptide with a small molecule compound of the invention thereby inhibiting binding of the GLI polypeptide to a co-activator or interaction of the GLI polypeptide with a co-activator.

As described herein, GLI polypeptides are transcriptional activator proteins and typically exert their transcriptional activation potential through binding to a GLI DNA binding site. Thus, in another aspect of the present invention, a method for inhibiting the activity of a GLI polypeptide, preferably a GLI1, GLI2, or GLI3 polypeptide, comprises the step of contacting a GLI polypeptide with a small molecule compound of the invention thereby inhibiting binding of the GLI polypeptide to a GLI DNA binding site. In another embodiment of the present invention, this method comprises the step of contacting a cell expressing a GLI polypeptide with a small molecule compound of the invention thereby inhibiting binding of the GLI polypeptide to a GLI DNA binding site.

Inhibition of the activity of the GLI polypeptide can be in vitro or in vivo.

F. Use of Small Molecule Compounds in the Manufacture of a Pharmaceutical Composition or a Medicament Another aspect of the invention provides for the use of a small molecule compound of the present invention in the manufacture of a pharmaceutical composition or a medicament for the therapeutic and/or prophylactic treatment of a condition, e.g., cancer wherein a GLI polypeptide, preferably a GLI3 polypeptide, is expressed.

In another embodiment, the present invention provides for the use of a small molecule compound in the manufacture of a pharmaceutical composition or medicament for inducing apoptosis in a cancer cell, wherein the cancer cell expresses a GLI polypeptide, preferably a GLI3 polypeptide.

In another related aspect, the invention provides for the use of a small molecule compound in the manufacture of a pharmaceutical composition or medicament for use in combination with another chemotherapeutic anticancer agents for the treatment of a cancer expressing a GLI polypeptide, preferentially a GLI3 polypeptide. Pharmaceutical composition and medicaments provided by the present invention are described herein.

G. Screening for Modulators of GLI Protein Activity

Inhibitors and activators, referred to herein as modulators of GLI protein activity are identified using methods known in the art and described herein. A number of different screening protocols can be utilized to identify additional compounds than those described herein that modulate the activity of a GLI polypeptide. The term "modulate" encompasses an increase or a decrease in the measured activity of a GLI polypeptide when compared to a suitable control.

These screening protocols can be used in cells, particularly mammalian cells, and especially human cells. And even more preferred in human cancer cells. In general terms, the screening methods involve screening a variety of compounds to identify a compound that modulates activity of a GLI polypeptide. The method generally comprises the step of (a) contacting a candidate compound with a GLI polypeptide, with a sample comprising a GLI polypeptide or a mammalian cell expressing a GLI polypeptide; and (b) assaying an activity of the GLI polypeptide in the presence of the candidate compound. An increase or a decrease in the activity measured in comparison to the activity of the GLI polypeptide in a suitable control (e.g., a GLI polypeptide in the absence of the candidate compound, a sample comprising a GLI polypeptide in the absence of the candidate compound or a mammalian cell expressing a GLI polypeptide in the absence of the candidate compound) is an indication that the candidate compound modulates an activity of the GLI polypeptide. Once a candidate compound or candidate agent has been identified in one of the screening methods of the present invention, it is typically referred to as a compound or as an agent, rather than a candidate compound or candidate agent.

Compounds that increase or decrease a GLI polypeptide activity to a desired extent may be selected for further study, and assessed for cellular availability, pharmacokinetic analysis, cytotoxicity, biocompatibility, etc.

In a preferred aspect, the screening methods involve screening candidate compounds to identify a compound that inhibits or reduces the activity of a GLI polypeptide. In another aspect, the screening methods involve screening candidate compounds to identify a compound that increase the activity of a GLI polypeptide.

In one aspect, the present invention provides a method for identifying a compound that modulates a GLI protein activity. A preferred method of this invention is a method for identifying a candidate compound capable of modulating the protein-protein interaction between a GLI protein and a $TAF_{II}31$ protein. In one embodiment, this method comprises the steps of contacting a candidate compound with a sample comprising a GLI protein and a $TAF_{II}31$ protein; and determining the binding of the GLI-protein to the $TAF_{II}31$ protein. A reduced binding of the GLI protein to the $TAF_{II}31$ in the presence of the candidate compound compared to the binding of the GLI protein to the $TAF_{II}31$ in the absence of the candidate compound indicates that the candidate compound is capable of inhibiting the interaction between the GLI protein and the $TAF_{II}31$ protein. An increased binding of the GLI protein to the $TAF_{II}31$ in the presence of the candidate compound compared to the binding of the GLI protein to the $TAF_{II}31$ in the absence of the candidate compound indicates that the candidate compound is capable of increasing the interaction between the GLI protein and the $TAF_{II}31$ protein.

In one embodiment, the GLI protein activity is GLI protein dependent transcription activity and the method is for identifying a compound that modulates GLI protein dependent transcription activity. The method comprises the steps of contacting a sample with a candidate compound, wherein the sample comprises an expression reporter construct having one or more GLI DNA binding sites operably linked to a reporter gene; and determining the effect, if any, of the candidate compound on the level of GLI protein dependent transcription activity.

Many reporter genes as known in the art may be used. Suitable reporter genes include, but are not limited to luciferase, CAT (chloramphenicol-acetyltransferase), GFP (green fluorescent protein), and β-Gal (beta-galactosidase).

Using, e.g., the binding assays described herein, such as immunoprecipitation assays and transcription assays (see, e.g., Examples 35), the modulation of binding of a GLI polypeptide to a $TAF_{II}31$ protein in the absence or presence of an candidate compound, can be assessed. In principle assays described herein can be employed in screening protocols wherein the small molecule compounds analyzed in these assays are replaced by candidate compounds to be tested.

As described herein, inhibiting a GLI protein activity can lead to apoptosis of cancer cells. Thus, in yet another aspect of the present invention, a method for identifying a candidate compound for inducing apoptosis is provided. In a preferred embodiment of this method, the method comprises the steps of (a) contacting a GLI polypeptide with a candidate compound, and (b) determining whether the candidate compound binds to the GLI polypeptide, inhibits an activity of the GLI polypeptide; wherein a candidate compound that binds to the GLI polypeptide or inhibits an activity of the GLI polypeptide is a candidate compound useful for inducing apoptosis.

Optionally, the methods for identifying a candidate compound as described herein, comprise the step of selecting the compound that binds to a GLI polypeptide or modulates the activity of the GLI polypeptide.

Candidate compounds useful for inducing apoptosis identified by the method described herein can be assessed by using the apoptosis assay described herein and assays known in the art.

A candidate compound is assessed for any cytotoxic activity it may exhibit towards normal cells (e.g., non-cancer cells), using well-known assays, such as trypan blue dye exclusion, an MTT ([3-(4,5-dimethylthiazol-2-yl)-2,5-d-iphenyl-2H-tetrazolium bromide]) assay, and the like. Compounds that do not exhibit cytotoxic activity are considered candidate compounds.

a) Screening for Compounds

In addition to the screening methods described above and the assays described herein, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); see also Dalton and Treisman, 1992, *Cell* 68: 597-612; Fields and Sternglanz, 1994, *Trends Genet* 10:286-92).

In the two-hybrid system, for example, a GLI polypeptide, is fused to an SRF-binding region or GAL4-binding region and expressed in yeast cells. A $TAF_{II}31$ polypeptide that binds to the GLI polypeptide is fused to the VP16 or GAL4 transcriptional activation region and also expressed in the yeast cells. Alternatively, the $TAF_{II}31$ polypeptide that binds to the GLI polypeptide may be fused to the SRF-binding region or GAL4-binding region, and the GLI polypeptide to the VP16 or GAL4 transcriptional activation region. When the test compound does not inhibit the binding between GLI polypeptide and $TAF_{II}31$ polypeptide, the binding of the two activates a reporter gene, making positive clones detectable. As a reporter gene, for example, Ade2 gene, lacZ gene, CAT gene, luciferase gene and such can be used besides HIS3 gene. Alternatively, when the test compound does inhibit the binding between GLI polypeptide and $TAF_{II}31$ polypeptide, the non-binding of the two polypeptides is also detectable (e.g., no expression of the lazZ gene results in white yeast colonies, while expression of the lacZ gene results in blue colonies).

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, 1997, *Anticancer Drug Des.* 12:145). Examples of methods for the synthesis of molecular libraries can be found in the art (DeWitt et al., 1993, *Proc Natl Acad Sci USA* 90: 6909; Erb et al., 1994, *Pro. Natl Acad Sci USA* 91:11422; Zuckermann et al., 1994, *J Med Chem* 37:2678; Cho et al., 1993, *Science* 261:1303; Carell et al., 1994, *Angew Chem Int. Ed Engl.* 33:2059; Carell et al., 1994, *Angew Chem Int Ed. Engl.* 33:2061; Gallop et al., 1994, *J Med Chem* 37:1233). Libraries of compounds may be presented in solution (see Houghten, 1992, *Bio/Techniques* 13:412) or on beads (Lam, 1991, *Nature* 354: 82), chips (Fodor, 1993, *Nature* 364:555), bacteria (U.S. Pat. No. 5,223,409), spores (U.S. Pat. Nos. 5,571,698; 5,403,484, and 5,223,409), plasmids (Cull et al., 1992, *Proc Natl Acad Sci USA* 89:1865) or phage (Scott and Smith, 1990, *Science* 249:386; Devlin, 1990, *Science* 249:404; Cwirla et al., 1990, *Proc Natl Acad Sci USA* 87:6378; Felici, 1991, *J Mol Biol* 222 301; US Pat. Application 20020103360). The test compound exposed to a cell or protein according to the screening methods of the present invention may be a single compound or a combination of compounds. When a combination of compounds is used in the screening methods of the invention, the compounds may be contacted sequentially or simultaneously.

A compound isolated by the screening methods of the present invention is a candidate for drugs which modulate the activity of a GLI polypeptide, for inducing apoptosis, and for treating or preventing a pathological condition, such as cancer, as described herein. A compound in which a part of the structure of the compound obtained by the present screening methods of the present invention is converted by addition, deletion and/or replacement, is included in the compounds obtained by the screening methods of the present invention.

Both naturally occurring GLI polypeptides and recombinant GLI polypeptides can be used to practice the methods of the present invention.

Methods for testing and assaying compounds, agents, or antagonists identified by methods described herein, are provided herein and involve a variety of accepted tests to determine whether a given compound, agent, or small molecule compound is useful to practice a method of the present invention. Methods of the present invention may optionally comprise the step of detecting a nucleic acid, such as a mRNA (e.g., by nucleic acid hybridization or PCR), a polypeptide (e.g., by Western blotting, immunological assay, or mass spectrometry), an enzymatic activity (e.g., enzymatic activity of a reporter gene product, such as luciferase), or inducing or inhibiting apoptosis. These detection methods are well known in the art.

VI. Kits

For use in diagnostic, research, and therapeutic applications suggested above, kits are also provided by the invention. In the diagnostic and research applications such kits may include any or all of the following: assay reagents, buffers, a small molecule compound of the present invention, a GLI polypeptide, a Gli nucleic acid, an anti-GLI antibody, hybridization probes and/or primers, Gli expression constructs, etc. A therapeutic product may include sterile saline or another pharmaceutically acceptable emulsion and suspension base.

In addition, the kits may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

A wide variety of kits and components can be prepared according to the present invention, depending upon the intended user of the kit and the particular needs of the user.

In a preferred embodiment of the present invention, the kit is a pharmaceutical kit and comprises a pharmaceutical composition comprising (i) a small molecule compound, preferably FN1-5 or FN1-8 and (ii) a pharmaceutical acceptable carrier. Pharmaceutical kits optionally comprise an instruction stating that the pharmaceutical composition can or should be used for treating a cancer expressing a GLI polypeptide or Gli nucleic acid, preferably a GLI3 polypeptide or Gli3 nucleic acid.

The kits according to the present invention may further comprise a reagent for performing mass spectrometry. Such reagents are well known to those skilled in the art and include, for example, a probe or a chip.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

All publications, patents and patent applications cited in this specification are herein incorporated in their entireties by reference as if each individual publication, patent or patent application were specifically and individually indicated to be incorporated by reference.

As can be appreciated from the disclosure above, the present invention has a wide variety of applications. The invention is further illustrated by the following examples, which are only illustrative and are not intended to limit the definition and scope of the invention in any way.

VII. Examples

Example 1

General Methods

A. Cell Lines

Most human cell lines were obtained from the American Type Culture Collection (A.T.C.C.; Manassas, Va.). These cell lines include: non-small cell lung cancer (NSCLC) cells A549, H1703, H460, H358, H322, H838, H1299, H1650, H1975, and A427; mesothelioma cells 211H, H513, H2052, H28, and Met5A; colon cancer cells SW480, HCT116, HT29, Lovo, and CaCO2; breast cancer cells MCF7, HuL100, SKBR-3 and BT474; sarcoma MG-63, MNNG, A-204, and SJSA-1; melanoma cells LOX, FEM, FEMX, A375, G361, SK-Mel-2, SK-Mel-5, SK-Mel-28, and Malme-3M; human normal skin fibroblast cell, Malme-3; renal cell carcinoma cells 786-O, Caki, 769-P, A704, and OMRC3; prostate cancer cell line LnCAP; glioma cell line U87; hepatocellular carcinoma cells HepG2 and SK-Hep-1; normal muscle cell lines; normal renal cell line HRE152 and HK-2. Other human mesothelioma cancer cell lines H290 and MS-1 were obtained from the National Institute of Health (NIH, Frederick, Md.), and LRK1A and REN was kindly provided by Dr. Steven Albelda's laboratory at the University of Pennsylvania (Philadelphia, Pa.). Normal mesothelial cell line LP-9 was obtained from the Cell Culture Core Facility at Harvard University (Boston, Mass.). Human pancreatic cancer cell lines BxPC3, Panc4.21, CFPAC-1, and L3.6sl were kindly provided by Dr. Matthias Hebrok's laboratory at the University of California, San Francisco (San Francisco, Calif.). Human nasopharyngeal carcinoma cell lines HNE-1 and HONE-1 were kindly provided by Dr. Ronald Glaser at the Ohio State University (Columbus, Ohio). Human gastric cancer cell lines, NUGC3, MNK28, and AGS were kindly provided by Dr. Xin Chen at the University of California, San Francisco (San Francisco, Calif.); esophageal cancer cell lines SEG-1, TE-7, BIC-1 and OE21 were kindly provided by Dr. Michael Korn at the University of California, San Francisco, (San Francisco, Calif.); ovarian cancer cell line AZ23247 was kindly provided by Dr. Karen Smith-McCune at the University of California, San Francisco (San Francisco, Calif.).

Most cell lines were routinely cultured in RPMI 1640 supplemented with 10% fetal bovine serum, penicillin (100 IU/ml) and streptomycin (100 ug/ml), except, LP-9 was cultured in M199 containing 15% CS plus 10 ng/ml of EGF plus 0.4 μg/ml of HC; ovarian cancer cell line AZ23247 was cultured in M15 medium supplemented with 10% fetal bovine serum (UCSF Cell Culture Facility); the normal renal cell line HRE152 was cultured in alphaMEM supplemented with 10% fetal bovine serum, penicillin (100 IU/ml) and streptomycin (100 ug/ml); and normal human small airway epithelial cells (SAEC) and bronchial epithelial cells (NHBE) (primary cultures) obtained from Clonetics (Walkersville, Md.) were cultured in Clonetics SAG™ Bullet Kit. All cell lines were cultured at 37° C. in a humid incubator with 5% $CO_2$.

B. Tissue Samples

Fresh cancer tissue and adjacent normal tissue from patients undergoing curative primary resection of their tumors were collected at the time of surgery (IRB approval H8714-15319-040), and immediately snap-frozen in liquid nitrogen. These tissue samples were kept at −170° C. in a liquid nitrogen freezer until further use. Primary tissue cultures were prepared as follows: Fresh cancer tissue was obtained with consent from patients undergoing resection, cut into small pieces (1-2 mm in diameter), and then digested with Collagenase A (Roche Applied Science, Indianapolis, Ind.) at room temperature for 2 hours according to manufacture's protocol. Single cells from the digestion were spun down and the cell pellets were washed twice using RPMI 1640 supplemented with 10% fetal bovine serum, penicillin (100 IU/ml) and streptomycin (100 μg/ml). Then, the cells were resuspended in the same medium and cultured in 6-well plates at 37° C. in a humid incubator with 5% $CO_2$ until they were ready for further treatments.

C. Cell Survival Assay (Cell-Based Cytotoxicity Assay)

Typically, the small molecule compounds of the present invention were dissolved in DMSO at a concentration of 30 mM. The small molecule compounds were then tested under cell culture conditions at different concentrations ranging from 0, 10, 30, 50, to 100 uM. To determine cell survival after treatment, the cells were incubated with the small molecule compounds in 6-well plates for about 3 days. After removal of the cell culture medium, 1-ml of 0.5% crystal violet solution (prepared in 20% ethanol and 20% methanol) was added to stain the cells for 5 min. Then the crystal violet solution was rinsed clean with tap water. Cell survival was estimated based on the density of crystal stained plates.

Another assay for determining the number of viable cells in proliferation or cytotoxicity assays is the MTS assay, a calorimetric method. MTS assay reagents are commercially available (Promega Corp., Madison, Wis.). The reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution. The MTS tetrazolium compound (Owen.s reagent) is bioreduced by cells into a colored formazan product that is soluble in tissue culture medium. This conversion may be accomplished by NADPH or NADH produced by dehydrogenase enzymes in metabolically active cells. The quantity of formazan product as measured by the absorbance at 490 nm is directly proportional to the number of living cells in culture. Because the MTS formazan product is soluble in tissue culture medium, this assay requires fewer steps than procedures that use tetrazolium compounds such as MTT. The formazan product of MTT reduction is a crystalline precipitate that requires an additional step in the procedure to dissolve the crystals before recording absorbance readings at 570 nm.

D. Apoptosis Analysis

Apoptosis was analyzed by using an Annexin V FITC Apoptosis Detection Kit (Biosource, Camarillo, Calif.), according to the manufacturer's protocol. After treatment with different small molecule compounds at various concentrations for about 3 days, cells were harvested by trypsinization, stained and immediately analyzed by flow cytometry (FACScan; Decton Dickinson, Franklin Lake, N.J.). Early apoptotic cells with exposed phosphatidylserine but intact cell membranes will bind to Annexin V-FITC, but not propidium iodide (PI). Cells in necrotic or late apoptotic stages will be labeled with both Annexin V-FITC and PI. "% apoptotic cells" or "% apoptosis" refers to the combined early and late apoptotic cells.

E. Semi-Quantitative RT-PCR

Total RNA from cell lines or tissue samples was isolated using Qiagen RNeasy Mini Kit (Valencia, Calif.). RT-PCR was performed in GeneAmp PCR system 2700 (Applied Biosystems, Foster City, Calif.) using One-step RT-PCR Kit from Invitrogen Life Technologies (Carlsbad, Calif.). Primers for RT-PCR were obtained from Operon Technologies Inc. (Alameda, Calif.). Primer sequences for amplifying different genes in Hedgehog and Wnt signaling pathways are listed in the table below (Table 1; F, forward primer; R, reverse primer). The expected size of the PCR product is indicated for each primer pair. GAPDH was used as internal control.

TABLE 1

Primer sequences for semi-quantitative RT-PCR

| Gene | Primer sequences | Size (bp) |
|---|---|---|
| Gli1 | F: 5'-TACTCACGCCTCGAAAACCT-3'<br>R: 5'-GTCTGCTTTCCTCCCTGATG-3' | 340 |
| Gli2 | F: 5'-CACCAACCAGAACAAGCAGA-3' | 246<br>(alpha & gamma) |
|  | R: 5'-ACCTCAGCCTCCTGCTTACA-3' | 195<br>(beta & delta) |
| Gli3 | F: 5'-GGCCATCCACATGGAATATC-3'<br>R: 5'-TGAAGAGCTGCTACGGGAAT-3' | 196 |
| Shh | F: 5'-CAGTGGCCAGGAGTGAAACT-3'<br>R: 5'-CCAGGAAAGTGAGGAAGTCG-3' | 380 |
| Ptch1 | F: 5'-CGCCTATGCCTGTCTAACCATGC-3'<br>R: 5'-TAAATCCATGCTGAGAATTGCA-3' | 448 |
| Wnt-2 | F: 5'-GGGAATCTGCCTTTGTTTATGCCA-3'<br>R: 5'-GAACCGCTTTACAGCCTTCCTGCC-3' | 289 |
| Dvl-3 | F: 5'-GCTAAATGGAACTGCGAAGG-3'<br>R: 5'-CCGCTTGTGTCTTCTCATCA-3 | 187 |
| GAPDH | F: 5'-ATGGGGAAGGTGAAGGTCGG-3'<br>F: 5'-GACGGTGCCATGGAATTTGC-3' | 180 |

F. Transient Transfection of cDNA Constructs

For transient transfection experiments, cells ($2\times10^5$) were plated in six-well plates using growth medium without antibiotics 24 hrs before transfection. Lipofectamine™ 2000 (Invitrogen Life Technologies; Carlsbad, Calif.) was used to mediate transfection using 2.0 μg of cDNA in pCDNA3 vector or 2.0 μg empty pCDNA3 vector as control, according to the manufacturer's protocol. Then the transfected cells were cultured at 37° C. in a humid incubator with 5% $CO_2$ until they were ready for analysis. Gli2 cDNA was kindly provided by Dr. Fritz Aberger at University of Salzburg (Salzburg, Austria). Gli1 and Gli3 cDNA were kindly provided by Dr. Bert Vogelstein and Dr. Kenneth W. Kinzler at the Sidney Kimmel Comprehensive Cancer Center of the Johns Hopkins University (Baltimore, Md.). $TAFI_{II}31$ cDNA was kindly provided by Dr. Gregory L. Verdine at Harvard University (Cambridge, Mass.).

G. Promoter Activity Analysis

One day before transfection, cells ($1\times10^5$) were plated in 12-well plates with growth medium without antibiotics.

When cells reached 80-90% of confluence they were co-transfected using 0.5 µg of each promoter construct in pGL3Basic vector and 0.025 µg pRL-TK Vector (Promega; Madison, Wis.) containing Renilla Luciferase as an internal control for the transformation efficiency. Lipofectamine 2000™ (Invitrogen Life Technologies) was used to mediate transfection for about 6 hours. Then the medium was replaced with fresh medium containing various small molecule compounds at a concentration of 30 µM, and the resulting cells were cultured for an additional 18-24 hours and subjected to luciferase assay. Briefly, cells were lysed in a lysis buffer and Firefly and Renilla Luciferase activities in cells of each well, were measured using Dual-Luciferase Assay System (Promega) and an illuminometer. The measured luciferase activities were normalized to pRL-TK Vector activity and were given relative to the basal activity of empty pGL3-Basic Vector, which was set to unity. The data shown represent mean values (±S.D.). All measurements were performed in triplicate and repeated in at least three independent experiments. The human Wnt-2 promoter-luciferase construct, the human SOCS3 promoter-Luciferase construct and the human Gremlin promoter-luciferase construct were cloned and characterized in the laboratory of Dr. Jablons at the University of California, San Francisco (San Francisco, Calif.; He et al., *Biochem Biophy Res Comm*, 2003; and unpublished data). The 6GLI-TKO-luciferase construct (containing 6 repeats of consensus GLI DNA binding sequence) was kindly provided by Dr. Matthias Hebrok's laboratory at the University of California, San Francisco (San Francisco, Calif.).

H. TOPFLASH Assay

Cells were plated in 12-well plates. The TOPFLASH or FOPFLASH reporter plasmid (Upstate; Charlottesville, Va.) was transfected transiently into cells as described above. Tcf-mediated gene transcription was determined by the ratio of pTOPFLASH:pFOPFLASH luciferase activity, each was normalized to luciferase activities of the pRL-TK reporter (co-transfected internal control). All experiments were performed in triplicate, and repeated three times.

I. Western Blotting

Whole proteins from cell cultures with or without treatments with small molecule compounds (30 µM for 2-3 days) were prepared using standard protocols (Pierce Biotechnology, Rockford, Ill.). Protein concentrations were measured using Bio-Rad Protein Assay reagent. Whole cell lysate protein (5-20 ug) were boiled for 5 min and separated by 10-20% SDS-PAGE. Proteins were transferred to an Immobilon-P membrane (Millipore Corp., Bedford, Mass.) using semi-dry transfer cell (Bio-Rad; Benicia, Calif.). The membranes were blocked with 5% nonfat milk powder and 0.1% Tween 20 in Tris-buffer saline overnight at 4° C. and then incubated with primary antibody for 1 h at room temperature. Membranes were washed in 5% nonfat milk powder and 0.1% Tween 20 in Tris-buffer saline for three 10-min periods. Horseradish peroxidase-conjugated goat anti-rabbit or donkey anti-mouse antibodies were used as secondary antibodies. Proteins were visualized with chemiluminescence luminol reagents (Santa Cruz Bio-technology). Anti-Dvl-3, and anti-Survivin, antibodies were from Santa Cruz Biotechnology (Santa Cruz, Calif.). Anti-Caspase3 antibody was from Oncogene (Cambridge, Mass.). Anti-β-Actin antibody was from Sigrna-Aldrich Corp. (St. Louis, Mo.). Anti-β-catenin antibody was from Transduction Laboratories (Lexington, Ky.). Anti-Cytochrome c antibody was from BD Biosciences (San Diego, Calif.). For detecting alteration of β-catenin cytosolic extracts were prepared and examined as described previously in the publications from our lab.

J. In Vivo Anti-Tumorigenicity Studies

The small molecule compound FN1-8 was tested in vivo in the mouse xenograft model bearing human cancer cells. Briefly, female athymic nude mice strain NCRNU-M (5-10 weeks old, 20-25 grams in weight; Taconic, Germantown, N.Y.) was maintained in pathogen-free conditions. Three human cancer cell lines: NSCLC H460, melanoma LOX, (both showing Gli3 activation), and colon cancer HT29 (no Gli3 activation, as a negative control), were used. Ten mice were used in each group and injected s.c. with $3 \times 10^6$ cancer cells in the dorsal area in a volume of 100 µl. After inoculation, human cancer cells were allowed to grow in mice for 7 days to become visible tumor nodules. Animals were then injected with small molecule compound FN1-8 at a dose of 50 mg/kg body weight (1 mg/mouse per day). DMSO alone was used as control. The compounds and controls were adjusted in 40 ul volume for i.p. injection in the abdomens of the mice. One mouse was sacrificed within 1 hour after the compound injection (after 6 injections) and its blood was collected. Then mass spectrometry was used to analyze the compound level in the blood sample to confirm the compound absorption into the blood stream of the mice. Injections were performed daily around the same time for 14 days. Tumors were allowed to grow for 1-2 additional weeks after completion of the compound treatments. Tumor size was measured every three days, and tumor volumes were calculated using width (x) and length (y) ($x^2y/2$, where x<y). Data was presented as mean values (±S.D.).

K. TUNEL Staining Analysis of Apoptosis on Tumor Xenografts

At the end of the in vivo experiment, tumors were resected from the mice of different treated groups after sacrificed. Resected tumors were cryo-dissected immediately and the tumor mass of each sample were then measured. TUNEL staining of the tumor specimens was performed using the ApopTag Peroxidase In Situ Oligo Ligation Apoptosis Detection Kit (Chemicon International, Temecula, Calif.) according to the manufacturer's protocol.

L. Histological Examination for Toxicity Evaluation

After the in vivo studies were completed, different organs were resected from mice. These organs included liver, lung, heart, kidney, intestines, ovary, brain, spleen, skin, and muscle. The specimens were fixed in 4% buffered formaldehyde, embedded in paraffin, sectioned, and histologically analyzed by hematoxylin and eosin (HE) staining. The HE stained slides were examined by a mouse pathologist for toxicity evidence from all the organs as compared with DMSO controls.

M. Statistical Analysis

Data shown represent mean values (±S.D.). Unpaired T-Test in the Excel was used for comparing different treatments and cell lines.

Example 2

Mimicking the Peptide FDAII of the Gli3 Transcription Activation Domain

In order to mimic the FDAII motif of the transcriptional activation domain of GLI3 by small molecules the 3D structure of the FDAII was modeled. As suggested by Yoon et al. (1998, *J Biol Chem* 273:3496-3501), the FVAIL motif within the GLI1 polypeptide resulted in an α-helix structure. It was plausible to also model an α-helical structure for the FDAII motif of the GLI3 polypeptide. Thus, an α-helical structure of the FDAII motif of the GLI3 polypeptide was generated and rational chemical design was employed to design small molecule compounds mimicking the structure of this motif. Small molecule compounds comprising a pyrazoline structure were designed. FIG. 3 shows a RMS overlay between the small molecule compound FN1-5 (described herein) and the FDAII motif of the GLI3 polypeptide modeled as an α-helix.

Example 3

Preparation of Small Molecule Compounds a) Preparation of ethyl 1,3,5-triphenyl-4,5-dihydropyrazole-4-carboxylate (FN1-1)

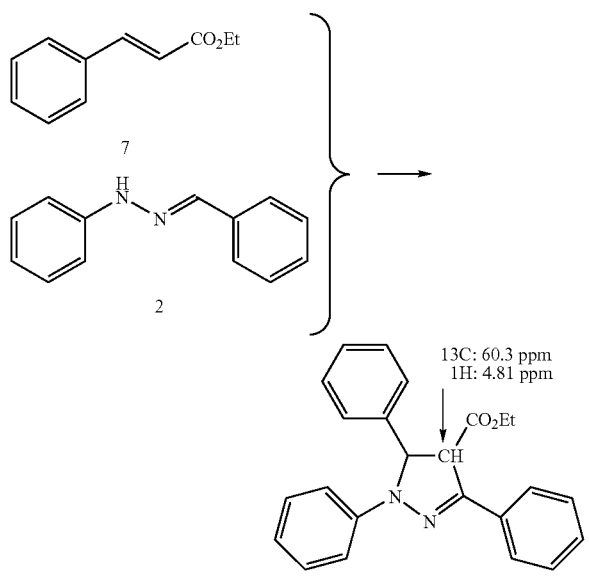

A mixture of ethyl cinnamate (7, 2.55 g), benzaldehyde phenylhydrazone (2, 4.21 g), chloramine-T trihydrate (6.45 g), and methanol (45 mL) were heated under refluxing for 22 hours. The reaction mixture was diluted with 50% ethyl acetate in n-hexanes (400 mL), filtered, and evaporated. The residue was purified by column chromatography (silica gel 200 g, eluent: 0 to 10% ethyl acetate gradient in hexanes) and evaporated to give FN1-1 (8, 1.25 g) as colorless crystal. $^1$H NMR (CDCl$_3$, 400 MHz) δ 7.66-7.64 (m, 1H), 7.46-7.22 (m, 13H), 6.88 (t, J=7.2 Hz, 1H), 4.81 (d, J=4.0 Hz, 1H), 4.70 (d, J=4.0 Hz, 1H), 4.07 (quartet, J=7.2 Hz, 2H), 0.97 (t, J=7.2 Hz, 3H). MS: 371.9 (M+H), 325.5, 297.5.

b) Preparation of 1,3,5-Triphenyl-4,5-dihydropyrazole-4-carboxylic acid (FN1-2)

A mixture of FN1-1 (53 mg), methanol (0.5 mL), 1,4-dioxane (0.5 mL), and 10% (w/v) sodium hydroxide in water (0.1 mL) was kept at the room temperature for 1 hour. The reaction mixture was diluted with water (30 mL) and washed by 30% ethyl acetate in n-hexanes. The aqueous phase was acidified with 2N hydrochloric acid and extracted with ethyl acetate. The extract was washed with water twice (5 mL each) followed by brine (5 mL), dried (Na$_2$SO$_4$), and evaporated to give FN1-2 (38 mg). MS: 297.9 (M–CO$_2$H).

c) Preparation of N-Butyl-1,3,5-triphenyl-4,5-dihydro-pyrazole-4-carboxyamide (FN1-3)

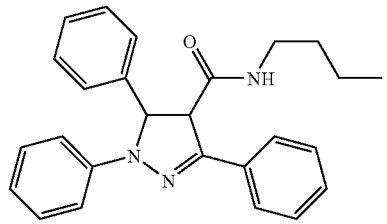

FN1-3 was prepared by a similar manner to that of FN1-5 by using n-butylamine instead of 4-(hydroxyphenyl)ethylamine. MS: 420.9 (M+Na), 398.9 (M+H), 325.5, 297.5.

d) Preparation of N-(5-Hydroxypentyl)-1,3,5-triphenyl-4,5-dihydro-pyrazole-4-carboxyamide (FN1-5)

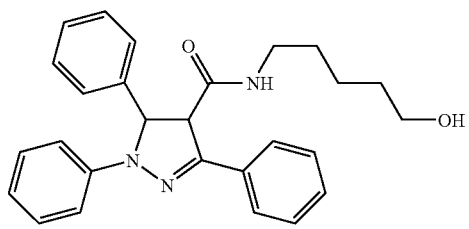

A mixture of FN1-1 (22 mg), 5-aminopentanol (100 microL) and N—N-dimethylformamide (200 microL) were heated at 95° C. for 20 hours. The reaction mixture was diluted with ethyl acetate (10 mL), washed with water twice (5 mL each) followed by brine (5 mL), dried (Na$_2$SO$_4$), and evaporated. The residue was purified by column chromatography (silica gel 10 mL, eluent: 0 to 70% ethyl acetate gradient in hexanes) and evaporated to give FN1-5 (12 mg) as pale yellow amorphous. $^1$H NMR (CDCl$_3$, 400 MHz) δ 7.69-7.67 (m, 1H), 7.34-7.14 (m, 13H), 6.94 (t, J=7.6 Hz, 1H), 6.37 (broad t, 1H), 4.82 (d, J=4.8 Hz, 1H), 4.48 (d, J=4.8 Hz, 1H), 3.53 (t, J=6.4 Hz, 2H), 3.40-3.33 (m, 1H), 3.22-3.14 (m, 1H), 1.56-1.41 (m, 6H). MS: 450.6 (M+Na), 428.6 (M+H), 325.5, 297.5. UVabs max 348 nm (0.05% TFA-MeOH-water 8:2).

e) Preparation of N-(3-Hydroxypropyl)-1,3,5-triphenyl-4,5-dihydro-pyrazole-4-carboxyanide (FN1-7)

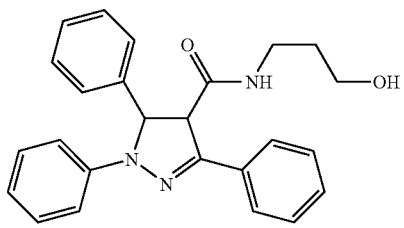

FN1-7 was prepared by a similar manner to FN1-5 by using 3-aminopropanol instead of 4-(hydroxyphenyl)ethylamine. MS: 422.9 (M+Na), 400.9 (M+H), 325.5, 297.5.

f) Preparation of N-(2-(4-Hydroxyphenyl)ethyl)-1,3,5-triphenyl-4,5-dihydro-pyrazole-4-carboxyamide (FN1-8)

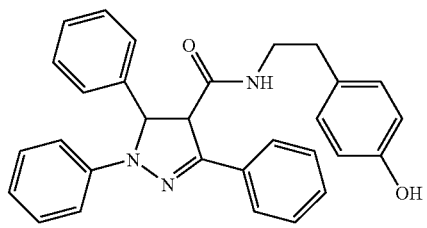

A mixture of FN1-1 (11 mg), 4-(hydroxyphenyl)ethylamine (132 mg) and N—N-dimethylformamide (100 microL) were heated at 95 deg C. for 20 hours. The reaction mixture was diluted with ethyl acetate (10 mL), washed with water twice (5 mL each) followed by brine (5 mL), dried (Na$_2$SO$_4$), and evaporated. The residue was purified by column chromatography (silica gel 10 mL, eluent: 0 to 50% ethyl acetate gradient in hexanes) and evaporated to give FN1-8 (9.5 mg) as pale yellow amorphous. $^1$H NMR (CDCl$_3$, 400 MHz) δ 7.66-7.63 (m, 1H), 7.34-7.16 (m, 14H), 7.07 (d, J=8.4 Hz, 1H), 6.94 (t, J=6.8 Hz, 1H), 6.84 (d, J=8.4 Hz, 1H), 6.52 (d, J=8.4 Hz, 1H), 6.35 (broad t, J=5.6 Hz, 1H), 4.66 (s, 1H), 4.65 (d, J=4.8 Hz, 1H), 4.41 (d, J=4.8 Hz, 1H), 3.56-3.42 (m, 2H), 3.40-3.33 (m, 1H), 2.76-2.57 (m, 2H). MS: 484.5 (M+Na), 462.5 (M+H), 325.5, 297.5. UVabs max 351 nm (0.05% TFA-MeOH-water 8:2).

A preparation of small molecule compound FN1-8 was analyzed by liquid chromatography mass spectrometry and was found to be 90-95% pure (data not shown).

g) Preparation of 5-(1,3,5-Triphenyl-4,5-dihydro-pyrazole-4-carbonyl)aminopentanoic acid (FN1-9U) and 5-(1,3,4-triphenyl-4,5-dihydro-pyrazole-5-carbonyl)aminopentanoic acid (FN1-9S)

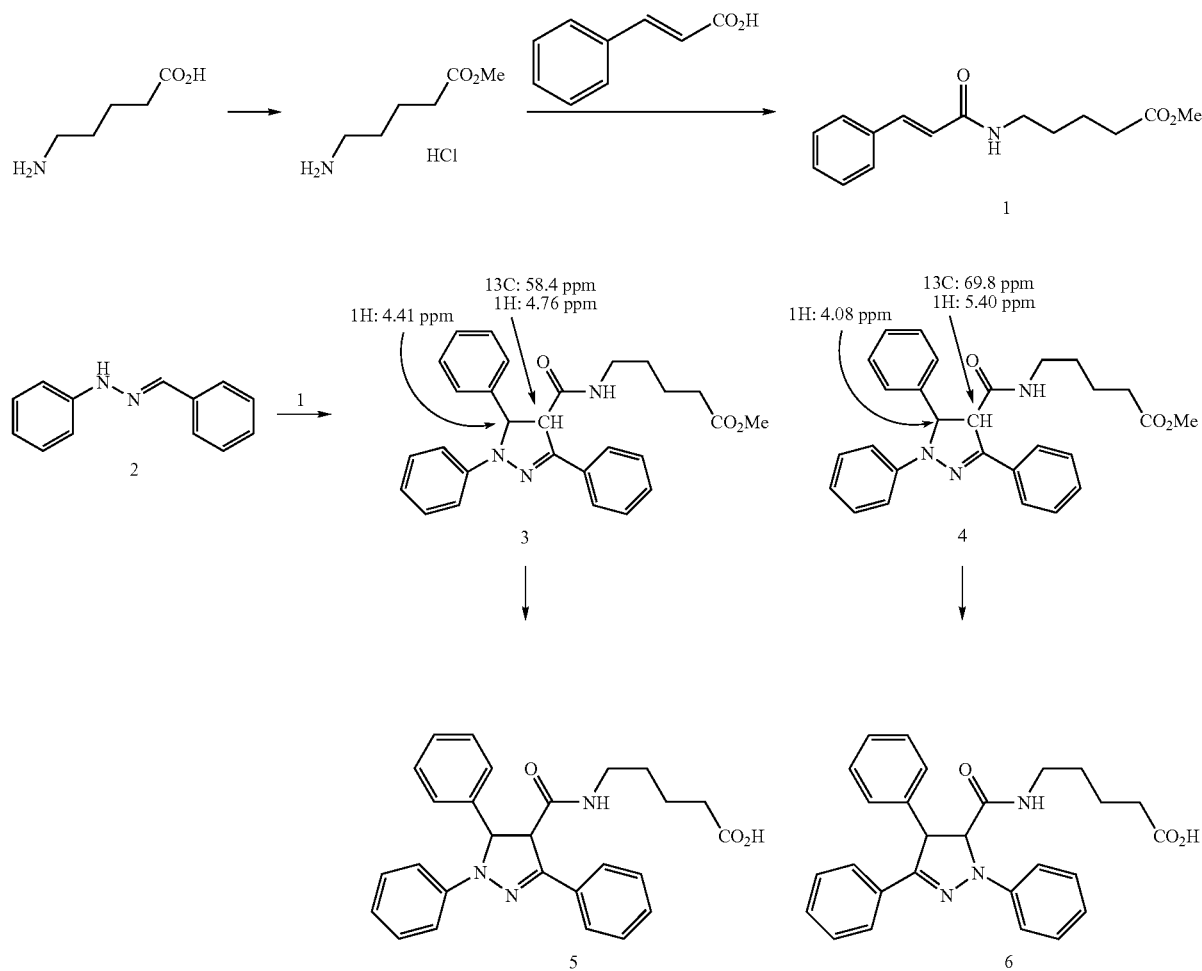

Acetyl chloride (5 mL) was added into methanol (150 mL) to prepare hydrogen chloride in methanol solution, and 5-aminopentanoic acid (1 g) was added. The mixture was kept at the room temperature overnight, and evaporated to isolate methyl 5-aminopentanoate hydrochloride. A mixture of the methyl 5-aminopentanoate hydrochloride (251 mg), cinnamoic acid (74 mg), HBTU (168 mg), diisopropylethylamine (0.87 mL), and dimehylformamide (2 mL) was kept at the room temperature for 1 hour. The reaction mixture was diluted with ethyl acetate (20 mL), washed with water twice (10 mL each) followed by brine (10 mL), dried ($Na_2SO_4$), and evaporated to isolate (4-methoxycarbonyl)butyl cinnamamide (1, 100 mg). A mixture of (4-methoxycarbonyl)butyl cinnamamide (1, 100 mg), benzaldehyde phenylhydrazone (2, 113 mg), chloramine-T trihydrate (160 mg), and methanol (2 mL) were heated under refluxing for 22 hours. The reaction mixture was diluted with 50% ethyl acetate in n-hexanes (40 mL), filtered, and evaporated. The residue was purified by column chromatography (silica gel 20 g, eluent: 0 to 10% ethyl acetate gradient in hexanes) to isolate methyl 5-(1,3,5-triphenyl-4,5-dihydro-pyrazole-4-carbonyl) aminopentanoate (3, 13 mg) and methyl 5-(1,3,4-triphenyl-4,5-dihydro-pyrazole-5-carbonyl)aminopentanoate (4, 103 mg). Regiochemistry of each isomer was identified by 1H- and 13-C NMR chemical shifts of the CH adjacent to the amide carbonyl. 5-(1,3,5-Triphenyl-4,5-dihydro-pyrazole-4-carbonyl)aminopentanoic acid (5, FN1-9U) were obtained from 3 by a standard ester hydrolysis condition as shown in the preparation of FN1-2. MS: 464.9 (M+Na), 442.9 (M+H), 325.8, 297.9. 5-(1,3,4-Triphenyl-4,5-dihydro-pyrazole-5-carbonyl)aminopentanoic acid (6, FN1-9S) were obtained from 4 by a similar manner to the preparation of FN1-2. MS: 464.9 (M+Na), 442.9 (M+H), 325.8, 297.9.

Assignment of regiochemistry for 5 and 6 is well agreed with their ESI-MS fragmentation: i.e., 5 gives bigger decarbonylation peak (m/z=297) than 6 because its beta-ketoimino structure facilitates the decarbonylation.

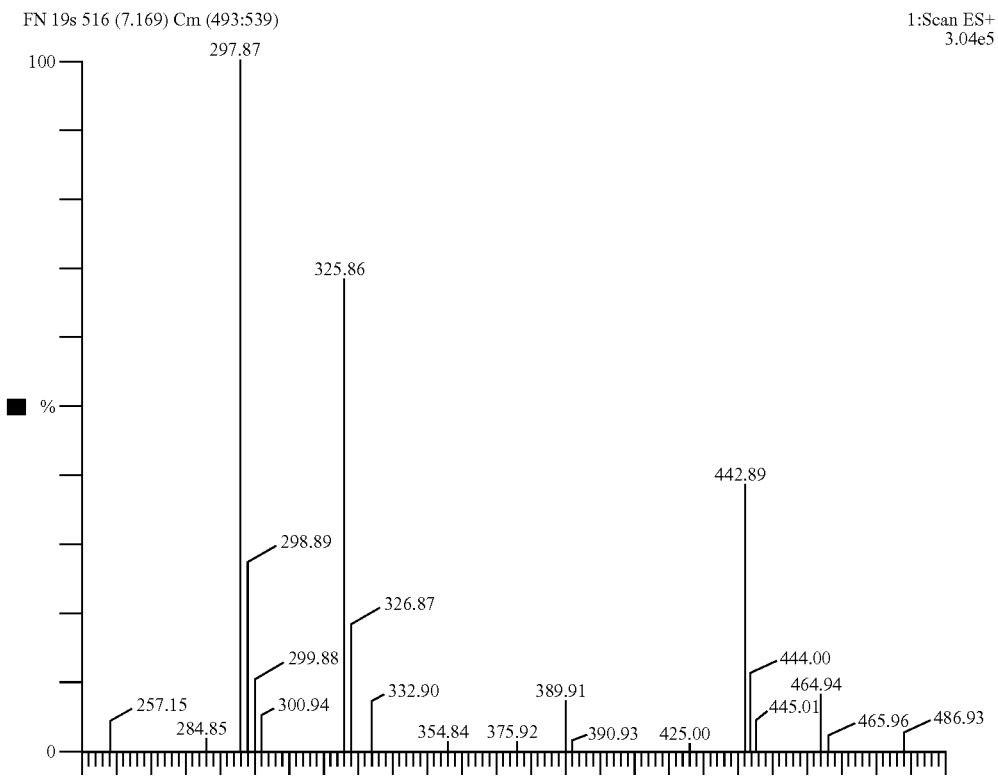

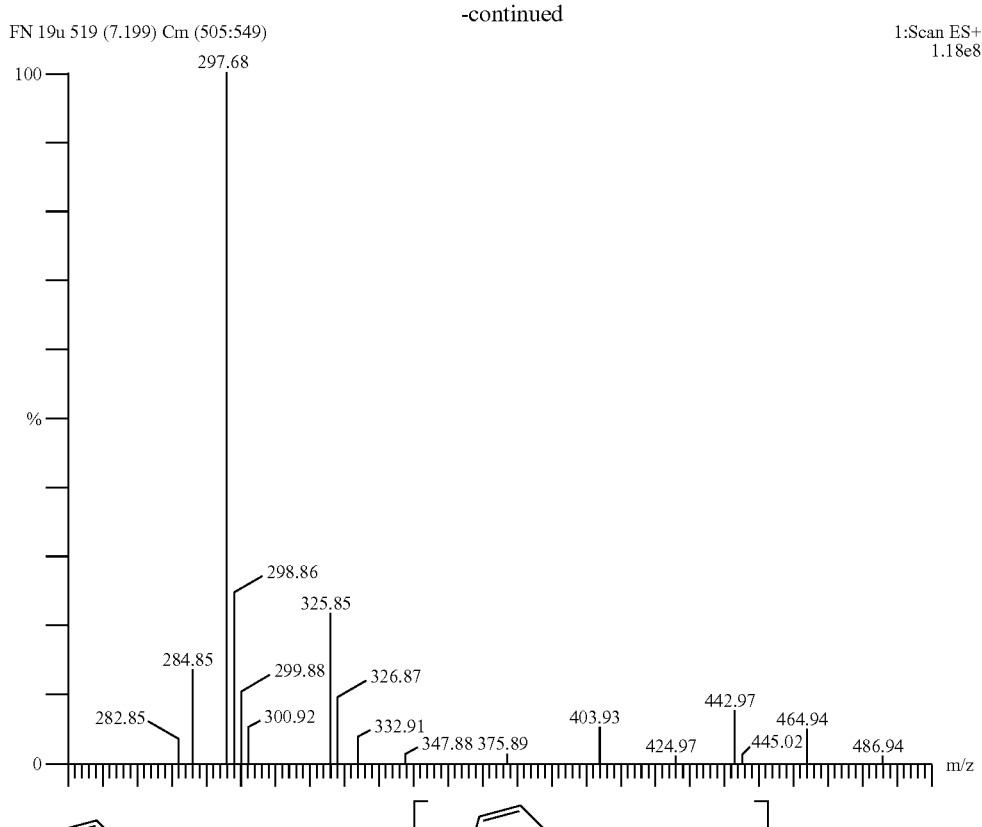

ESI-MS of FN1-9U (upper right panel) and FN1-9S (upper left panel). FN1-9U shows bigger peaks at m/z=297 than that of FN1-9S, because of the decarbonylated fragment formation (bottom panel).

h) Preparation of ethyl 1,3-diphenyl-5-isobutyl-4,5-dihydro-pyrazole-4-carboxylate (FN2-1)

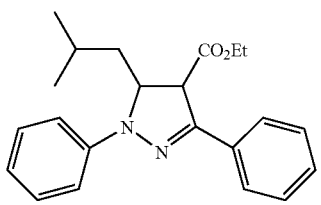

60% Sodium hydride in mineral oil dispersion (0.24 g) was briefly rinsed with n-hexanes to remove the oil, and suspended in dry dimethylformamide (5 mL). The suspension was cooled in an ice-water bath and triethyl phosphonoacetate (1.0 mL) was added. After stirring the mixture for 0.5 hours, 3-methylbutanal (0.65 mL) was added at the ice bath temperature. The mixture was stirred at the room temperature overnight, treated with water (10 mL), extracted with 50% ethyl acetate in n-hexanes (30 mL), washed with water twice (20 mL each) followed by brine (20 mL), dried ($Na_2SO_4$), and evaporated. The residue was purified by column chromatography (silica gel 40 mL, eluent: 0 to 5% ethyl acetate gradient in hexanes) and evaporated to give ethyl 5-methyl-hex-2-enoate as colorless oil. FN2-1 was prepared by a similar manner to FN1-1 by using the ethyl 5-methyl-hex-2-enoate instead of the ethyl cinnamate in Example 2. $^1$H NMR ($CDCl_3$, 400 MHz) δ 7.35-7.29 (m, 3H), 7.25 (dt, J=2.0 Hz, 6.8 Hz, 2H), 7.13 (dd, J=1.6 Hz, 6.4 Hz, 2H), 7.06 (d, J=8.0 Hz, 2H), 6.84 (t, J=7.6 Hz, 1H), 4.52 (d, J=5.6 Hz, 1H), 4.26 (d, J=5.6 Hz, 1H), 4.21 (quartet, J=7.2 Hz, 2H), 2.14 (dd, J=9.2 Hz, 14.8 Hz, 1H), 2.05 (dd, J=5.6 Hz, 15.2 Hz, 1H), 1.95 (double septet, J=2.8 Hz, 6.0 Hz, 1H), 1.21 (t, J=7.2 Hz, 3H), 0.94 (d, J=6.4 Hz, 6H). MS: 351.9 (M+H), 277.9, 194.7.

i) Preparation of N-(5-Hydroxypentyl)-1,3-diphenyl-5-isobutyl-4,5-dihydro-pyrazole-4-carboxyamide (FN2-5)

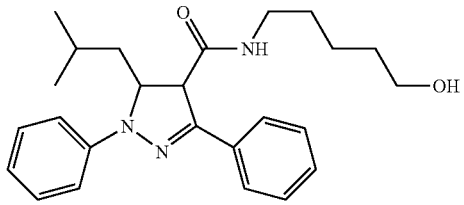

FN2-5 was prepared by a similar manner to FN1-5 by using FN2-1 instead of FN1-1. $^1$H NMR (CDCl$_3$, 400 MHz) δ 7.31-7.25 (m, 5H), 7.09-7.03 (m, 4H), 6.92 (t, J=7.2 Hz, 1H), 6.63 (broad t, J=5.6 Hz, 1H), 4.30 (d, J=6.0 Hz, 1H), 4.20 (d, J=6.0 Hz, 1H), 3.59 (t, J=6.0 Hz, 2H), 3.31 (dd, J=4.4 Hz, 6.8 Hz, 1H), 3.28 (dd, J=4.4 Hz, 6.8 Hz, 1H), 2.12 (dd, J=8.8 Hz, 14.8 Hz, 1H), 2.05 (dd, J=6.0 Hz, 15.6 Hz, 1H), 1.93 (double septet, J=2.4 Hz, 6.8 Hz, 1H), 1.53 (quintet, J=6.4 Hz, 2H), 1.50 (quintet, J=6.4 Hz, 2H), 1.32 (quintet, J=6.4 Hz, 2H), 0.92 (d, J=6.8 Hz, 3H), 0.90 (d, J=6.8 Hz, 3H). MS: 431.0 (M+Na), 409.0 (M+H), 305.9, 277.9.

j) Preparation of N-(5-Hydroxypentyl)-1-phenyl-3,5-bis(isobutyl)-4,5-dihydro-pyrazole-4-carboxyamide (FN3-5)

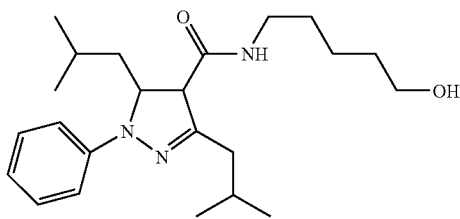

Ethyl 1-phenyl-3,5-bis(isobutyl)-4,5-dihydropyrazole-4-carboxylate was prepared by a similar manner to Example 2 by using ethyl 5-methyl-2-hexanoate instead of the ethyl cinnamate, and using 3-methylbutanal phenylhydrazone instead of the benzaldehyde phenylhydrazone, respectively, in Example 2. FN3-5 was prepared by a similar manner to Example 4 by using the ethyl 1-phenyl-3,5-bis(isobutyl)-4,5-dihydropyrazole-4-carboxylate instead of FN1-1 in Example 4. MS: 411.0 (M+Na), 389.1 (M+H), 285.9, 257.9.

Example 4

Most Cancer Cell Lines Express Gli3

Several cancer cell lines and primary tissue samples were analyzed by semi-quantitative RT-PCR to investigate expression of Gli3. An exemplary analysis of an RT-PCR detecting Gli3 expression is shown in FIG. 2. The cell lines analyzed and found to express detectable levels of Gli3 MRNA included: normal liver (FIG. 2, middle panel, lane 1); NSCLC: H1703, H460 and A549 (FIG. 2, middle panel, lanes 2, 3, 4); breast cancer: HuL100, BT474 and MCF-7 (FIG. 2, middle panel, lanes 5, 6, 7); mesothelioma: Met5A, H290, REN, H513, H28, and 211H (FIG. 2, middle panel, lanes 8-13); colon cancer: SW480 (FIG. 2, middle panel, lane 15); a pair of primary NSCLC tissue samples (FIG. 2, middle panel, lane 16 and 17 are normal and cancer tissues, respectively). LARK1A did not show detectable expression of Gli3 mRNA (FIG. 2, middle panel, lane 14).

In another set of similar RT-PCR experiments Gli3 expression was analyzed and detected in colon cancer cells SW480, Lovo and CaCO2 (FIG. 2, lower panel, lanes 1, 4, 5); normal colon (FIG. 2, lower panel, lane 6); normal renal cell lines: HRE-152 and HK-2 (FIG. 2, lower panel, lanes 7 and 8); renal cell carcinoma: 786-0, Caki, 769-P, A704 and OMRC3 (FIG. 2, lower panel, lanes 9-13); normal lung (FIG. 2, lower panel, lane 14); mesothelioma: REN, H290, 211H, H513, H2052, H28 and MS-1 (FIG. 2, lower panel, lanes 15-21); NSCLC: A549, H460, H838, H1703, H1299, H1650, and H1975 (FIG. 2, lower panel, lanes 22-28). Thus, most cancer cell lines express Gli3. No or low level of Gli3 expression was found in cell lines HCT116 (FIG. 2, lower panel, lane 2), HT29 (FIG. 2, lower panel, lane 3), and A427 (FIG. 2, lower panel, lane 29).

Example 5

Screening of Small Molecule Inhibitors for GLI3 Signaling

Figure 4:
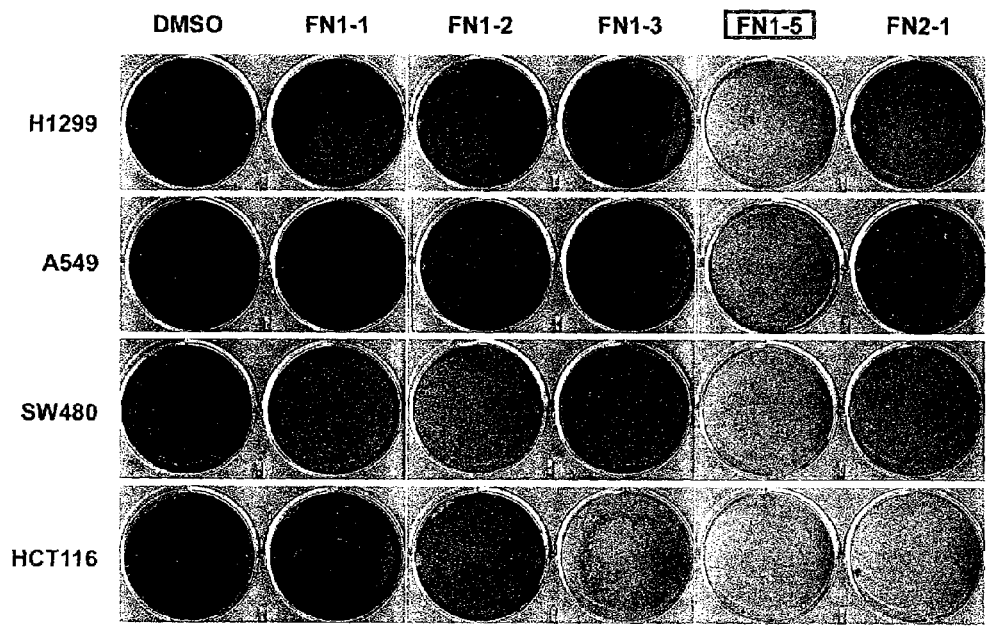
FIG. 4 shows an initial screening of small molecule compounds FN1-1, FN1-2, FN1-3, FN1-5, and FN2-1. The small molecule compounds were designed to inhibit the GLI3 transcription activation (TAF-binding domain). Dramatic killing of all cancer cells tested is observed with small molecule compound FN1-5. DMSO was used as a control. Details are described, e.g., in Example 5.

Initial screening of small molecule compounds of the present invention was performed using the cell-based assays described herein. FIG. 4 shows the result of such an analysis. Two NSCLC cell lines, H1299 and A549, and two colon cancer cell lines, SW480 and HCT116, were incubated with small molecule compounds FN1-1, FN1-2, FN1-3; FN1-5 and FN2-1 at a concentration of 100 μM. DMSO was used as a control. A dramatic cell killing effect was observed for FN1-5 in all cancer cell lines tested (live cells were stained by 0.5% crystal violet). This assay identified the small molecule compound FN1-5 inhibiting GLI transcription activation domain (TAF-binding domain, TAFbd), as an active hit compound.

Figure 6:
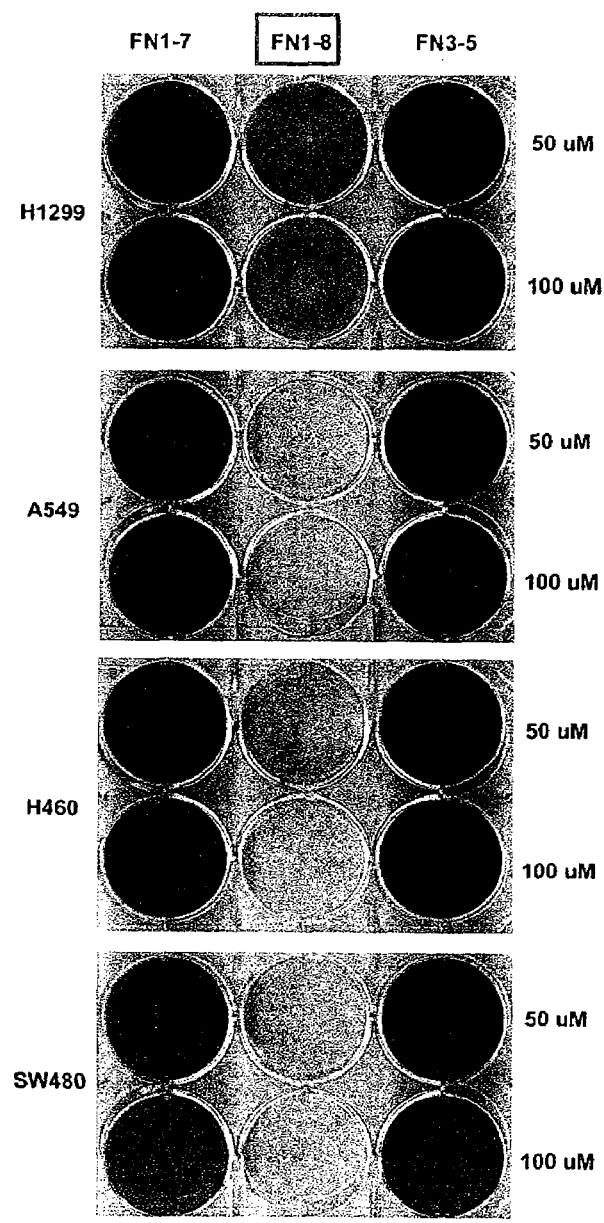
FIG. 6 shows the screening of small molecule compounds FN1-7, FN1-8, and FN3-5 using a cytotoxicity assay and the NSCLC cell lines H1299, A549, and H460, as described herein. Dramatic cell killing was observed in all cancer cells that were treated with small molecule compound FN1-8. Details are described, e.g., in Example 5.

FIG. 6 shows the result of a cytotoxicity assay testing small molecule compounds FN1-7, FN1-8, and FN3-5 on three NSCLC cell lines (H1299, A549, and H460) and one colon cancer cell line (SW480). Cancer cell lines were plated in 6-well plates as described, and incubated with 50, and 100 μM of each compound (stocks were dissolved in DMSO at 30 mM) for 3 days. Dramatic cell killing was observed in all cancer cell lines tested for FN1-8, a modified version of small molecule compound FN1-5. Apoptosis analysis was also carried out by using flow cytometry and the results were consistent (data not shown). Therefore, using the rational design design-screen approach described herein, additional small molecule compound, FN1-8, inhibiting GLI3 transcription activation domain (TAF-binding domain) was identified.

Example 6

Small Molecules FN1-5 and FN1-8 Induce Apoptosis in Colon Cancer Cell Lines CaCO2 and SW480

Figure 5:
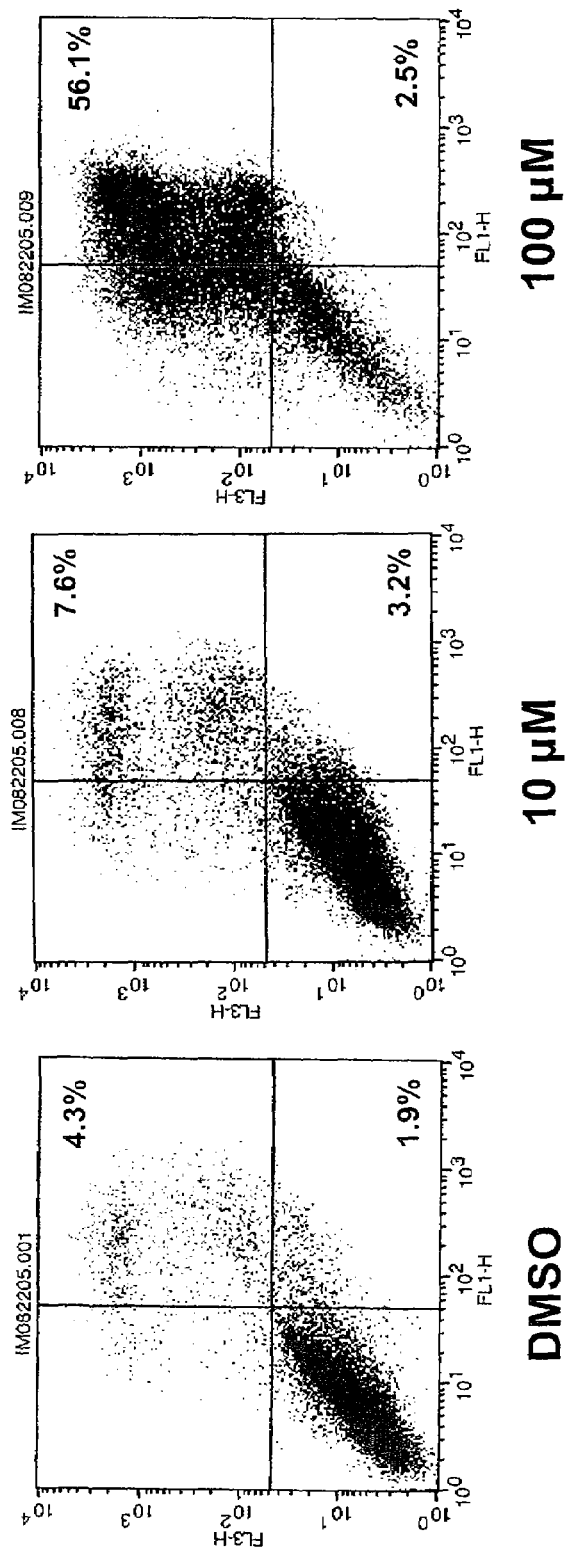
FIG. 5 shows a flow cytometry analysis demonstrating that small molecule compound FN1-5 induces apoptosis in the colon cancer cell line SW480. Significant apoptosis (58.6%) was observed at 100 μM FN1-5, consistent with the staining result. Details are described, e.g., in Examples 5 and 6.

Flow cytometry was used to examine apoptosis in colon cancer cells after treatment of cells with small molecule compounds of the invention. In a representative example, shown in FIG. 5, significant apoptosis (58.6%) in the colon cancer cell line SW480 was observed after treatment with 100 μM FN1-5 for 3 days (Table 2). This result was consistent with the staining result.

Using the small molecule compounds of the invention, FN1-5 and FN1-8, in the cell-based cytotoxicity assay, a dramatic cell killing was observed in the human colon cancer cell lines LoVo and CaCO2 (data not shown). FN1-8 seemed to more potent than FN1-5 in cell killing. Both, small molecule compounds FN1-5 and FN1-8 induced apoptosis in CaCO2 (Tables 2 and 3).

Two colon cancer cell lines, SW480 and HCT116, were also incubated with 10, 30, 50, and 100 µM of compounds FN1-9U and FN1-9S. No dramatic cell killing effect or apoptosis was observed (data not shown).

Example 7

Small Molecules FN1-5 But Not FN1-8 Induces Cell Killing and Apoptosis in Colon Cancer Cell Line HT29

Using the small molecule compound FN1-5 in the cell-based cytotoxicity assay, a dramatic cell killing was observed in the human colon cancer cell line HT29 (data not shown). However, no cell killing was observed after treatment with small molecule compound FN1-8 even at higher doses (50 µM; data not shown).

Flow cytometry was used to examine apoptosis in colon cancer cell line HT29 after treatment of cells with small molecule compounds FN1-5 and FN1-8. While FN1-5 induced apoptosis in HT29 cells (at 50 µM 35% apoptotic cells were observed; Table 2), no apoptosis was observed after treatment with FN1-8 (Table 3). These results were consistent with the staining result above. Thus, the fact that small molecule compound FN1-8 does not affect survival and does not induce apoptosis in HT29 cells also confirms that the effects mediated by FN1-8 in other cell lines tested are not due to a general toxicity of FN1-8.

In this respect it is noteworthy, that while HT29 cells express Gli1 and Gli2 (data not shown; Zhu et al., 2004, *Cancer Lett.* 207 (20:205-214), no expression of Gli3 was observed in HT29 cells (FIG. 2, lower panel, lane 3).

Example 8

Small Molecule Compounds FN1-5 and FN1-8 Induce Apoptosis in NSCLC Cells

Flow cytometry was also used to examine apoptosis in several NSCLC cell lines after treatment with small molecule compounds of the invention. For example, after treatment with 100 µM FN1-5 for 3 days, significant apoptosis was observed in the NSCLC cell lines H1299 (55.9% apoptosis), A549 (30.0% apoptosis) (see Table 2 for additional data). These results were consistent with the staining result.

After treatment with 30 µM and 50 µM FN1-8 for 3 days, significant apoptosis was also observed in the NSCLC cell lines H460 (75.2% apoptosis at 50 µM; Table 3) and H838 (82.3% at 50 µM; Table 3). These results were consistent with the staining results. FN1-5 also induced apoptosis in H460 and H838 cells (Table 2). Consistently, it was observed that FN1-8 was more potent than FN1-5 in inducing apoptosis at the same doses (Tables 2 and 3).

Using the small molecule compounds of the invention, FN1-5 and FN1-8, in the cell-based cytotoxicity assay, a dramatic cell killing was observed in the NSCLC cell lines H460, H838, H1975, H1650, and H1703. Comparing same concentrations, FN1-8 seemed more potent than FN1-5 in these cell lines (data not shown).

Dose titration experiments of small molecule compound FN1-8 was performed using the NSCLC cell lines A549, H358, and H322. A 549, H358, and H322 cells were plated in 6-well plates and incubated with DM SO (control) or 7.5 µM, 10 µM, 15 µM, 20 µM, and 30 µM of FN1-8, respectively, for 3 days. A dramatic and dose-dependent cell killing in these cell lines was observed when FN1-8 was added at 15 µM or more. FN1-8 induced cell killing in A549 and H368 at slightly lower concentrations than in H322 cells (data not shown). After 3 days, approximately 28% of the A549 cells and 58% of H358 underwent apoptosis when incubated with 20 µM FN1-8 (Table 3).

The time course of cell survival in NSCLC cells A549, H358, and H322 after administration of small molecule compound FN1-8 was analyzed. A549 cells were incubated with 10 µM and 20 µM FN1-8, and H358 and H322 cells were incubated with 15 µM and 30 µM FN1-8, respectively. Then flow cytometry was used to examine the percentage of living and dead cells at different time points. On A549 cells, FN1-8 shows a dose-dependent cell killing effect after 3 days. In H358 cells, the cell killing effect of FN1-8 is already apparent by 1 day, and in H322 cells by 2 days. (data not shown).

Small molecule compound FN1-8 also significantly inhibited cell proliferation in NSCLC cells, including A549, H358, and H322 cells. This was shown by incubating the cells with either 7.5 µM or 15 µM of FN1-8 and then performing a MTS assay according to the manufacturer's protocol at different time points after addition of the compound. It was found that FN1-8 inhibited cell proliferation in these cells in a dose-dependent manner already after 1 day. (data not shown).

Based on the screening results obtained with small molecule compound FN1-5 and FN1-8 additional small molecule compounds were tested on H1299 and A549 cells using the cytotoxicity and apoptosis assays described herein. Using 10, 30, 50, and 100 µM of compounds FN1-9U and FN1-9S no noticeable cell killing effect or apoptosis was observed (data not shown).

Example 9

Small Molecule Compounds FN1-5 and FN1-8 Induce Cell Killing and Apoptosis in Primary Cultured NSCLC Flow cytometry was also used to examine apoptosis induced by molecule compounds of the invention. in primary cultured NSCLC cells freshly made from tissue samples. For example, after treatment with 10, 30, and 50 µM FN1-8 or 30 and 50 µM FN1-5 for 3 days, significant apoptosis was observed in primary cultured NSCLC cells (data not shown). For example, app. 60% apoptotic cells were observed at 50 µM FN1-8. These result were consistent with results obtained in the cell-based cytotoxicity assay using primary cultured NSCLC cells (data not shown) and compounds FN1-5 and FN1-8. Again, FN1-8 was found to be more potent than FN1-5 at the same concentration.

Example 10

Small Molecule Compounds FN1-5 and FN1-8 Induce Apoptosis in Melanoma Cells

Figure 7:
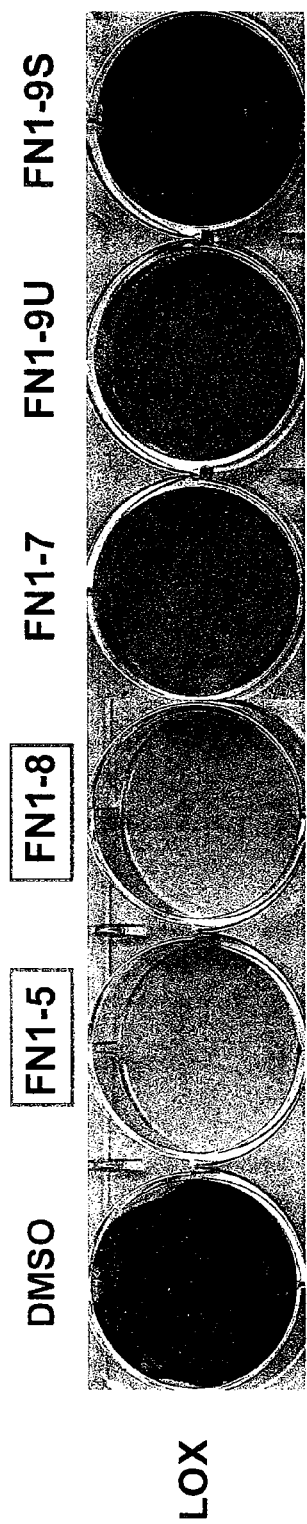
FIG. 7 shows the result of a cytotoxicity assay after treating LOX cells (melanoma) with small molecule compounds FN1-5, FN1-8, FN1-7, FN1-9U, and FN1-9S. Consistently, dramatic cell killing effect was observed for both FN1-5 and FN1-8. Some killing was also observed when LOX cells were incubated with small molecule compounds FN1-7 and FN1-9U. Live cells were stained by 0.5% crystal violet. DMSO was used as a control. Details are described, e.g., in Example 10.

The effect of small molecule compounds FN1-5, FN1-8, FN1-7, FN1-9U, and FN1-9S was tested using a cytotoxicity assay and the melanoma cell line LOX. LOX cells were plated in 6-well plates and incubated with 100 µM of each compound (stocks were dissolved in DMSO at 30 mM) for 3 days, as described herein. Consistently, dramatic cell killing effect was observed for both FN1-5 and FN1-8 (FIG. 7) Some killing was also observed when LOX cells were incubated with small molecule compounds FN1-7 and FN1-9U. Live cells were stained by 0.5% crystal violet.

Cell killing was also tested using human melanoma cell line LOX and different doses of the small molecule compounds FN1-5 and FN1-8. LOX cells were plated in 6-well plates and incubated with 10, 30, and 50 µM of each compound for 3 days, as described herein. Dramatic cell killing effect was observed for both compounds at 50 µM. It appeared that FN1-8 was more potent than FN1-5 in killing LOX cells as more cell killing is observed at 30 µM FN1-8 when compared to 30 µM FN1-5 (data not shown).

The cell killing of LOX cells by treatment with small molecule compounds FN1-5 and FN1-8 was analyzed in greater detail using various concentrations of these two compounds and flow cytometry. After 3 days of treatment, both compounds induced significant apoptosis in the LOX cell line at all concentrations tested: small molecule compound FN1-5 at 10 µM, 14.0% apoptosis, at 30 µM, 16.6% apoptosis, and at 50 µM, 58.1% apoptosis; control DMSO, 10.9% (Table 2); (b) small molecule compound FN1-8 at 10 µM, 16.7% apoptosis, at 30 µM, 19.0% apoptosis, and at 50 µM, 78.9% apoptosis (control DMSO: 10.9% apoptosis) (Table 3). Again, small molecule compound FN1-8 seemed to be more slightly potent than FN1-5 in apoptosis induction at comparable doses. (Tables 2 and 3).

Dose titration experiments of small molecule compound FN1-8 was performed using the melanoma cell lines A375, G361, SK-Mel-2, SK-Mel-5, and SK-Mel-28. A 375 cells were plated in 6-well plates and incubated with DM SO (control) or 2 µM, 5 µM, 10 µM, 20 µM, and 40 µM of FN1-8, respectively, for 3 days. A dramatic and dose-dependent cell killing in this cell line was observed when FN1-8 was added at 10 µM or more (data not shown). A similar cell killing effect was observed for the melanoma cell lines G361, SK-Mel-2, SK-Mel-5, and SK-Mel-28 (data not shown). After 4 days of incubation with 20 µM FN1-8, approximately 20% of the Malme-3M cells, 28% of SK-Mel-2 cells, 36% of SK-Mel-5 cells, 41% of A375 cells, and 17% of G361 cells underwent apoptosis, while less than 3% of normal skin fibroblast cells underwent apoptosis under the same conditions (Table 3).

Small molecule compound FN1-8 also significantly inhibited cell proliferation in melanoma cells, including Malme-3M, A375, G361, SK-Mel-2, SK-Mel-5, and SK-Mel-28 cell lines. This was shown by incubating the cells with either 5 µM or 10 µM of FN1-8 and then performing a MTS assay according to the manufacturer's protocol at different time points after addition of the compound. In Malme-3M, G361, SK-Mel-2, and SK-Mewl-28 FN1-8 inhibited cell proliferation in these cells at 10 µM after 1-2 days and in A375 and SK-Mel-5 cells already after 1 day. (data not shown).

The time course of cell survival in melanoma cell lines (Malme-3M, A375, G361, SK-Mel-2, SK-Mel-5, and SK-Mel-28) after administration of small molecule compound FN1-8 was analyzed. These melanoma cells were incubated with 10 µM or 20 µM FN1-8. Then flow cytometry was used to examine the percentage of living and dead cells at different time points. In all tested melanoma cells, FN1-8 at 20 µM showed a cell killing effect which was apparent after 2 days. (FIGS. 18A, B, and C, and data not shown).

Figure 18:
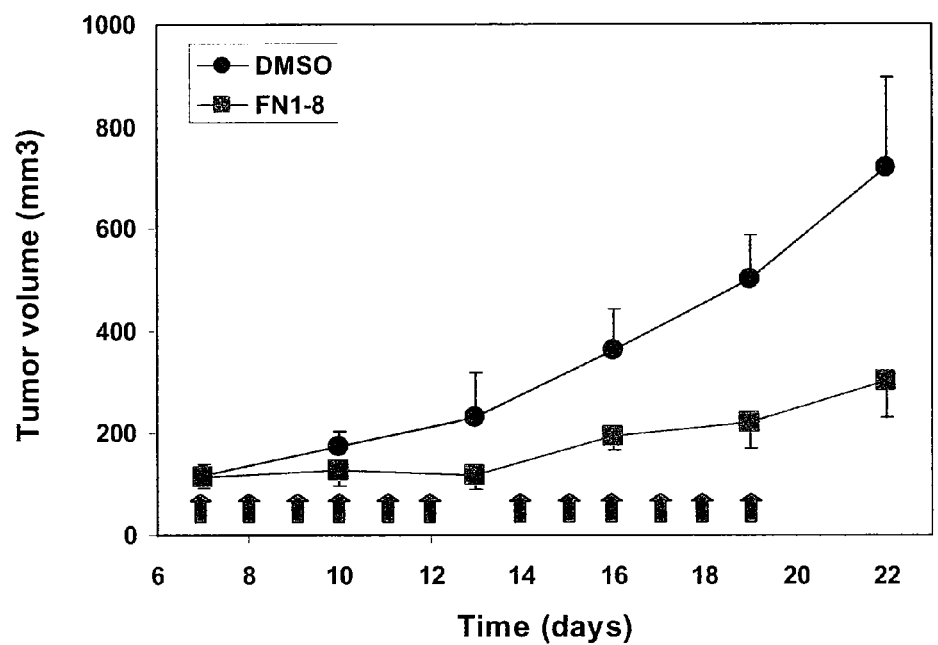
FIG. 18 shows an in vivo efficacy study of small molecule compound FN1-8 using a Mouse Xenograft Model (NSCLC H460). A. Tumor growth was significantly suppressed after treatment with the small molecule compound FN1-8. Arrows indicate daily injection of small molecule compound FN1-8 or DMSO as a control (each two times for 6 consecutive days). B. Tumors dissected from the mice of each group are shown. DMSO, DMSO treatment; FN1-8, treatment with small molecule compound FN1-8 as described herein. C. Tumor weight dramatically decreased after treatment with FN1-8. Results are the means±SD (error bars). Details are described, e.g., in Example 36.
Figure 18:
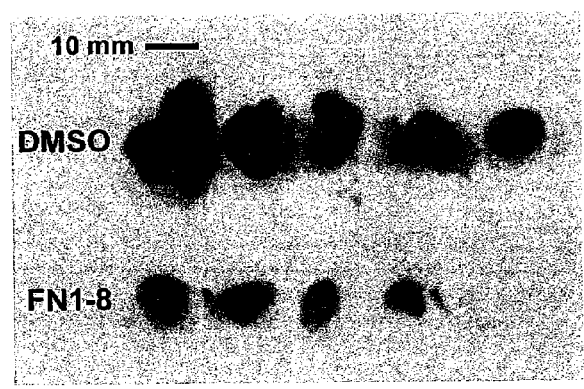
Figure 18:
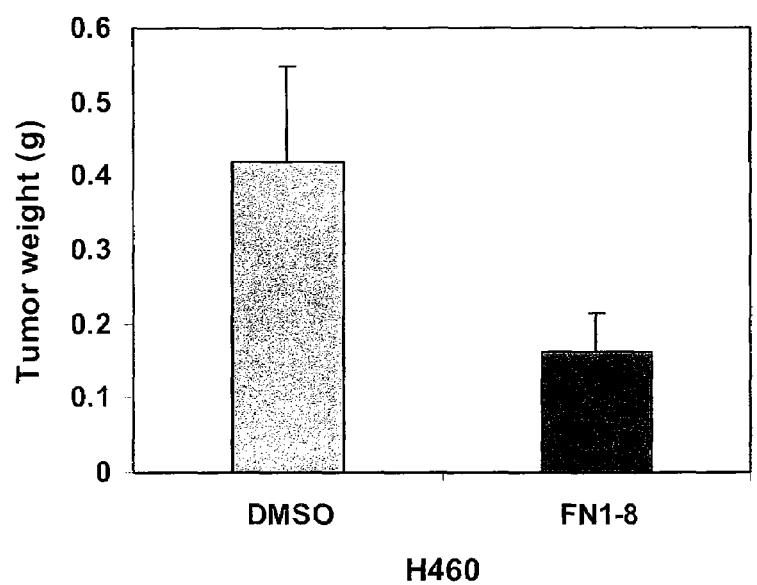

To investigate whether small molecule compounds of the present invention, e.g., FN1-8, specifically kill cancer cells, time course experiments of cell survival after administration of 10 µM and 20 µM of FN1-8 were also conducted using human normal skin fibroblast cells (Malme-3). When these cells were incubated with either 10 µM or 20 µM FN1-8 no cell killing was observed after 6 days (FIG. 18 D). Thus, administration of FN1-8 to normal skin fibroblasts did not affect the viability of these normal skin cells. This finding indicates that the cell killing effect of FN1-8 is specific for cancer cells.

Example 11

Small Molecules FN1-5 and FN1-8 Induce Apoptosis in Mesothelioma Cell Lines 211H and H290 and in Primary Cultured Mesothelioma Cells Cell killing was also tested using mesothelioma cell lines H290, 211H, MS1 and REN and different doses of the small molecule compounds FN1-5 and FN1-8. Cells were plated in 6-well plates and incubated with 1, 10, and 30 µM of each compound for 3 days, as described herein. Dramatic cell killing of H290 and 211H cells was observed for both compounds at 30 µM. (data not shown). Both compounds, however had no noticeable effect on MS-1 and REN cells at the concentrations tested (data not shown).

Flow cytometry was used to examine apoptosis in the mesothelioma cell line 211H after treatment of cells with small molecule compounds FN1-5 and FN1-8. Significant apoptosis in the mesothelioma cell line 211H was observed after treatment for 3 days with either 30 µM FN1-5 (37.5%; Table 2) or 30 µM FN1-8 (30.7%; Table 3).

Figure 8:
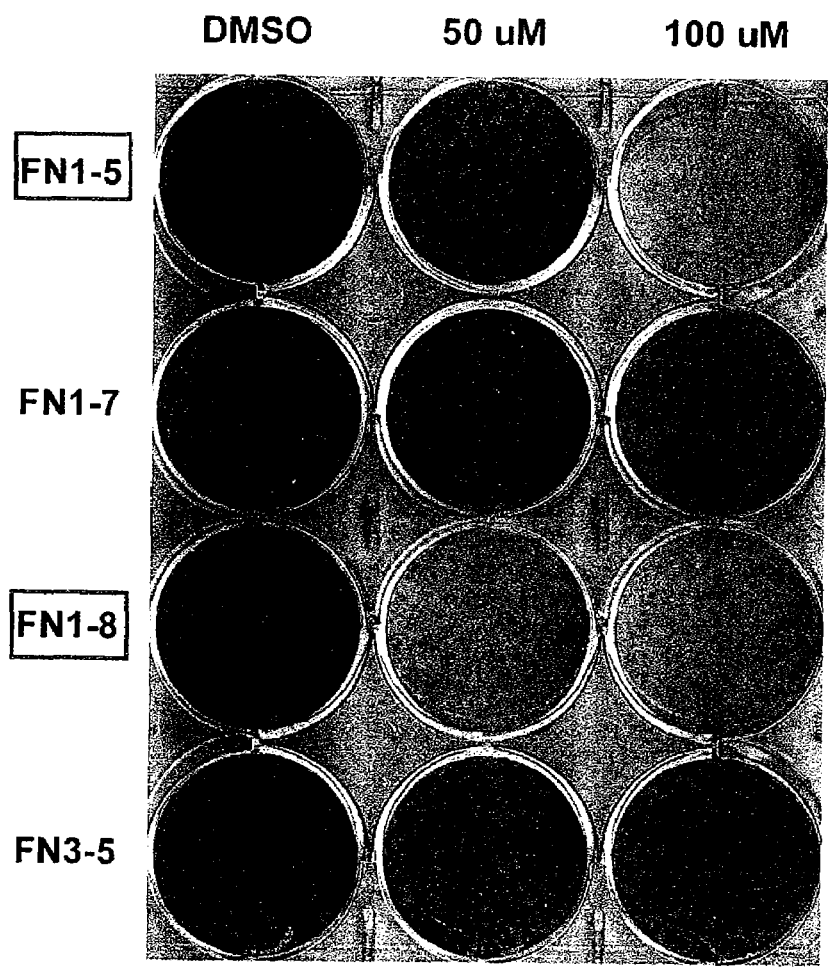
FIG. 8 shows the effect of different small molecule compounds on primary cultured human mesothelioma cells freshly made from tissue samples. Dramatic cell killing effect was observed for both FN1-5 and FN1-8. Small molecule compound FN1-8 was more potent than FN1-5 in killing this primary culture at the same dose. DMSO was used as a control. Details are described, e.g., in Example 11.

Next, the effect of different small molecule compounds on primary cultured human mesothelioma cells freshly made from tissue samples was examined. The primary cultures were plated in 6-well plates as described herein and incubated with 50 and 100 µM of each compound (FN1-5, FN1-7, FN1-8, and FN3-5; stocks were dissolved in DMSO at 30 mM) for 3 days. Dramatic cell killing effect was observed for both FN1-5 and FN1-8. Again, small molecule compound FN1-8 was more potent than FN1-5 in killing this primary culture at the same dose. No significant cell killing was found for compounds FN1-7 and FN3-5. (FIG. 8).

Next, flow cytometry was used to examine apoptosis after the treatment of small molecule compound FN1-5 at different doses (10 µM, 30 µM and 50 µM) for 3 days in primary cultured human mesothelioma cells freshly made from tissue samples. Increased apoptosis was observed at the intermediate doses (30 and 50 µM) for FN1-5 and FN1-8 (Tables 2 and 3, respectively). Consistent with the staining results shown in FIG. 8, FN1-8 was more potent than FN1-5 in apoptosis induction at the same dose (Tables 2 and 3).

The mesothelioma cell line MS-1 was also incubated with 10, 30, 50, and 100 µM of compounds FN1-9U and FN1-9S. While some cell killing was observed using 100 µM FN1-9U, no cell killing effect or apoptosis was observed using FN1-9S (data not shown).

Example 12

Effects of Small Molecule Compounds FN1-5 and FN1-8 on the Human Prostate Cancer Cell Line LnCAP The cell-based cytotoxicity assay described herein was used to determine the effect of small molecule compounds FN1-5 and FN1-8 on the human prostate cancer cell line LnCAP. Viability of LnCAP cells was analyzed after treatment with 30 and 50 µM FN1-5 and after treatment with 10, 30, and 50 µM FN1-8. A dramatic cell killing was observed at 50 µM FN1-8 (data not shown). A much lesser cell killing effect of FN1-5 was observed (data not shown).

Flow cytometry was also used to examine apoptosis induced by molecule compounds FN1-5 and FN1-8 in LnCAP cells. After treatment with 10, 30, and 50 µM FN1-8 or 30 and 50 µM FN1-5 for 3 days, significant apoptosis was observed in LnCAP cells (Tables 2 and 3). For example, app. 42% apoptotic cells were observed at 50 µM FN1-8. These result were consistent with results obtained in the cell-based cytotoxicity assay as described above Again, FN1-8 was found to be more potent than FN1-5 at the same concentration.

Example 13

Effects of Small Molecule Compounds FN1-5 and FN1-8 on Human Pancreatic Cancer Cell Lines The cell-based cytotoxicity assay described herein was used to determine the effect of small molecule compounds FN1-5 and FN1-8 on the human pancreatic cancer cell lines L3.6sl, Panc4.21, BxPC3, and CFPAC-1. Viability of these cells was analyzed after treatment with 10, 30 and 50 µM FN1-5 or FN1-8. A dramatic cell killing was observed at 50 µM FN1-5 or FN1-8 in all human pancreatic cancer cell lines analyzed (data not shown). However, cell killing mediated by FN1-5 in Panc4.21 was less when compared to its effect on the three other pancreatic cancer cell lines.

Flow cytometry was also used to examine apoptosis induced by molecule compounds FN1-5 and FN1-8 in the human pancreatic cancer cell lines L3.6sl, Panc4.21, BxPC3, and CFPAC-1 cells. After treatment with 10, 30, and 50 µM FN1-8 or 30 and 50 µM FN1-5 for 3 days, significant apoptosis was observed in all human pancreatic cancer cell lines analyzed with the exception of Panc4.21, where FN1-5 did not seem to induce apoptosis (Tables 2 and 3). For example, app. 45% apoptotic cells were observed at 50 µM FN1-5 and 50 µM FN1-8. These result were consistent with results obtained in the cell-based cytotoxicity assay as described above While FN1-5 and FN1-8 induced apoptosis to a similar extent in L3.6sl, FN1-5 was slightly more potent in CFPAC-1 cells, at the same concentrations, and FN1-8 induced a stronger apoptotic response than FN1-5 in Panc4.21 and BxPC3 cells (Tables 2 and 3).

Example 14

Effects of Small Molecule Compounds FN1-5 and FN1-8 on Human Breast Cancer Cell Line MCF-7

The cell-based cytotoxicity assay described herein was used to determine the effect of small molecule compounds FN1-5 and FN1-8 in the human breast cancer cell line MCF-7. Viability of MCF-7 cells was analyzed after treatment with 30 and 50 µM FN1-5 and after treatment with 10, 30, and 50 µM FN1-8. A dramatic cell killing was observed at 50 µM FN1-8 and 50 µM FN1-5 (data not shown). FN1-8 was more potent in this assay than FN1-5.

Example 15

Effects of Small Molecule Compounds FN1-5 and FN1-8 on Human Ovarian Cancer Cell Line AZ23247

The cell-based cytotoxicity assay described herein was used to determine the effect of small molecule compounds FN1-5 and FN1-8 in the human ovarian cancer cell line AZ23247. Viability of AZ23247 cells was analyzed after treatment with 10, 30 and 50 µM FN1-5 or FN1-8. A dramatic cell killing was observed with both compounds at 30 µM and 50 µM (data not shown).

Example 16

Effects of Small Molecule Compounds FN1-5 and FN1-8 on Human Renal Cell Carcinoma Cell Lines The cell-based cytotoxicity assay described herein was used to determine the effect of small molecule compounds FN1-5 and FN1-8 in the human renal cell carcinoma cell lines 786-O, Caki, and OMRC3. Viability of these cells was analyzed after treatment with 10, 30 and 50 µM FN1-5 or FN1-8. A dramatic cell killing in all human renal cell carcinoma cell lines analyzed was observed at 50 µM FN1-8 and 50 µM FN1-5 (data not shown). FN1-8 was more potent in this assay than FN1-5.

Example 17

Effects of Small Molecule Compounds FN1-5 and FN1-8 on Human Esophageal Cancer Cell Lines The cell-based cytotoxicity assay described herein was used to determine the effect of small molecule compounds FN1-5 and FN1-8 in the human esophageal cancer cell lines SEG-1, TE-7, BIC-1, and OE21. Viability of these cells was analyzed after treatment with 10, 30 and 50 µM FN1-5 or FN1-8. A dramatic cell killing in all human esophageal cells analyzed was observed at 50 µM FN1-8 and 50 µM FN1-5 (data not shown). FN1-8 was more potent in this assay than FN1-5.

Activation of Hh signaling in the human esophageal cancer cell lines SEG-1, TE-7, BIC-1, and OE21 was examined by semi-quantitative RT-PCR. Activation of Hh pathways, including expression of Ptch 1, Gli1 Gli2, and Gli3 was found in those cell lines (data not shown).

Example 18

Effects of Small Molecule Compounds FN1-5 and FN1-8 in Human Gastric Cancer Cell Lines The cell-based cytotoxicity assay described herein was used to determine the effect of small molecule compounds FN1-5 and FN1-8 in the human gastric cancer cell lines NUGC3, MNK28, and AGS. Viability of these cells was analyzed after treatment with 10, 30 and 50 µM FN1-5 or FN1-8. A dramatic cell killing in all human gastric cells analyzed was observed at 50 µM FN1-8 and 50 µM FN1-5 (data not shown). FN1-8 was more potent in this assay than FN1-5.

Example 19

Effects of Small Molecule Compounds FN1-5 and FN1-8 on Human Sarcoma Cell Lines

The cell-based cytotoxicity assay described herein was used to determine the effect of small molecule compounds FN1-5 and FN1-8 in the human sarcoma cell lines MG63 and MNNG. Viability of these cells was analyzed after treatment with 10, 30 and 50 µM FN1-5 or FN1-8. A dramatic cell killing in all sarcoma cells analyzed was observed at 50 µM FN1-8 (data not shown). No significant cell killing by FN1-5 was observed in these sarcoma cell lines (data not shown).

Example 20

Effects of Small Molecule Compounds FN1-5 and FN1-8 in Human Hepatocellular Carcinoma Cell Lines The cell-based cytotoxicity assay described herein was used to determine the effect of small molecule compounds FN1-5 and FN1-8 in the human hepatocellular carcinoma cell lines HEPG2 and SK-Hep-1. Viability of these cells was analyzed after treatment with 10, 30 and 50 μM FN1-5 or FN1-8. A dramatic cell killing in all human gastric cells analyzed was observed at 50 μM FN1-8 and 50 μM FN1-5 (data not shown). FN1-8 seemed to be more potent in this assay than FN1-5.

Example 21

Effects of Small Molecule Compounds FN1-5 and FN1-8 in Human Nasopharyngeal Cancer Cell Lines The cell-based cytotoxicity assay described herein was used to determine the effect of small molecule compounds FN1-5 and FN1-8 in the human nasopharyngeal cancer cell lines HNE1 and HONE1. Viability of these cells was analyzed after treatment with 10, 30 and 50 μM FN1-5 or FN1-8. A dramatic cell killing in all human gastric cells analyzed was observed at 50 μM FN1-8 and 50 μM FN1-5 (data not shown). FN1-8 was more potent in this assay than FN1-5.

Example 22

Effects of Small Molecule Compounds FN1-5 and FN1-8 in Human Glioma Cell Line U87

The cell-based cytotoxicity assay described herein was used to determine the effect of small molecule compounds FN1-5 and FN1-8 in the human glioma cell line U87. Viability of U87 cells was analyzed after treatment with 30 and 50 μM FN1-5 and 10, 30, and 50 μM FN1-8. A dramatic cell killing was observed at 50 μM FN1-8 and to a lesser extent with 50 μM FN1-5 (data not shown).

Example 23

Effects of Small Molecule Compounds on Normal Human Muscle Cells

The cell killing effect of small molecule compounds FN1-8, FN1-7, and FN1-5 at different doses was examined in normal human muscle cells. FN1-7 which has similar structure as the other two compounds, but does not have much cytotoxicity in cancer cell lines tested was included as a negative control. Normal muscle cells were plated in 6-well plates and incubated with 1, 10, 30, and 50 μM of each compound for 3 days, in the same manner as described herein for similar other experiments. No noticeable cell killing effect was observed for all compounds at all doses, suggesting that both FN1-5 and FN1-8 are not toxic to normal muscle cells. Both FN1-5 and FN1-8 seem to be specific in killing cancer cells.

In addition, apoptosis induction after the treatment of different doses of FN1-5 or FN1-8 in normal human muscle cells was examined by flow cytometry. Normal muscle cells were plated in 6-well plates and incubated with 1, 10, 30, and 50 μM of each compound for 3 days, as above. No noticeable difference in the number of apoptotic cells was observed for both compounds at all doses when compared to the DMSO controls, further suggesting that both FN1-5 and FN1-8 are not toxic to normal muscle cells (Tables 2 and 3). This result also indicates that both FN1-5 and FN1-8 are specifically in inducing apoptosis in cancer cells.

Example 24

Effects of Small Molecule Compounds FN1-5 and FN1-8 on Normal Human Renal Cells The cell killing effect of small molecule compounds FN1-5, and FN1-8 at different doses was examined in normal human renal cells. Normal renal cells were plated in 6-well plates and incubated with 30 and 50 μM of compound FN1-5 and 10, 30, and 50 μM FN1-8 for 3 days, in the same manner as described herein for similar other experiments. No noticeable cell killing effect was observed for all compounds at all doses, suggesting that both FN1-5 and FN1-8 are not toxic to normal renal cells (data not shown).

In addition, apoptosis induction after the treatment of different doses of FN1-5 (30 and 50 μM) or FN1-8 (10, 30, and 50 μM) in normal human renal cells was examined by flow cytometry. No noticeable difference in the number of apoptotic cells was observed for both compounds at all doses when compared to the DMSO controls, further suggesting that both FN1-5 and FN1-8 are not toxic to normal renal cells (Tables 2 and 3).

Example 25

Summary of Apoptosis Inducing Effect of Small Molecule FN1-5

The following table summarizes the % of apoptotic cells observed after treatment with small molecule compound FN1-5 at the indicated concentrations. Assays were performed as described herein. N.d., not done.

TABLE 2

Inducing Apoptosis in Cells Using Small Molecule Compound FN1-5

| Cell Line | DMSO (control) | 10 μM | 30 μM | 50 μM | 100 μM |
|---|---|---|---|---|---|
| CaCO2 (colon cancer) | 7.2 | 8.2 | 19.8 | 30.3 | n.d. |
| HT29 (colon cancer) | 5.2 | 5.8 | 15.5 | 32.9 | n.d |
| SW480 (colon cancer) | 6.2 | 10.8 | n.d. | n.d | 58.6 |
| A549 (NSCLC) | 10.2 | 9.4 | n.d. | n.d. | 30.0 |
| H460 (NSCLC) | 7.3 | n.d. | 11.9 | 15.7 | n.d. |
| H838 (NSCLC) | 6.7 | n.d. | 14.2 | 20.0 | n.d. |
| H1299 (NSCLC) | 5.9 | 6.7 | n.d. | n.d | 55.9 |
| Primary Cultured NSCLC Cells | 10.0 | n.d | 11.2 | 19.8 | n.d |
| LOX (melanoma) | 10.9 | 14.0 | 16.6 | 58.1 | n.d. |
| 211H (mesothelioma) | n.d. | 7.7 | 37.5 | n.d | n.d. |
| Primary cultured mesothelioma | n.d. | 12.3 | 15.8 | 18.3 | n.d. |
| BxPC3 (pancreatic cancer) | 10.1 | n.d. | 11.2 | 30.0 | n.d |
| CFPAC-1 (pancreatic cancer) | 12.8 | n.d. | 17.4 | 30.6 | n.d |
| L3.6s1 (pancreatic cancer) | 11.8 | n.d. | 27.5 | 44.8 | n.d |
| Panc4.21 (pancreatic cancer) | 9.6 | n.d. | 9.3 | 10.3 | n.d |
| LnCAP (prostate cancer) | 8.2 | n.d. | 7.7 | 16.3 | n.d. |

TABLE 2-continued

Inducing Apoptosis in Cells Using Small Molecule Compound FN1-5

| Cell Line | DMSO (control) | 10 μM | 30 μM | 50 μM | 100 μM |
|---|---|---|---|---|---|
| Normal muscle cells | 7.2 | 7.5 | 7.6 | 8.8 | n.d. |
| Normal renal cells | 4.2 | n.d | 5.6 | 6.6 | n.d. |

Example 26

Summary of Apoptosis Inducing Effect of Small Molecule FN1-8

The following table summarizes the % of apoptotic cells observed after treatment with small molecule compound FN1-8 at the indicated concentrations. Assays were performed as described herein. N.d., not done.

TABLE 3

Inducing Apoptosis in Cells Using Small Molecule Compound FN1-8

| Cell Line | DMSO (control) | 10 μM | 20 μM | 30 μM | 50 μM | 100 μM |
|---|---|---|---|---|---|---|
| CaCO2 (colon cancer) | 7.2 | n.d. | n.d | 19.9 | 39.4 | n.d. |
| HT29 (colon cancer) | 5.2 | n.d. | n.d | 3.1 | 5.3 | n.d |
| H460 (NSCLC) | 7.3 | n.d. | n.d. | 12.1 | 75.2 | n.d. |
| H838 (NSCLC) | 6.7 | 10.6 | n.d. | 18.3 | 82.3 | n.d. |
| A549 (NSCLC) | 12.2 | 12.5 | 27.4 | n.d | n.d. | n.d. |
| H358 (NSCLC) | 8.9 | 15.2 | 58.1 | n.d. | n.d. | n.d. |
| Primary cultured NSCLC cells | 10.0 | 9.8 | n.d. | 13.1 | 58.0 | n.d. |
| LOX (melanoma) | 10.9 | 16.7 | n.d. | 19.0 | 78.9 | n.d. |
| Malme-3M (melanoma) | 7.7 | 10.5 | 19.4 | n.d. | n.d. | n.d. |
| SK-Mel-2 (melanoma) | 7.2 | 9 | 25.3 | n.d. | n.d. | n.d. |
| SK-Mel-5 (melanoma) | 6.9 | 7.9 | 34.9 | n.d. | n.d. | n.d. |
| SK-Mel-28 (melanoma) | 7.3 | 7.7 | 11.8 | n.d. | n.d. | n.d. |
| A375 (melanoma) | 3.0 | 35.8 | 39.7 | n.d. | n.d. | n.d. |
| G361 (melanoma) | 7.1 | 7.5 | 15.5 | n.d. | n.d. | n.d. |
| Malme-3 (normal skin cells) | 1.2 | 2.1 | 3.2 | n.d. | n.d. | n.d. |
| 211H (mesothelioma) | n.d. | 5.6 | n.d. | 30.7 | n.d. | n.d. |
| Primary cultured mesothelioma | n.d. | 13.2 | n.d. | 14.7 | 33.6 | n.d. |
| BxPC3 (pancreatic cancer) | 10.1 | 11.4 | n.d. | 20.4 | 77.4 | n.d |
| CFPAC-1 (pancreatic cancer) | 12.8 | 15.4 | n.d. | 15.0 | 19.8 | n.d |
| L3.6s1 (pancreatic cancer) | 11.8 | 12.8 | n.d. | 25.1 | 45.7 | n.d |
| Panc4.21 (pancreatic cancer) | 9.6 | 11.2 | n.d. | 10.6 | 23.4 | n.d |
| LnCAP (prostate cancer) | 8.2 | 6.9 | n.d. | 11.0 | 41.5 | n.d. |
| Normal muscle cells | 8.0 | 7.8 | n.d. | 9.3 | 9.7 | n.d. |
| Normal renal cells | 4.3 | 3.1 | n.d. | 4.1 | 6.2 | n.d. |

Example 27

Regulation of Wnt2 Promoter Activity by Small Molecules in the NSCLC Cell Line A549

Figure 9:
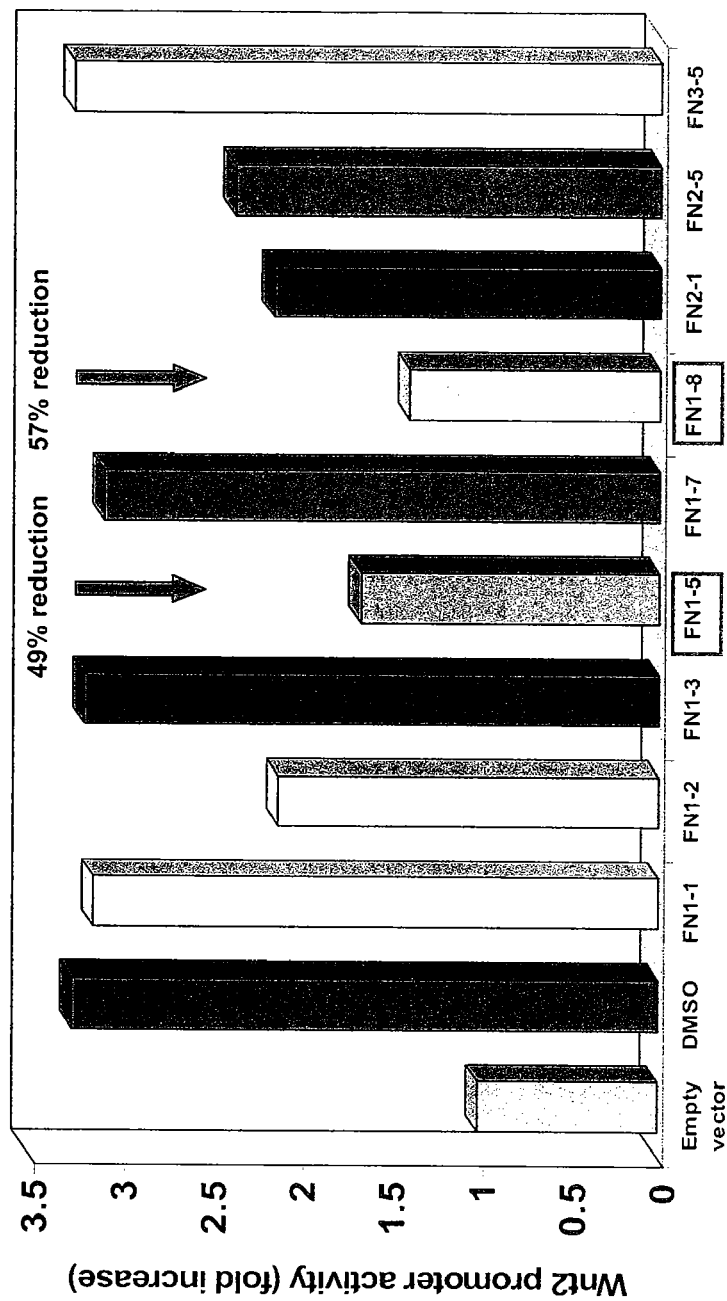
FIG. 9 shows regulation in the NSCLC cell line A549 of Wnt2 promoter activity by small molecule compounds FN1-1, FN1-2, FN1-3, FN1-5, FN1-7, FN1-8, FN2-1, FN2-5, and FN3-5. Both FN1-5 and FN1-8 down-regulate Wnt2 promoter activity dramatically. DMSO and "Empty vector" are controls. Details are described, e.g., in Example 27.

To examine the specificity of the small molecule compounds of the invention, the compounds were tested for regulate the expression of Gli down-stream target genes. Wnt signaling has been shown to be activated down-stream of Gli activation, and Hh/Gli signaling has been shown to regulate the expression of Wnt genes. The human Wnt2 promoter was cloned and found to contain putative Gli-DNA binding sites within its promoter region (data not shown). Thus, the Wnt2 promoter-luciferase reporter activity was assayed after treating the NSCLC cell line A549 (expressing Wnt2) with several small molecule compounds of the invention. After treatment for 18-24 hours at 30 μM, both FN1-5 and FN1-8 were found to down-regulate Wnt2 promoter activity dramatically (FIG. 9). Small molecule compounds that did not have such a potent cell killing effect as FN1-5 and FN1-8, did have either a much lesser effect or no effect on downregulation of Wnt2 Promoter activity (FIG. 9). This result is consistent with the cytotoxicity and apoptosis analysis and strongly indicates that both FN1-5 and FN1-8 induce apoptosis through inhibition of Gli transcription of Wnt2 expression.

Example 28

Small Molecule Compounds FN1-5 and FN1-8 Modulate the Hedgehog Pathway in Cancer Cells To further examine the mechanism of action of the small molecule compounds of the present invention, the effect of compounds FN1-5 and FN1-8 on the Hedgehog (Hh) signaling pathway was examined in NSCLC cell lines H460 and A549. H460 and A549 cells were incubated with 30 μM of each compound (FN1-5 or FN1-8) for 2 days before isolation of total RNA that was used for semi-quantitative RT-PCR analysis. Key components and direct target genes of the Hh pathway (e.g., Ptch1 and Gli1) were found to be downregulated (data not shown). GAPDH served as a control.

Similarly as demonstrated above, using a Wnt2 promoter-luciferase reporter activity assay, it was found that Wnt2 expression was also down-regulated after FN1-8 treatment (data not shown). These findings suggest that small molecule compounds FN1-5 and FN1-8 may be dual inhibitors for both Hh and Wnt pathways. In addition, it appeared that FN1-8 has a more inhibitory effect on both pathways than FN1-5, consistent with the apoptosis analysis in these cell lines (data not shown).

As demonstrated by semi-quantitative RT-PCR, the small molecule compounds FN1-5 and FN1-8 could also modulate the hedgehog pathway in the melanoma cell line LOX, the colon cancer cell line SW480 and in primary cultured human mesothelioma cells freshly made from tissue (data not shown). Interestingly, no noticeable changes were observed in HT29 cells (data not shown).

Example 29

Small Molecule Compound F1-8 Down-Regulates GLI1-Induced Transcription in Melanoma Cells To further examine the specificity of the small molecule compound FN1-8, in particular, the effect of FN1-8 to regulate the Hh/Gli signaling pathway was examined by testing for GLI-dependent transcription in the absence and presence of small molecule compound FN1-8. Specifically, a plasmid expression construct in which 6 repeats of a GLI-binding site (6xGLI BS; Sasaki et al, *Development* 124(7):1313-22 (1997)) linked to a luciferase reporter gene as a surrogate measurement of GLI-dependent transcription was used to measure the 6xGLI BS-luciferase activity after administration of FN1-8 in several melanoma cell lines, including Malme-3M (FIG. 15A), A375 (FIG. 15B), SK-Mel-2 (FIG. 15C), and SK-Mel-5 (FIG. 15D). In all 4 melanoma cell lines tested, co-expression of GLI1 (by transfection of a Gli1 expression plasmid described herein into the melanoma cells) significantly increased the 6xGLI BS-luciferase activity (FIGS. 15A-D, columns marked "Gli+DMSO"). This confirmed that over-expressed (i.e., exogenously added) GLI1 specifically bound to the GLI-binding sites and functionally induced transcription of the reporter gene, luciferase. A control vector not expressing GLI1 and also transfected into these melanoma cells, did not result in high levels of luciferase activity (FIGS. 15A-D, columns marked "Control vector+DMSO"). After treatment for 16-20 hours at 20 µM FN1-8, a significantly reduced level of luciferase activity was observed (FIGS. 15A-D, columns marked "Gli+20 uM FN1-8"). Thus, small molecule compound FN1-8 significantly reduced GLI1-induced transcription in these melanoma cells. This result indicated that FN1-8 was an inhibitor for GLI-dependent transcription. This finding also provides a method for inhibiting GLI-dependent transcription in a cell.

Example 30

Small Molecule Compounds FN1-5 and FN1-8 Down-Regulate GLI1- and GLI2-Induced Transcription in Pancreatic Cancer Cells To further examine the specificity of the small molecule compounds FN1-5 and FN1-8 to inhibit Hh/Gli signaling pathways, GLI-dependent transcription in the absence and presence of these compounds was also determined in pancreatic cancer cells. Specifically, the (6xGli BS) luciferase reporter gene construct described in Example 29 was used to measure the 6xGLI BS-luciferase over-expression of GLI1 alone (by transfection of a Gli1 expression plasmid described herein into the Panc4.21 cells) or GLI2 alone (by transfection of a Gli2 expression plasmid described herein into the Panc4.21 cells) significantly increased the 6xGLI BS-luciferase activity (data not shown). This confirmed that over-expressed (i.e., exogenously added) GLI1 or GLI2 polypeptides specifically bound to the GLI-binding sites and functionally induced transcription of the luciferase reporter gene. A control vector not expressing Gli1 or Gli2 or a Gli3 expression vector when transfected into these pancreatic cancer cells, did not result in high levels of luciferase activity (data not shown). The fact that Gli3 expression did not result in an increased luciferase activity is likely due to the presence of both activator and repressor domains in GLI3.

After treatment for 16-20 hours at 20 µM FN1-5 or FN1-8, a significantly reduced level of luciferase activity was observed (data not shown). Thus, small molecule compounds FN1-5 and FN1-8 significantly reduced GLI1- and GLI2-induced transcription in pancreatic cancer cells. These results indicated that FN1-5 and FN1-8 acted as inhibitors for GLI1- and GLI2-dependent transcription. This finding also provides a method for inhibiting GLI1- and GLI2-dependent transcription in a cell.

In a separate experiment, it was found that co-transfection of a $TAF_{II}31$ expression plasmid with either the GLI1 or G1LI2 expression plasmids also significantly increased the 6xGLI BS-luciferase activity (data not shown). Upon addition of either FN1-5 or FN1-8 (20 µM for 16-20 hours), 6xGLI BS-luciferase activity was significantly reduced (data not shown). The $TAF_{II}31$ expression plasmid contained the full-length $TAF_{II}31$ cDNA generated by PCR cloned into the EcoRI (5') and BamHI (3') sites of a mammalian expression vector containing a c-Myc tag (pCDNA3.1 (−)B. The sequence of $TAF_{II}31$ corresponds to GenBank Accession No. U25112.

Example 31

Regulation of TOP/FOP Activity by Small Molecule Compounds in Colon Cancer Cell Lines HCT116 and SW480

Figure 10:
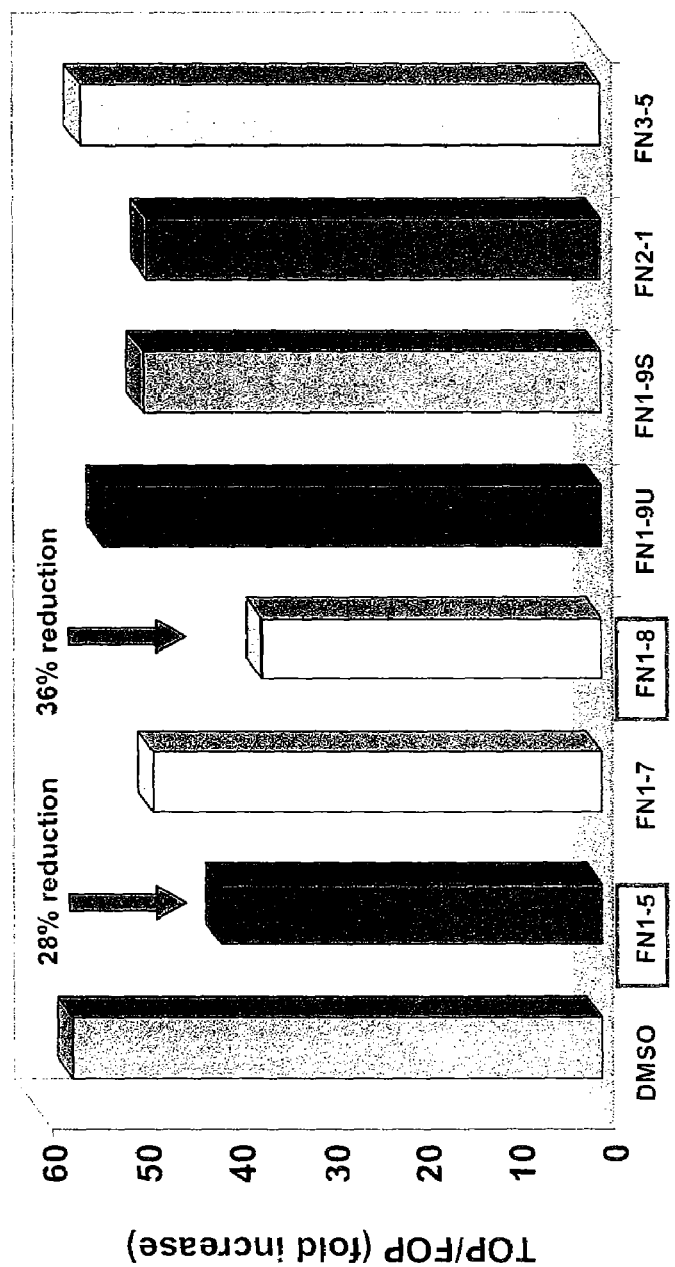
FIG. 10 shows regulation of the TOP/FOP activity in the colon cancer cell line HCT116 by small molecule compounds FN1-5, FN1-7, FN1-8, FN1-9U, FN1-9S, FN2-1, and FN3-5. Both FN1-5 and FN1-8 were found to down-regulate TOP/FOP activity dramatically. DMSO was used as a control. Details are described, e.g., in Example 31.

As another specificity test of the small molecule compounds of the invention, it was tested whether small molecule compounds FN1-5, FN1-7, FN1-8, FN1-9U, FN1-9S, FN2-1, and FN3-5 could regulate the transcription activity of the canonical Wnt signaling by using TOP/FOP assay. In these experiments, colon cancer cell lines were used which have been shown to have high TCF transcription activity measured by TOP/FOP assay. FIG. 10 shows the result in HCT116 cells. After treatment for 18-24 hours at 30 µM, both FN1-5 and FN1-8 were found to down-regulate TOP/FOP activity dramatically. No significant down-regulation was observed in this assay using compounds that also did not induce significant cell killing. This result is also consistent with the cytotoxicity, apoptosis and the Wnt2 promoter activity analysis, and indicates that both FN1-5 and FN1-8 induce apoptosis by inhibiting Gli transcription of Wnt2 expression, which in turn, inhibits Wnt signaling dependent transcription.

Regulation of TOP/FOP activity by the same compounds as described above was also analyzed in the colon cancer cell line SW480. While compound FN1-5 had a lesser effect in this cell line, small molecule compound FN1-8 reduced TOP/FOP activity also in SW480 cells by about 32% (data not shown), compared to about 36% reduction in HCT116 cells (see FIG. 10).

Example 32

Regulation of SOCS-3 and Gremlin Promoter Activity by Small Molecule Compounds

Figure 11:
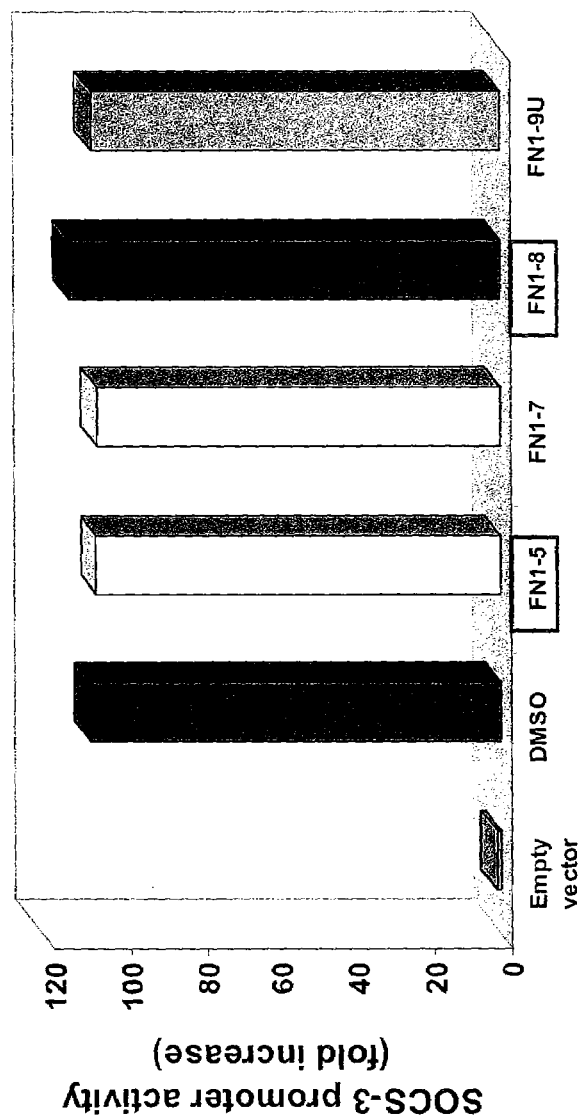
FIG. 11 shows that small molecule compounds FN1-5 and FN1-8 do not regulate SOCS3 promoter activity in NSCLC A549 cells. Empty vector and DMSO serve as controls. Details are described, e.g., in Example 32.

As a third specificity test for the small molecule compounds of the present invention, the ability of these compounds to regulate the expression of genes that are not downstream targets of the Gli activation was analyzed. SOCS3, an inhibitor and down-stream target gene of JAK/STAT pathway was chosen for this experiment. Expression of SOCS3 is not under control of Gli and/or Wnt activation. Furthermore, no GLI and TCF binding sites were found in the human SOCS3 promoter cloned in the laboratory of Dr. Jablons (University of California, San Francisco; data not shown). Thus, SOCS3 promoter-luciferase reporter activity was measured after the treatment of the NSCLC cell line A549 with small molecule compounds FN1-5, FN1-7, FN1-8, and FN1-9U. After treatment for 18-24 hours at 30 µM, both FN1-5 and FN1-8 were found inactive in regulating the SOCS3 promoter activity, similar as other compounds that have shown no cell killing effect (e.g., FN1-7 and FN1-9U; FIG. 11). This result indicates that both FN1-5 and FN1-8 are specific small molecule inhibitors for the inhibition of GLI transcription activity.

As a fourth specificity test for the small molecule compounds of the present invention, the ability of compounds FN1-5 and FN1-8 to regulate the expression of another gene that is not a down-stream targets of the Gli activation was tested. Gremlin, an inhibitor of BMP and TGF-β signaling was chosen for this experiment. Gremlin expression is not under control of Gli and/or Wnt activation. Thus, the activity of the human Gremlin promoter-luciferase reporter was examined after treatment of HEK 293T cells with compounds FN1-5, FN1-8 or with DMSO (control) or empty vector (control). After treatment for 18-24 hours at 30 µM, both FN1-5 and FN1-8 were found inactive in regulating the Gremlin promoter activity (data not shown). This result also indicates that both FN1-5 and FN1-8 are specific small molecule inhibitors for the inhibition of GLI transcription activity. The human Gremlin was cloned in the laboratory of Dr. Jablons (University of California, San Francisco, data not shown).

Example 33

Figure 12:
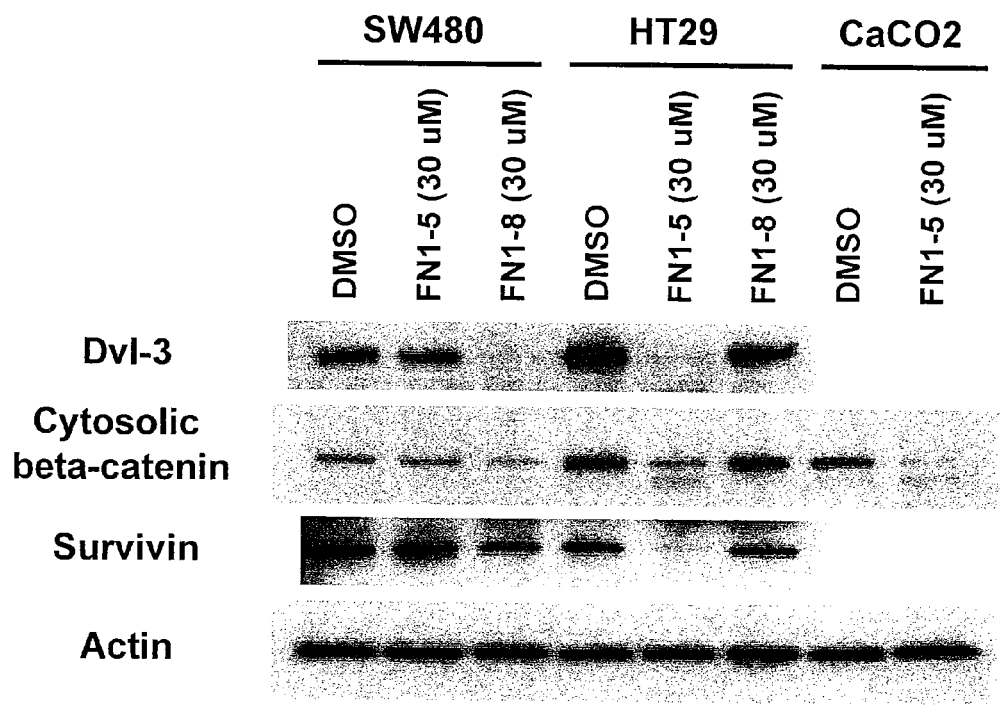
FIG. 12 shows a Western blot analysis of Dvl-3, cytosolic beta-catenin, Survivin and actin (control) in colon cancer cells after treatment with FN1-5 and FN1-8. The small molecule compounds FN1-5 and FN1-8 suppress canonical Wnt signaling in colon cancer cells. Details are described, e.g., in Example 33.

Small Molecule Compound Inhibitors for GLI Signaling Suppress Canonical Wnt Signaling in Colon Cancer Cells, in NSCLC Cells, and in Melanoma Cells To test whether small molecule compounds of the present invention work as small molecule inhibitors for GLI3 activation domain and suppress canonical Wnt signaling, Western blot analysis of canonical Wnt signaling key components (such as Dvl-3 and cytosolic β-catenin) was performed in colon cancer cells SW480, HT29, and CaCO2 after treatment with small molecule compounds FN-15 and FN1-8 and DMSO (control) at 30 µM for 2 days. β-actin served as loading control. Consistent with the results of apoptosis induction, a dramatic down-regulation of Dvl-3 and cytosolic beta-catenin in these cells was observed after treatment with the compounds (FIG. 12). Surviving, an apoptosis inhibitor and a Wnt down-stream target gene (Kim et al., 2003), was also down-regulated (FIG. 12). It is interesting to note that in HT29 cells, no down-regulation of Dvl-3 and cytosolic β-catenin was observed after FN1-8 treatment, consistent with the finding that the viability of HT29 cells was not affected by FN1-8 compound.

Figure 13:
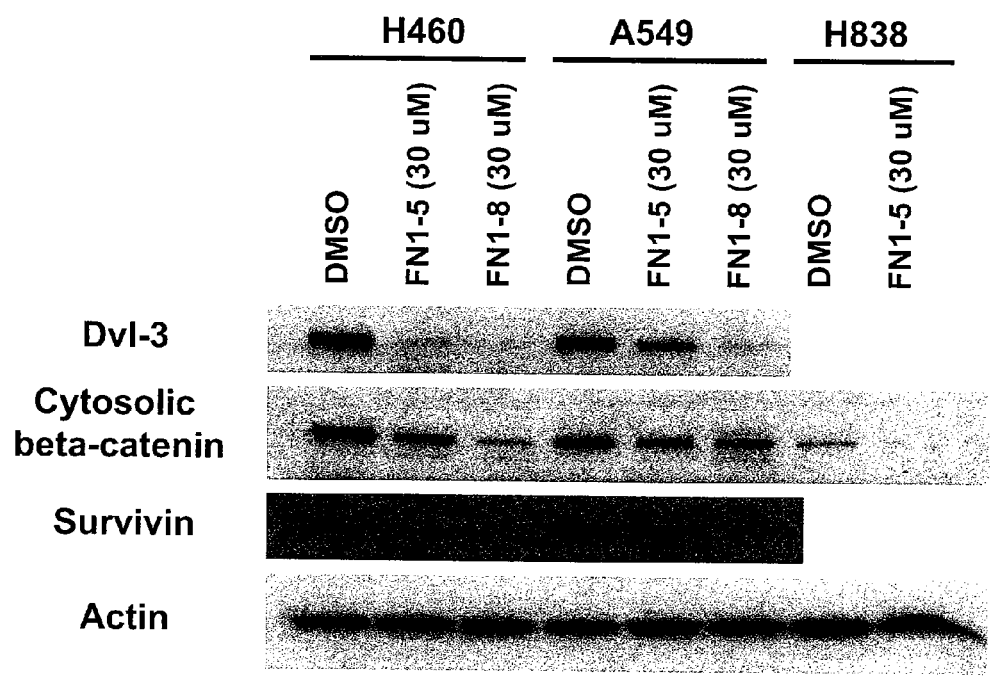
FIG. 13 shows a Western blot analysis of Dvl-3, cytosolic beta-catenin, Survivin and actin (control) in NSCLC cells after treatment with FN1-5 and FN1-8. The small molecule compounds FN1-5 and FN1-8 suppress canonical Wnt signaling in NSCLC cells. Details are described, e.g., in Example 33.
Figure 14:
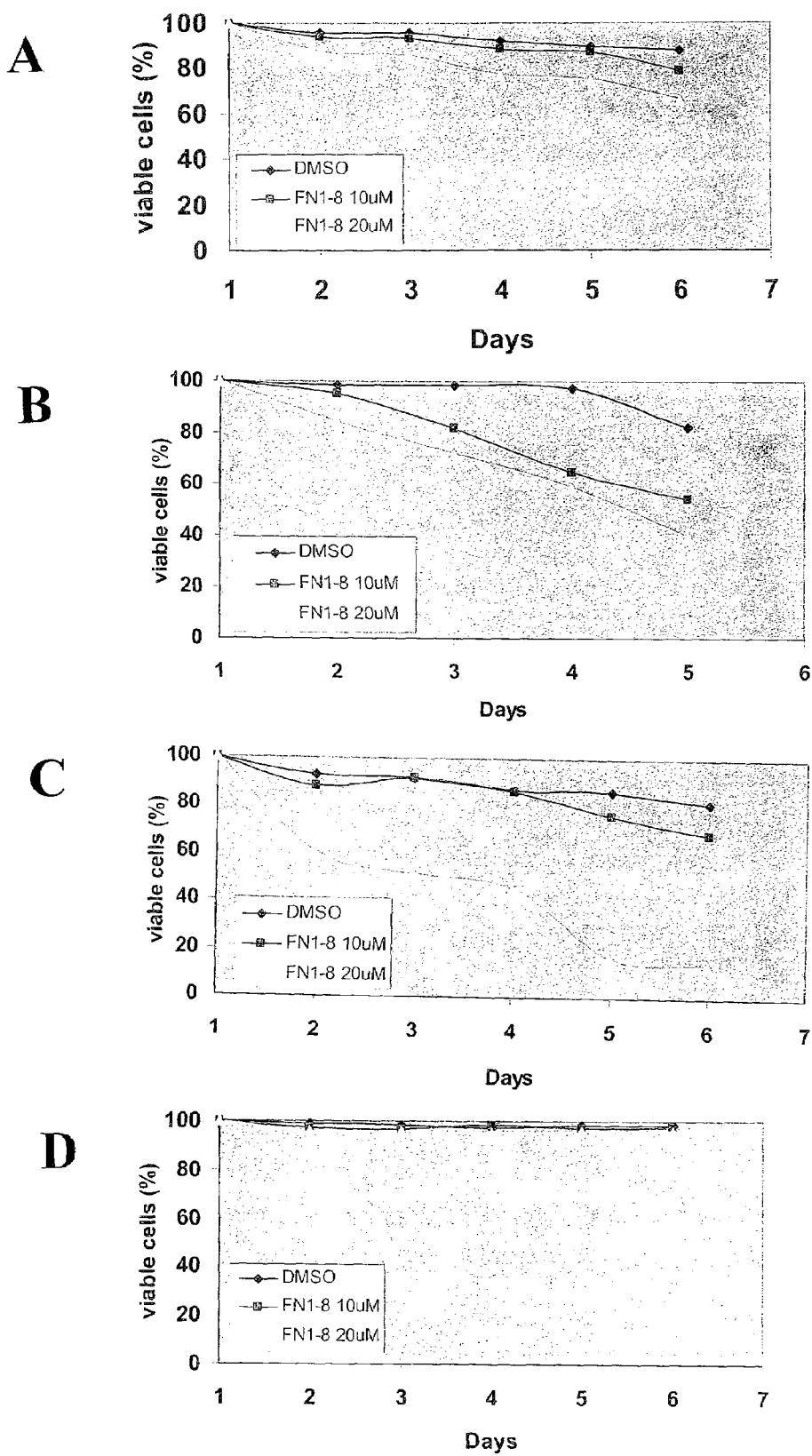
FIG. 14 shows the result of a time course experiment demonstrating that FN1-8 induces significant apoptosis in Malme-3M cells (A), A375 cells (B), and SK-Mel-5 cells (C), but not in human normal skin fibroblast cells (D). Details are described in Example 10.

To test whether small molecule compounds of the present invention work as small molecule inhibitors for GLI3 activation domain and suppress canonical Wnt signaling, Western blot analysis of canonical Wnt signaling key components (such as Dvl-3 and cytosolic β-catenin) was performed in the NSCLC cells H460, A549, and H838 after treatment with small molecule compounds FN-15 and FN1-8 and DMSO (control) at 30 µM for 2 days. β-actin served as loading control. Consistent with the results of apoptosis induction, a dramatic down-regulation of Dvl-3 and cytosolic beta-catenin in these cells was observed after treatment with the compounds (FIG. 13). Surviving, an apoptosis inhibitor and a Wnt down-stream target gene (Kim et al., 2003), was also down-regulated (FIG. 13).

In another experiment we used Western blot analysis to test whether the small molecule compound FN1-8 suppressed the melanoma cell growth (see above) through inhibition of the Wnt canonical pathway. Cytosolic proteins were isolated from two melanoma cell lines, A375 and SK-Mel-5 and from human normal skin fibroblasts (Malme-3), after treatment with DMSO (control), 10 µM, or 20 µM FN1-8. β-actin served as a control. These experiments showed that in both melanoma cells one of the key indicator of the canonical Wnt activation pathway, the cytosolic β-catenin level, was down-regulated after treatment with FN1-8 (data not shown). However, no noticeable change in the cytosolic β-catenin level was observed in the human normal skin fibroblast cells (data not shown). These results indicate that small molecule compounds of the present invention, as shown here by FN1-8, specifically suppress melanoma cell growth and induce apoptosis in these cancer cells through inhibition of the canonical Wnt pathway. As indicated herein already, these results further lend support that FN1-8 is a dual inhibitor for both Hh and Wnt signaling pathways.

Example 34

Over-Expression of GLI2 Rescues Colon Cancer Cell Line SW480 Treated with Small Molecule Compound Inhibitors FN1-5 and FN1-8

As described herein, GLI3 seems to activate transcription of Gli1 and Gli2 genes. Thus, inhibition of GLI3 activity by small molecule compounds of the invention should also inhibit signaling by GLI1 and/or GLI2. If so, then transfecting a GLI1 and/or GLI2 expression construct into a cell treated with a small molecule compound of the present invention, should lead to at least a partial rescue of the apoptotic effect mediated by the small molecule compound. Thus, to further examine the specificity of the small molecule compound FN1-5, as well as its inhibitory mechanisms, it was tested whether over-expressing GLI2 protein could attenuate the cell killing effect of FN1-5. In this experiment, the colon cancer cell line SW480 was transfected with either empty pCDNA3 vector or with a Gli2 cDNA expression construct. After selection, the transfected cells were re-plated in 6-well plates at same numbers, and then FN1-5 was added into medium at a final concentration of 50 µM. After 5 days, FN1-5 was found to kill less cells transfected with Gli2 than those with empty vector (data not shown). This result indicated that FN1-5 killed cancer cells by inhibiting the GLI3 transcription activator function.

To further examine the specificity of the small molecule compound FN1-8, as well as its inhibitory mechanisms, we tested whether over-expressing GLI2 protein could attenuate the cell killing effect of FN1-8. The transfection experiment was performed as described above. After 5 days, apoptosis analysis using flow cytometry was performed to quantify the experiment. Significantly more apoptotic cells were found in SW480 cells transfected with empty vector (48.1%) than in SW480 cells transfected with the Gli2 expression construct (27.7%). This result also indicated that FN1-8 induced apoptosis in cancer cells by inhibiting the GLI3 transcription activator function.

To confirm the result that GLI2 over-expression attenuates the apoptosis induction of FN1-5 and FN1-8 in colon cancer cells SW480, Western blot analysis was performed to test expression of the canonical Wnt signaling key component (cytosolic β-catenin), its down-stream target (Surviving), and some key players in the apoptosis pathway (cytochrome c and active PARP (cleaved form) as positive regulators of apoptosis; Surviving as inhibitor of apoptosis). β-actin served as loading control. The results obtained were consistent with the flow cytometry analysis of apoptosis reported above (data not shown). These data further supported other data that both FN1-5 and FN1-8 may induce apoptosis in some cancer cells through inhibition of the GLI3 transcription activator function.

To confirm the result that Gli2 over-expression attenuates apoptosis induction of FN1-5 and FN1-8 in colon cancer cells through reactivation of the Hh signaling pathway, semi-quantitative RT-PCR was used to analyze the Hh signaling key component and its down-stream target (Shh, Ptch1, Gli1, Gli3). GAPDH served as a control. It was found that the results were consistent with the a flow cytometry analysis of apoptosis reported above (data not shown).

Example 35

Figure 16:
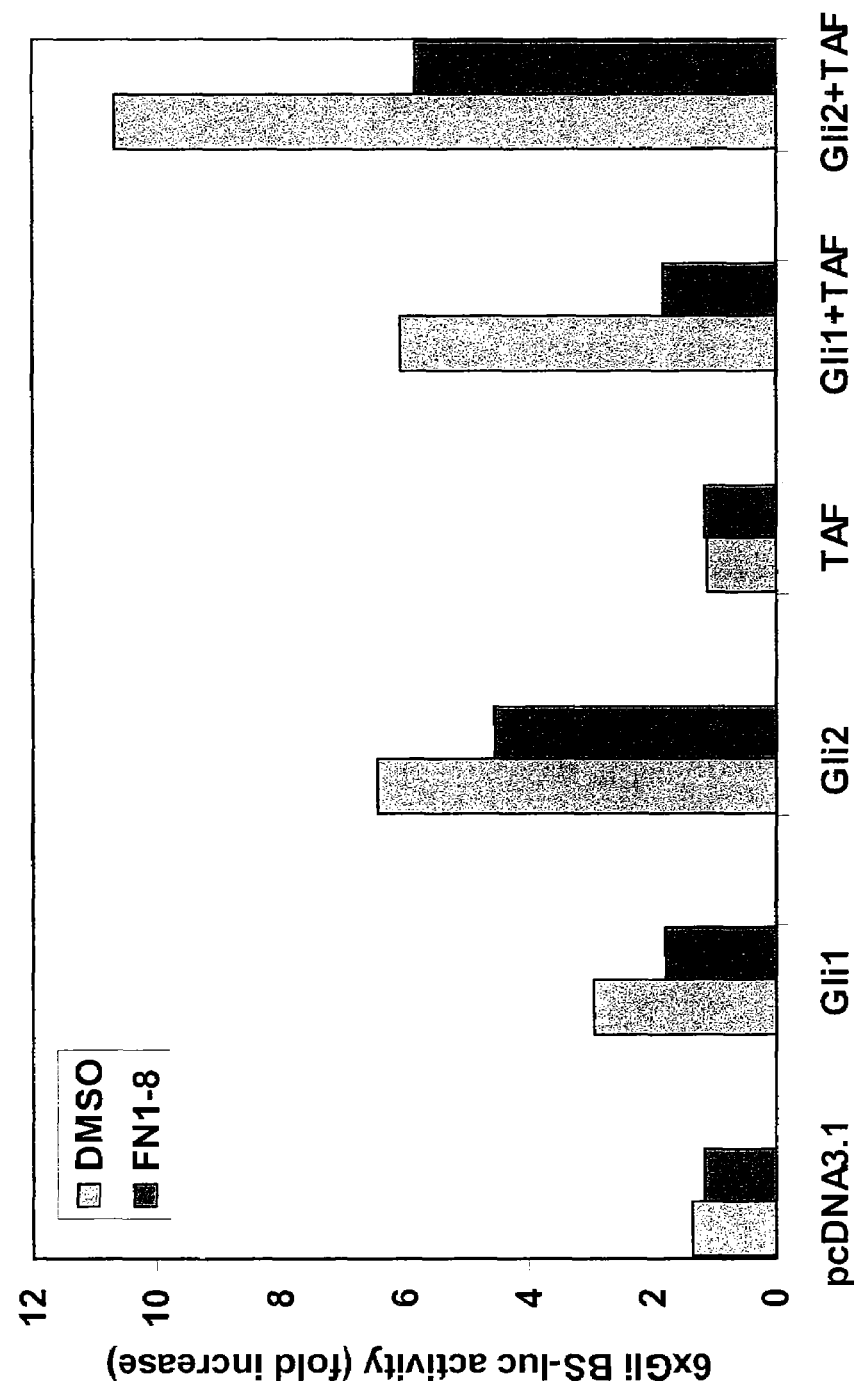
FIG. 16 shows that small molecule compound FN1-8 reduces GLI protein-TAF-induced transcriptional activation in the NSCLC cell line A549. Details are described in Example 35.

Small Molecule Compounds Inhibit the Protein-Protein Interaction Between GLI Polypeptides and TAF Proteins Resulting in Inhibition of GLI-TAF-Induced Transcription Activity Further, the specificity of the compounds of the present invention in inhibiting GLI activity and to determine whether these compounds block the interaction between GlLI and $TAF_{II}31$ as described above, was examined. Specifically, in this analysis, an expression construct linking the 6 repeats of GLI-binding sites (6xGLI BS) to a luciferase reporter gene as a surrogate measurement of the GLI-dependent transcription was used to examine the 6xGLI BS-luciferase activity after treatment of NSCLC A549 cells with compound FN1-8. The result of this experiment demonstrated that over-expression of GLI1 or GLI2 alone significantly increased the 6xGLI BS-luciferase activity (FIG. 16). Co-expression of $TAF_{II}31$ with either GLI1 or GLI2 further increased the 6xGLI BS-luciferase activity to a significantly higher level than that by GLI1 or GLI2 alone, while overexpressing $TAF_{II}31$ alone did not have any effect (FIG. 16). This finding again confirmed that both GLI1 and GLI2 specifically bound to the GLI-binding sites and were functionally active in transcription. This result further indicated that $TAF_{II}31$ may interact with the GLI proteins as a co-activator. After treatment of the A549 cells for 16-20 hours with 20 μM, FN1-8 both GLI alone and GLI/$TAF_{II}31$ induced 6xGLI BS-luciferase transcription was reduced. Interestingly, while the transcription activity by GLI alone was reduced by approximately 30%, transcription activity in the A549 cells cotransfected with $TAF_{II}31$ was reduced by about 50% for GLI2 and by about 70% for GLI1. This result indicated that FN1-8 may be a specific inhibitor of the interaction between GLI proteins and $TAF_{II}31$.

Figure 23:
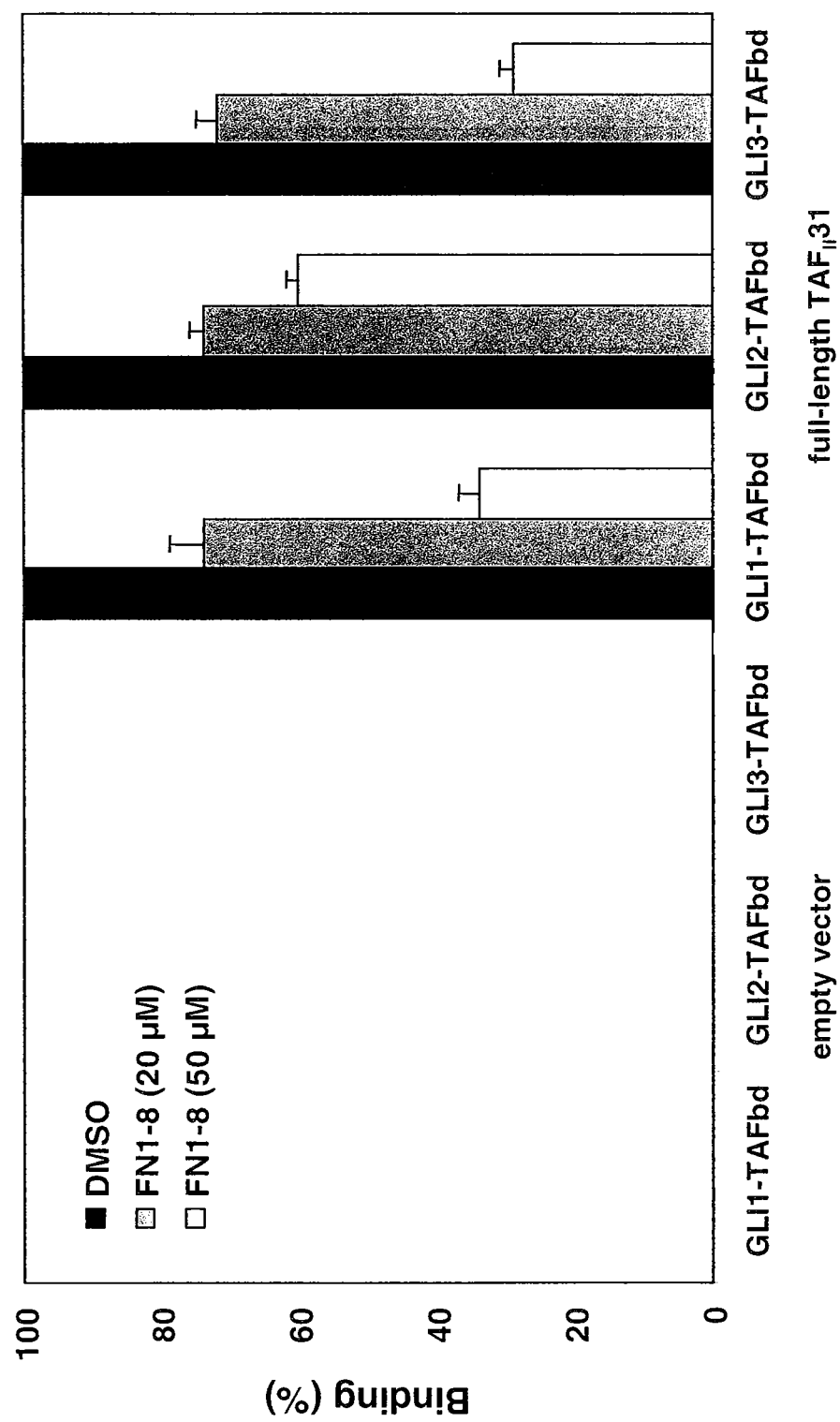
FIG. 23 shows the quantification of a co-immunoprecipitation analysis demonstrating that the small molecule compound FN1-8 blocks the protein-protein interaction between GLI proteins and $TAF_{II}31$ protein. The binding between GLI-TAF binding domain peptides (GLI-TAFbd) and $TAF_{II}31$ protein was quantified by measuring the intensity of each band of an co-immunoprecipitation experiments with arbitrary unit. The binding after DMSO treatment was set to 100% for each GLI-TAFbd peptide. The binding was interfered by FN1-8 in dose-dependent manner: the binding for GLI1-TAFbd was 73.6% and 33.5%, for GLI2-TAFbd was 73.8% and 60%, for GLI3-TAFbd was 71.6% and 28.6%, after treatment with 20 μM and 50 μM FN1-8, respectively. Details are described in Example 35.

In a co-immunoprecipitation experiment it was demonstrated that the small molecule compound FN1-8 blocked the protein-protein interaction between the TAF binding domain of GLI proteins and $TAF_{II}31$ protein (FIG. 23). Specifically for this experiment, biotinylated TAF binding domain of GLI proteins, GLI1, GLI2, and GLI3 (see below) were custom synthesized at Genemed Synthesis, Inc. The GLI-TAF binding domain (GLI-TAFbd) peptide sequences were as follows;

```
GLI1-TAFbd:  (NH2)-LDSLDLDNTQLDFVAILDEPQG-(COOH);

GLI2-TAFbd:  (NH2)-VDSQLLEAPQIDFDAIMDDGDH-(COOH);
and

GlLI-TAFbd:  (NH2)-LDSHDLEGVQIDFDAIIDDGDH-(COOH)
```

$TAF_{II}31$ proteins were prepared by using the TNT quick coupled transcription/translation systems (Promega) according to the manufacturer's protocol. The full-length $TAF_{II}31$ cDNA insert cloned into the (c-myc-tag)pCDNA3.1 expression vector was used as template in this in vitro translation system. An empty (c-myc-tag)pCDNA3.1 expression vector was used as a control. The biotinylated GLI peptides (i.e., the TAF binding domains of three different GLI proteins) were incubated with the $TAF_{II}31$ protein in the presence or absence of small molecule compound FN1-8 (at 20 μM and 50 μM). Then the biotinylated GLI-peptide-$TAF_{II}31$ complexes were precipitated with streptavidine agarose followed by immunoblotting with an anti-c-myc antibody (A-14; Santa Cruz Biotech, Inc.; Cao et al., 2001, *Science* 293:115-120). It was found that, in this assay, addition of 50 μM FN1-8 diminished the formation of the GLI-peptide-$TAF_{II}31$ complexes (FIG. 23). Specifically, it appeared that FN1-8 was more potent in blocking the protein-protein interaction between $TAF_{II}31$ and the TAF binding domains of GLI3 and GLI1 than with the TAF binding domain of GLI2 (FIG. 23). As a control, there was no pull-down of $TAF_{II}31$ by all three GLI peptides when the empty (c-myc-tag)pCDNA3.1 expression vector was used in in vitro translation system (FIG. 23).

In summary, these data indicated that the small molecule compound FN1-8 blocked the protein-protein interaction between the TAF binding domain of GLI proteins (more preferably GLI1 and GLI3) and $TAF_{II}31$ protein, consistent with the GLI/$TAF_{II}31$ dependent transcription reporter assays described above. This GLI-peptide/$TAF_{II}31$ protein-protein interaction assay can also be used in a method for screening for agents that inhibit the protein-protein interaction assay between a GLI protein (or GLI peptide as described above). In this method, an agent to be validated or screened for would be incubated with a GLI protein (or GLI peptide) and a $TAF_{II}31$ protein, as described above.

Example 36

Small Molecule Compound FN1-8 Suppresses Tumor Growth in Vivo (Mouse Xenograft Model: NSCLC H460)

Figure 17:
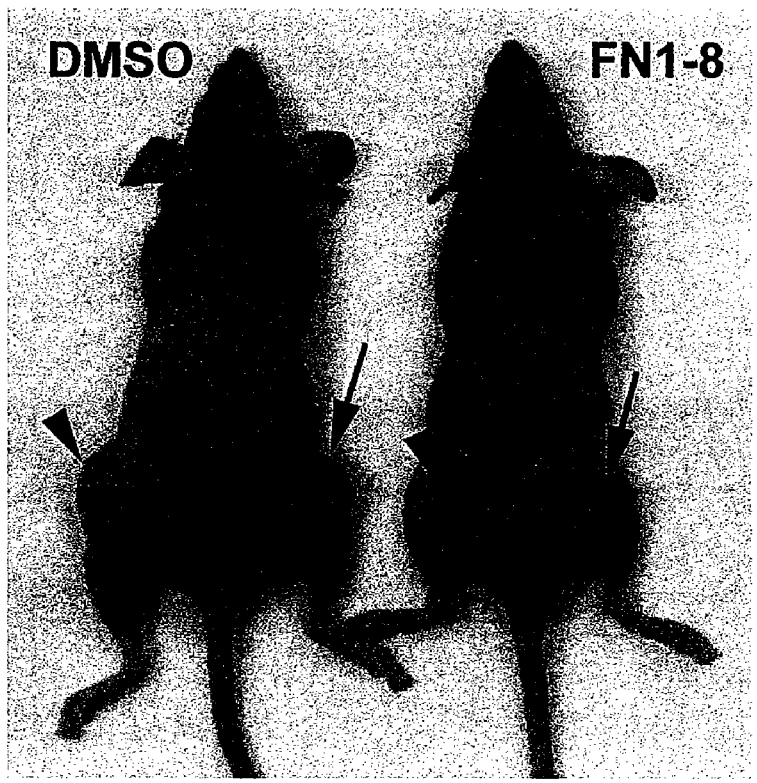
FIG. 17 shows the in vivo efficacy of small molecule compound FN1-8 in mouse Xenograft Models NSCLC H460 (arrows) and melanoma LOX (arrow heads). Tumor growth is significantly suppressed after treatment with FN1-8. Details are described, e.g., in Examples 36 and 37.

In vivo efficacy study of small molecule compound FN1-8 were performed using a Mouse Xenograft Model (NSCLC H460). Mice were injected s.c. with $3 \times 10^6$ cells in the dorsal area in a volume of 100 μl. (FIG. 17, arrow). 7 days after inoculation, the mice started receiving treatments with FN1-8 at a dose of 50 mg/kg body weight daily for 2×6 days (n=6). DMSO alone was used as control (n=7). FN1-8 and DMSO were adjusted in a volume of 40 μl for i.p. injection in the abdomens of the mice. Arrows in FIG. 18A indicate the time points of each injection. Tumor size (length and width according to their shapes) was measured with a caliper every three days. Tumor volumes were calculated using the equation $x^2y$ (where x<y). As can be seen in FIGS. 17 and 18, tumor growth was significantly suppressed after treatment with the small molecule compound FN1-8.

Three weeks after the initial tumor inoculation and the treatment as described above, tumors were dissected from the mice of each group and their weights were measured using a scale. Tumor weight dramatically decreased after the treatment with FN1-8 compound (FIGS. 18B and 18C).

Example 37

Small Molecule Compound FN1-8 Suppresses Tumor Growth in Vivo (Mouse Xenograft Model: Melanoma LOX)

Figure 19:
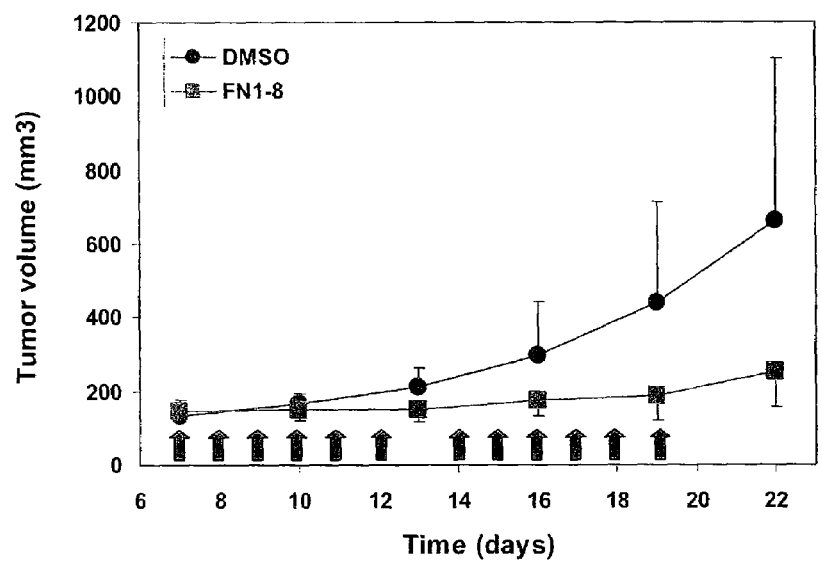
FIG. 19 shows an in vivo efficacy study of small molecule compound FN1-8 using a Mouse Xenograft Model (Melanoma LOX). A. Tumor growth was dramatically suppressed after treatment with the small molecule compound FN1-8. Arrows indicate daily injection of small molecule compound FN1-8 or DMSO as a control (each two times for 6 consecutive days). B. Tumors dissected from the mice of each group are shown. DMSO, DMSO treatment; FN1-8, treatment with small molecule compound FN1-8 as described herein. C. Tumor weight dramatically decreased after treatment with FN1-8. Results are the means±SD (error bars). Details are described, e.g., in Example 37.
Figure 19:
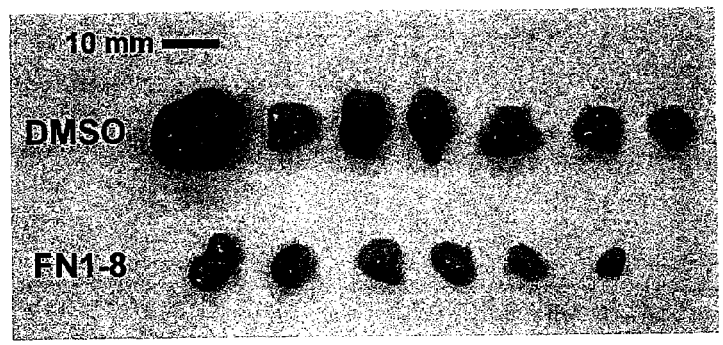
Figure 19:
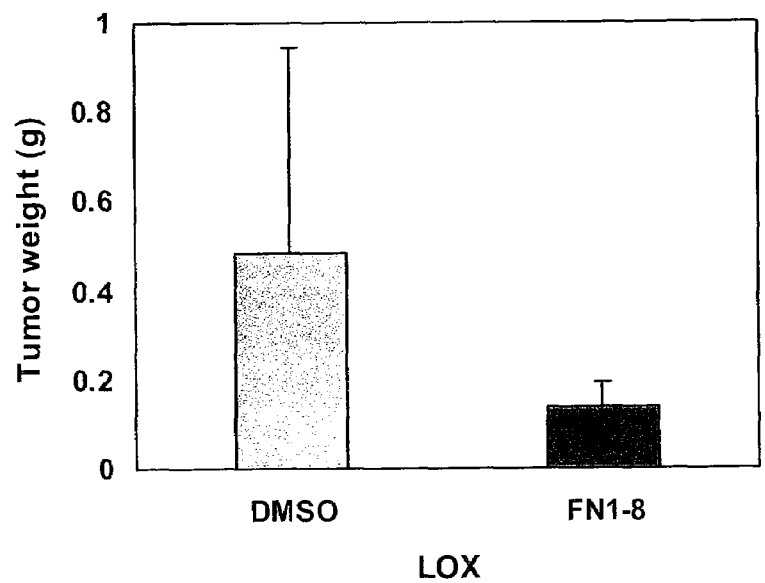

In vivo efficacy study of small molecule compound FN1-8 were performed using a Mouse Xenograft Model (Melanoma Lox). Mice were injected s.c. with $3 \times 10^6$ cells in the dorsal area in a volume of 100 µl. FIG. 17, arrow heads). 7 days after inoculation, the mice started receiving treatments with FN1-8 at a dose of 50 mg/kg body weight daily for 2×6 days (n=9). DMSO alone was used as control (n=10). FN1-8 and DMSO were adjusted in a volume of 40 µl for i.p. injection in the abdomens of the mice. Arrows in FIG. 19A indicate the time points of each injection. Tumor size and tumor volumes were calculated as described above. As can be seen in FIGS. 17 and 19, tumor growth was dramatically suppressed after treatment with the small molecule compound FN1-8.

Three weeks after the initial tumor inoculation and the treatment as described above, tumors were dissected from the mice of each group and their weights were measured using a scale. Tumor weight dramatically decreased after the treatment with FN1-8 compound (FIGS. 19B and 19C).

The in vivo efficacy study of small molecule compounds FN1-5 and FN1-8 in the Mouse Xenograft Model (NSCLC H460) was repeated using lower doses of the compounds. Mice were injected as described above. 9 days after inoculation, the mice started receiving treatments with the compounds at a low dose of 15 mg/kg body weight daily for 2×6 days (n=7). DMSO alone was used as control (n=7). FN1-8 and DMSO were adjusted in a volume of 50 µl for i.p. injection in the abdomens of the mice. 24 days after the initial tumor inoculation, tumors were dissected from the mice of each group and their weights were measured using a scale. Tumor weight decreased after the treatment with small molecule compound FN1-8 (data not shown). However, tumor weight in mice treated with low dose of compound FN1-5 were similar as the DMSO control group. This low dose in vivo result is consistent with the in vitro data shown herein.

Example 38

Small Molecule Compound FN1-8 Does Not Affect Tumor Growth in Vivo (Mouse Xenograft Model: Colon Cancer HT29)

Figure 20:
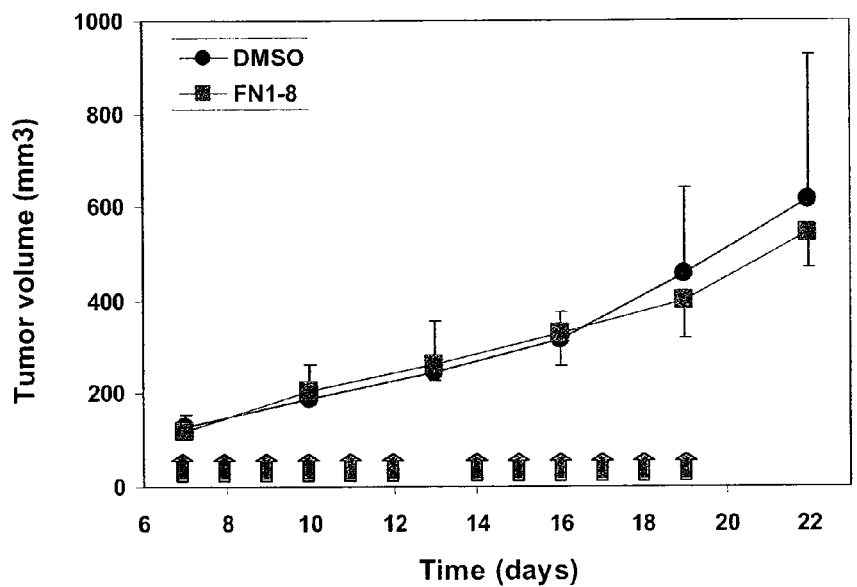
FIG. 20 shows an in vivo efficacy study of small molecule compound FN1-8 using a Mouse Xenograft Model (Colon Cancer HT29). See, Example 35 for details. A. Tumor growth was not affected after treatment with the small molecule compound FN1-8. Arrows indicate daily injection of small molecule compound FN1-8 or DMSO as a control (each two times for 6 consecutive days). B. Tumor weight after treatment with FN1-8 is similar to the DMSO control group. Results are the means±SD (error bars). Details are described, e.g., in Example 38.
Figure 20:
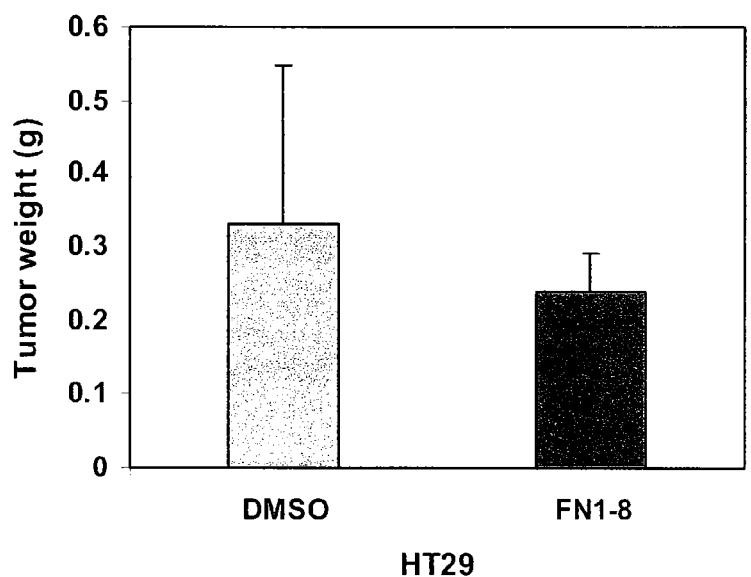

In vivo efficacy study of small molecule compound FN1-8 were also performed using a negative Mouse Xenograft Model (Colon Cancer HT29). Mice were injected s.c. with $3 \times 10^6$ cells in the dorsal area in a volume of 100 µl. 7 days after inoculation, the mice started receiving treatments with FN1-8 at a dose of 50 mg/kg body weight daily for 2×6 days (n=2). DMSO alone was used as control (n=4). FN1-8 and DMSO were adjusted in a volume of 40 µl for i.p. injection in the abdomens of the mice. Arrows in FIG. 20A indicate the time points of each injection. Tumor size was measured with a caliper every three days. Tumor volumes were calculated using the equation $x^2y$ (where x<y). As can be seen in FIG. 16A, tumor growth was not affected after treatment with the small molecule compound FN1-8. This result is consistent with in vitro data showing no effect of FN1-8 on GLI3 activation in HT29 cells and no Gli3 RT-PCR product (e.g., see FIG. 12 and data not shown). Tumor weight after the treatment with FN1-8 is similar to the DMSO control group (FIG. 20B). Results are the means±SD (error bars).

In a separate experiment 7 days after inoculation, the mice started receiving treatments with FN1-8 or FN1-5 at a low dose of 15 mg/kg body weight daily for 2×6 days (n=7), then another round of treatment at 30 mg/kg body weight daily for 1×6 days. DMSO alone was used as control (n=7). The compounds and DMSO were adjusted in a volume of 50 µl for i.p. injection in the abdomens of the mice. 43 days after the initial tumor inoculation, tumors were dissected from the mice of each group and their weights were measured using a scale. It was found that HT29 tumor weight after the treatment with FN1-8 was similar to the DMSO control group (data not shown). It was further found that treatment with FN1-5 slightly decreased the tumor weight (data not shown). These results are consistent with in vitro data with HT29 cells showing that FN1-5, but not FN1-8 induced cell killing and apoptosis in the colon cancer cell line HT29 (see Example 7).

Example 39

Small Molecule Compound FN1-8 Suppressed Tumor Growth in Vivo (Mouse Xenograft Model: NSCLC A549

In vivo efficacy study of FN1-8 in Mouse Xenograft Model (NSCLC A549) was also examined. Mice were injected s.c. with $3 \times 10^6$ cells in the dorsal area in a volume of 100 µl. 10 days after inoculation, the mice started receiving treatments with the small molecule compound FN1-8 at a low dose of 15 mg/kg body weight daily for 2×6 days (n=5), then another round of treatment at 30 mg/kg body weight daily for 1×6 days. DMSO alone was used as control (n=5). FN1-8 and DMSO were adjusted in a volume of 50 µl for i.p. injection in the abdomens of the mice. 43 days after the initial tumor inoculation, tumors were dissected from the mice of each group and their weights were measured using a scale. Tumor weight decreased after treatment with FN1-8 compound compared to the DMSO control group (data not shown). This low dose in vivo result is consistent with in vitro data presented herein.

Example 40

Effect of Small Molecule Compound FN1-8 on the Hedgehog Pathway in Tumors in Vivo To examine whether the lead compound FN1-8 suppressed tumor growth through inhibition of the Hedgehog signaling pathway in vivo, expression of the key components and direct target genes of the Hh pathway (e.g., Shh, Ptch1, Gli1, Gli2, Gli3, Dvl-3) were analyzed by semi-quantitative RT-PCR using total RNA isolated from the xenograft tumors. GAPDH served as a control. This RT-PCR analysis was performed using a "pooled" tumor from two randomly selected mice of each group with reasonable size tumors. It was found that Hh signaling was inhibited by FN1-8 in NSCLC tumor (H460) (data not shown). However, no noticeable changes in the Hh signaling were observed in the negative control HT29 tumor after FN1-8 treatment in vivo. These results are consistent with in vitro results (e.g., see Tables 2 and 3 for inducing apoptosis in H460 and HT29 cells) and suggest that small molecule compound FN1-8 may specifically suppress tumor growth in vivo through inhibition of the Hh pathway.

Example 41

Effect of Small Molecule Compound FN1-8 on the Canonical Wnt Pathway in Tumors in Vivo To examine whether the lead compound FN1-8 suppressed tumor growth through inhibition of the Wnt signaling pathway in vivo, Western blot analysis of cytosolic proteins isolated from the H460 and HT29 xenograft tumors was performed. GAPDH served as a control. This Western Blot analysis was performed using a "pooled" tumor from two randomly selected mice of each group with reasonable size tumors. It was found that expression of the key indicator of the canonical Wnt activation, Dvl-3 and cytosolic beta-catenin, was down-regulated in FN1-8 treated H460 tumor compared to DMSO treatment (data not shown). However, no noticeable changes of the Dvl-3 and cytosolic β-catenin levels were observed in the negative control HT29 tumor after FN1-8 treatment in vivo (data not shown).

Example 42

Effect of Small Molecule Compound FN1-8 on the Body Weight of Mice After In Vivo Treatment As one preliminary in vivo toxicity study of FN1-8, it was examined if there was loss of body weight in the mice after the FN1-8 treatment. Three weeks after the initial tumor inoculation and the treatment as described in the previous examples, body weights of DMSO control group (n=11) and FN1-8 treated group (n=8) were measured using a scale. No noticeable loss of the body weight was observed after the FN1-8 treatment (data not shown).

Example 43

Pharmacokinetic Analyses of Small Molecule Compounds FN1-5 and FN1-8 in Mice

Figure 21:
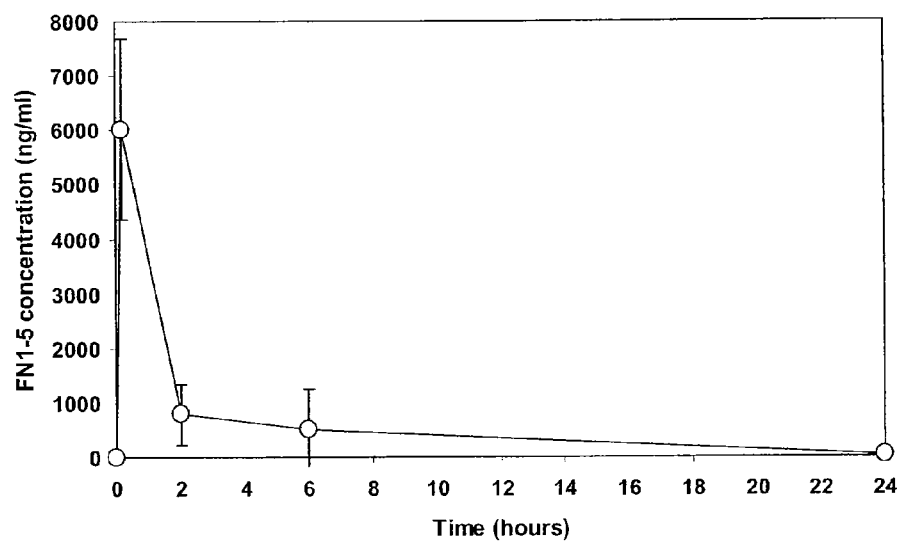
FIG. 21 shows a pharmacokinetic analysis of small molecule compounds FN1-5 (A) and FN1-8 (B) in mice (i.p. injection). Results are presented as mean values of the data obtained from three mice with SD (error bars). Details are described in Example 43.
Figure 21:
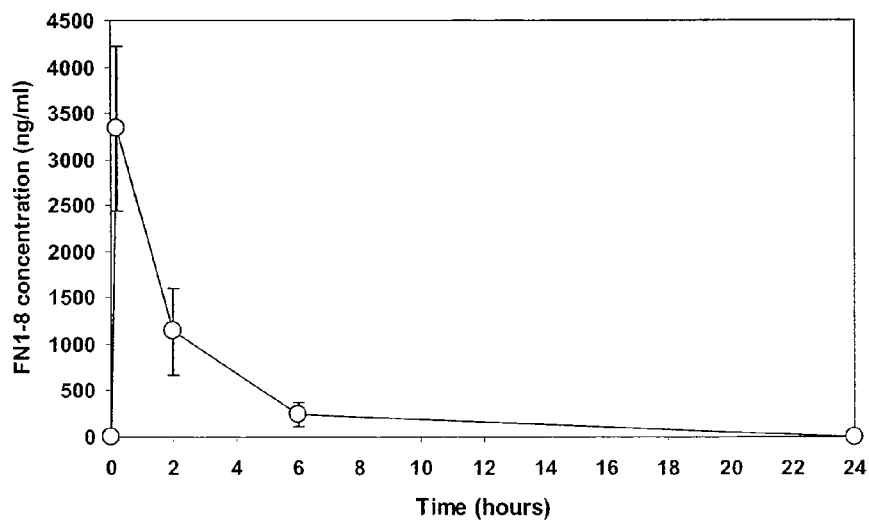

Three mice were i.p. injected in the abdomens with small molecule compounds FN1-5 at a dose of 30 mg/kg body weight. Then plasma was collected from the tail-vein of each mouse at 10 min, 2 hours, 6 hours and 24 hours after FN1-5 injection. The concentration of FN1-5 in each plasma sample was determined by mass spectroscopy and is shown in FIG. 21A. This analysis shows a quick uptake of FN1-5 into plasma within 10 min after the compound injection. The FN1-5 concentration in the serum then diminishes within 24 hours, suggesting that FN1-5 can be absorbed in vivo.

Similarly, the pharmacokinetic properties of small molecule compound FN1-8 were analyzed (FIG. 21B). Comparing the uptake of FN1-8 to FN1-5, the uptake of FN1-5 after i.p injection seems to be better, by about 2 fold.

Figure 22:
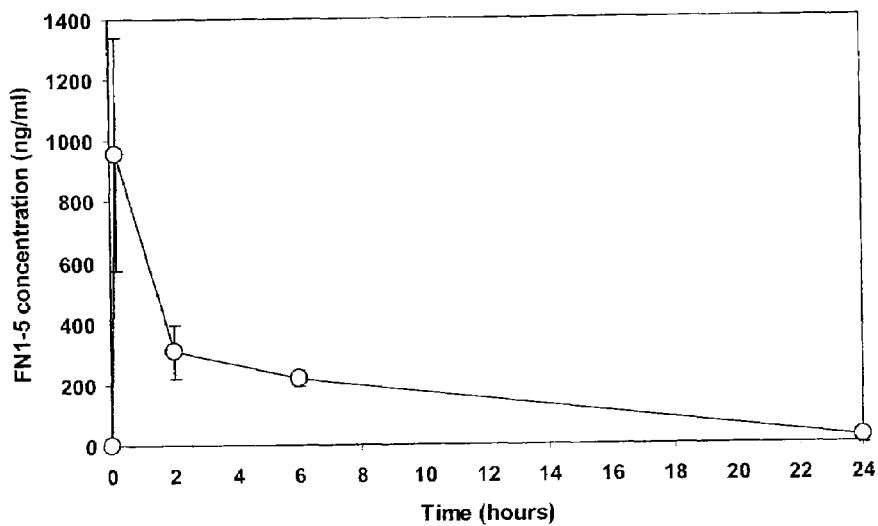
FIG. 22 shows a pharmacokinetic analysis of small molecule compounds FN1-5 (A) and FN1-8 (B) in mice (oral administration). Results are presented as mean values of the data obtained from three mice with SD (error bars). Details are described in Example 43.
Figure 22:
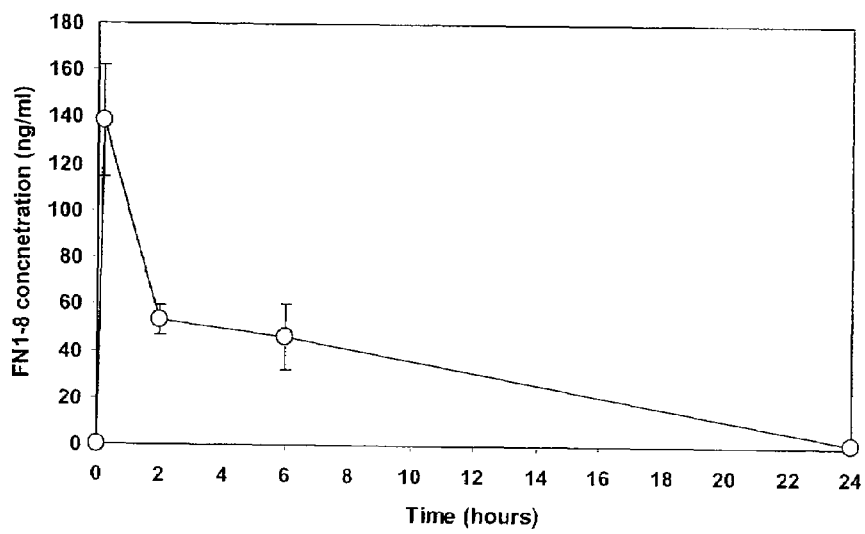

In another pharmacokinetic study, three mice were orally administrated with the small molecule compound FN1-5 at the dose of 30 mg/kg body weight. Then, as described above, plasma was collected from the tail-vein of each mouse and the concentration of FN1-5 in each plasma sample was determined by mass spectroscopy. The results are shown in FIG. 22A. The result of this analysis indicates that there is a quick update of FN1-5 into plasma (within 10 min after the compound injection) which diminishes within 24 hours. Again, this result suggests that FN1-5 can be made orally available for the treatment of cancer.

Similarly, the pharmacokinetic properties of orally administered small molecule compound FN1-8 were analyzed (FIG. 22B). Comparing the uptake of FN1-8 to FN1-5, the uptake of FN1-5 after oral administration seems to be better, by about 7 fold.

What is claimed is:

1. A small molecule compound of the formula

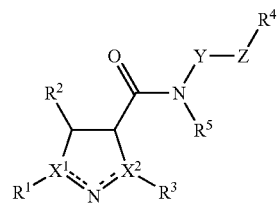

wherein
each of $X^1$ and $X^2$ independently N or C, wherein one of $X^1$ and $X^2$ is N and one of $X^1$ and $X^2$ is C, such that the ring N forms a double bond with whichever of $X^1$ and $X^2$ is C;
each of $R^1$, $R^2$ and $R^3$ is independently selected from the group consisting of $C_1$-$C_6$ alkyl, aryl, heteroaryl, cycloalkyl and heterocycloalkyl, optionally substituted with 0-3 $R^6$ groups each independently selected from the group consisting of H, halogen, $C_1$-$C_6$ alkyl, —$OR^7$, —$C(O)R^7$, —$OC(O)R^7$, —$N(R^7,R^7)$, —$NR^7S(O)_2R^7$, —$C(O)N(R^7,R^7)$, —$N(R^7)C(O)R^7$, —$N(R^7)C(O)N(R^7,R^7)$, —$C(NR^7)N(R^7,R^7)$, —$N(R^7)C(NR^7)N(R^7,R^7)$ and $S(O)_mR^7$ wherein subscript m is 0, 1 or 2;
Y is a direct bond or $C_1$-$C_4$ alkyl;
Z is a member selected from the group consisting of $C_1$-$C_4$ alkyl, aryl and heteroaryl;
$R^4$ is H, halogen, —$OR^7$, —$OC(O)R^7$, —$C(O)OR^7$, —$N(R^7,R^7)$, —$NR^7S(O)_2R^7$, —$C(O)N(R^7,R^7)$, —$N(R^7)C(O)N(R^7,R^7)$, —$C(NR^7)N(R^7,R^7)$, $NR^7C(O)R^7$, and $S(O)_mR^7$ wherein subscript m is 0, 1 or 2;
$R^5$ is H, $C_1$-$C_6$ alkyl, or optionally combined with Y to form a 5 to 6 membered heterocycle;
each $R^7$ is independently H or $C_1$-$C_6$ alkyl;
and salts, racemates, disasteriomers, enantiomers, geometric isomers, and prodrugs thereof.

2. The small molecule compound of claim 1, wherein each of $R^1$, $R^2$ and $R^3$ is aryl.

3. The small molecule compound of claim 2, wherein each of $R^1$, $R^2$ and $R^3$ is phenyl.

4. The small molecule compound of claim 2, wherein $R^4$ is hydroxy.

5. The small molecule compound of claim 4, wherein Z is $C_1$-$C_4$ alkyl.

6. The small molecule compound of claim 4, wherein Z is aryl.

7. The small molecule compound of claim 6, wherein Z is phenyl.

8. The small molecule compound of claim 1, wherein
each of $R^1$, $R^2$ and $R^3$ is phenyl;
Y is $C_1$-$C_4$ alkyl;
Z is $C_1$-$C_4$ alkyl or phenyl; and
$R^4$ is hydroxy.

9. The small molecule compound of claim 8, wherein $X^1$ is C and $X^2$ is N.

10. The small molecule compound of claim 9, having the structure

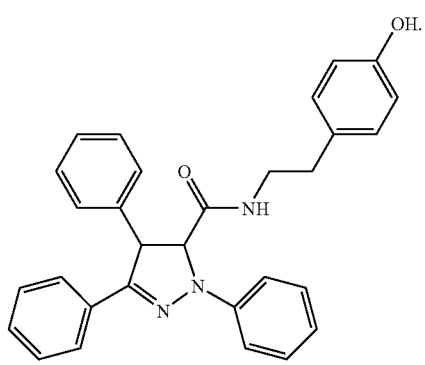

11. The small molecule compound of claim 9, having the structure

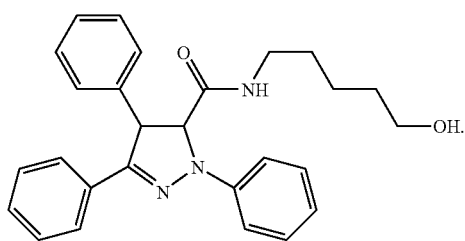

12. The small molecule compound of claim 8, wherein $X^1$ is N and $X^2$ is C.

13. The small molecule compound of claim 12, having the structure

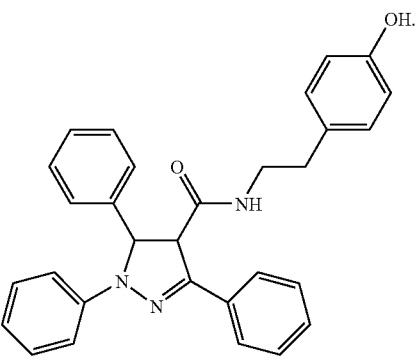

14. The small molecule compound of claim 12, having the structure

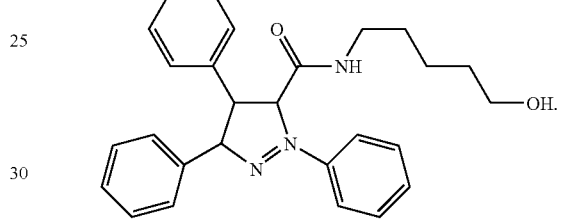

15. A pharmaceutical composition comprising:
(i) the small molecule compound of claim 1; and
(ii) a pharmaceutically acceptable carrier.

16. The small molecule compound of claim 1, which is the small molecule compound or a salt thereof.

\* \* \* \* \*